United States Patent [19]

Douglas et al.

[11] 4,452,980

[45] * Jun. 5, 1984

[54] TRIAZINONES

[75] Inventors: George H. Douglas, Malvern; William L. Studt, Harleysville; Chong M. Won, Warrington; Stuart A. Dodson, Lansdale; Jerome J. Zalipsky, Melrose Park, all of Pa.

[73] Assignee: William H. Rorer, Inc., Fort Washington, Pa.

[*] Notice: The portion of the term of this patent subsequent to Jan. 20, 1998 has been disclaimed.

[21] Appl. No.: 394,128

[22] Filed: Jul. 1, 1982

Related U.S. Application Data

[62] Division of Ser. No. 225,198, Jan. 15, 1981, Pat. No. 4,338,441, which is a division of Ser. No. 959,611, Nov. 13, 1978, Pat. No. 4,246,409.

[51] Int. Cl.³ .................. C07D 251/42; C07D 251/16
[52] U.S. Cl. ................................................ 544/211
[58] Field of Search ........................ 424/249; 544/211

[56] References Cited

U.S. PATENT DOCUMENTS

| | | | |
|---|---|---|---|
| 4,198,408 | 4/1980 | Condouris et al. | 424/249 |
| 4,198,409 | 4/1980 | Yelnosky et al. | 544/211 |
| 4,203,983 | 5/1980 | Yelnosky et al. | 424/249 |
| 4,203,984 | 5/1980 | Douglas et al. | 424/249 |
| 4,203,985 | 5/1980 | Yelnosky et al. | 424/249 |
| 4,246,409 | 1/1981 | Douglas et al. | 544/211 |
| 4,338,441 | 7/1982 | Douglas et al. | 544/211 |

*Primary Examiner*—John M. Ford
*Attorney, Agent, or Firm*—James A. Nicholson; Alexis Barron; Martin F. Savitzky

[57] ABSTRACT

Novel s-triazine compounds are prepared as derivatives of the corresponding amidinourea and amidinothiourea compounds by reacting with an activated form of an acid amide to give substituted s-triazinones and thiones respectively, of the formula

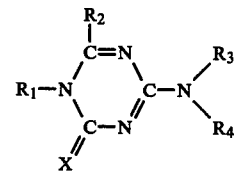

The s-triazinones and thiones are useful derivatives in analyzing for the corresponding amidinourea or amidino thiourea precursors and also have useful pharmacological properties which make them suitable for a variety of medicinal purposes including use as antidiarrheal agents.

1 Claim, No Drawings

TRIAZINONES

This application is a divisional application of copending application Ser. No. 225,198 filed Jan. 15, 1981, now U.S. Pat. No. 4,338,441 which is a divisional of application Ser. No. 959,611 filed Nov. 13, 1978, now U.S. Pat. No. 4,246,409.

FIELD OF THE INVENTION

This invention pertains to a novel method for cyclizing amidinoureas and amidino thioureas, to novel heterocyclic compounds produced by the method, and to a novel analytical method.

Amidinourea and amidinothiourea and their derivatives are known in the art and have been previously disclosed as having useful pharmacological properties. Such compounds are disclosed for example in U.S. Pat. Nos. 4,060,635 and 4,058,557 and in co-pending application Ser. No. 671,762 all of which are assigned to the assignee of the present invention.

In the development of pharmacologically active compounds for drug use in the treatment of human disorders it is well recognized that extensive testing is carried out to define among other things the mode of action, toxicity and ultimate fate of the drug which is administered to the patient. In particular, the amidinoureas continue to be extensively investigated for a variety of pharmacodynamic effects. An important part of such investigations involves the analyses of samples of materials such as body tissue, blood serum, secretions and excretions to determine the qualitative and quantitative presence of the drug in order to establish the characteristics of the drug with respect to absorption, diffusion and transport, biotransformation by decomposition or conjugation and ultimate elimination from the body following administration to humans or animals including test animals. Gas chromatographic analysis has been found to be a useful tool for detecting the presence of a drug in a sample containing a variety of other materials. However, for gas chromatographic detection the drug must be capable of being volatilized without degradation at the temperature of the carrier gas and must be inert to both the carrier gas and the column packing material.

Gas chromatographic analysis of polar organic amides has proved difficult owing to strong interaction between the functional groups and the surface active sites in the stationary materials comprising the chromatographic column. These difficulties can frequently be overcome by first converting the organic amides to less active derivatives such as by forming an alkyl ester of the carboxyl group followed by acylation of the primary amino group. Primary amino groups have also been derivatized by reacting with dimethyl-formamide dimethylacetal (DMF DMA) to form the dimethyl aminomethylene derivative. The same reagent has also been used to esterify carboxyl groups. More recently DMF DMA has been used to simultaneously derivatize carboxylic and amino groups by reacting with amino acids containing only primary amino and carboxyl groups; Analytic Letters, 5(8), 519–529 1972.

Since the use of gas chromatographic techniques to analyze for amidinoureas directly proved difficult, derivatization of the functional groups utilizing DMF DMA as the derivatizing reagent was attempted. The analysis of amidinoureas and amidinothioureas by gas chromatographic techniques was found to be facilitated by such derivatization though unexpectedly the derivatives obtained proved to be a novel class of s-triazinone and thione compounds, more particularly, 1,4-substituted 1,2-dihydro-1,3,5-triazin-2-ones and 1,4-substituted-1,2-dihydro-1,3,5 -triazin-2-thiones.

DESCRIPTION OF THE PRIOR ART

As disclosed in co-pending application Ser. No. 671,762, the disclosure of which is hereby incorporated by reference the amidinoureas can exist in various tautomeric or alternative structural forms. The same is true for the amidino thioureas. Among the theoretical forms of the amidinoureas described in said co-pending application are structures having primary amino groups and therefore it might be theorized that the dimethyl amino methylene derivative of such amidinoureas could be prepared by reacting with DMF DMA. Repeated efforts to prepare the derivatives of numerous amidinoureas led instead to the preparation of triazine compounds of novel structure which were nonetheless found to be suitable for gas chromatographic analysis to determine the qualitative and quantitative presence of the corresponding amidinourea. In an analogous way suitable triazine derivatives of the corresponding amidinothioureas are also prepared.

Substituted triazines are well known as are a variety of triazinones and thiones prepared by a number of synthetic routes, for example, as described in U.S. Pat. No. 3,585,197. However, it does not appear that prior disclosures taught that 1,4-disubstituted triazinones especially those having an aryl or aralkyl substituent, can be readily prepared in nearly quantitative yield by cyclizing the corresponding amidinoureas with a derivatizing agent in accordance with the present invention. The preparation of s-triazin-2-ones and s-triazin-2-thiones in accordance with this technique provides a variety of novel triazine derivatives which are biologically active when adminstered to mammalian species to produce useful pharmacotherapeutic effects. Accordingly, it is an object of this invention to provide a novel process for the preparation of triazines by cyclizing amidinoureas and amidinothioureas thereby to provide derivatives which are useful inter alia as analytical tools to determine the presence of the corresponding amidinoureas or amidinothioureas by gas chromotographic methods which would otherwise not be possible.

Additionally, it is an object of this invention to provide a novel class of compounds possessing useful pharmacological properties which novel compounds and their pharmaceutically acceptable salts can be used for the treatment of a variety of physiological disorders, e.g., diarrhea and other gastrointestinal disorders.

SUMMARY

In accordance with the present invention, there is provided a novel class of 1,4-substituted-1,2-dihydro-1,3,5-triazin-2-ones and thiones of formula I

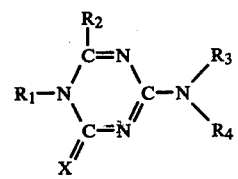

wherein:

X is oxygen or sulfur;
R₁ is aryl,
  aralkyl,
  5 or 6 membered heterocyclic groups or
  5 or 6 membered heterocyclic groups attached to the triazine through a lower alkylidene group;
R₂ is hydrogen or loweralkyl; and
R₃ and R₄ are each independently selected from the group consisting of hydrogen,
  hydroxyl,
  acyl,
  an aliphatic or substituted aliphatic group,
  an aromatic group,
  an aliphatic or aromatic ether group or a heterocyclic group;
  or together R₃ and R₄ are alkylene or alkylene interrupted by 0 to 2 hetero atoms which may be N, O or S so that R₃ and R₄ together with the nitrogen to which they are attached form a 3 to 7 membered ring containing 1 to 3 hetero atoms.

The cyclic derivative can be used to assay for the corresponding amidinourea or amidinothiourea by injecting a sample along with a suitable vaporizable carrier into a gas chromatograph. The compounds can also be used for pharmacotherapeutics by administering to animals or humans suitable dosage forms containing an effective amount for the treatment of gastrointestinal irregularities such as diarrhea.

In one aspect this invention pertains to a novel class of triazines which are prepared as derivatives of amidinoureas or amidinothioureas to provide a gas chromatographic method for detecting the presence of the amidinourea or amidinothiourea in a sample containing the amidinourea or amidinothiourea in admixture with unknown materials.

In another aspect this invention provides a novel analytical method to assay for amidinoureas and amidinothioureas in biological samples.

In yet another aspect, this invention provides a novel cyclizing reaction for the preparation of triazines and triazine derivatives.

In still another aspect, this invention provides compounds which are useful in pharmacotherapeutics particularly as antidiarrheals or as antimotility or antisecretory agents or as antispasmodic agents.

Certain of the novel compounds also have effects on nerve tissue indicating use in the control of the disorders involving abnormal nerve impulse transmission.

DESCRIPTION OF THE PREFERRED EMBODIMENTS

According to the novel compound aspect of this invention, there is provided a new class of substituted triazines, more particularly a novel class of s-triazinones and s-triazinthiones of the formula:

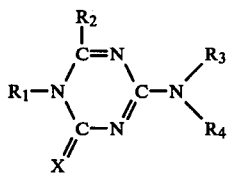

I wherein:
  X is oxygen or sulfur;
  R₁ is aryl,
    aralkyl,
    5 or 6 membered heterocyclic groups or
    5 or 6 membered heterocyclic groups attached to the triazine through a lower alkylidene group;
  R₂ is hydrogen or loweralkyl; and
  R₃ and R₄ are each independently selected from the group consisting of hydrogen,
    hydroxyl,
    acyl,
    an aliphatic or substituted aliphatic group,
    an aromatic group,
    an aliphatic or aromatic ether group, or
    a 5 or 6 membered heterocyclic group; or
  together R₃ and R₄ are alkylene or alkylene interrupted by 1 or 2 hetero atoms which may be N, O or S, so that R₃ and R₄ together with the nitrogen to which they are attached form a 3 to 7 membered ring containing 1 to 3 hetero atoms;
and their non-toxic pharmaceutically acceptable salts.

Depending upon the specific substitution, compounds of formula I above may be present in enolized or tautomeric forms. Certain of the compounds can also be obtained as hydrates or in different polymorphic forms. The structures used herein to designate novel compounds are intended to include the compound shown along with its alternative or transient states. The nomenclature generally employed to identify the novel triazine derivatives as disclosed herein is based upon the ring structure shown in formula I with the triazine ring positions numbered counterclockwise beginning with the nitrogen having the R₁ substitution.

s-triazinones and s-triazinthiones of this invention which form a preferred class of novel compounds, are those represented by the formula I-a:

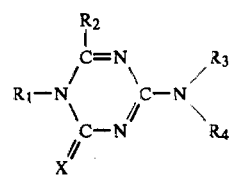

I-a wherein:
  X is oxygen or sulfur;
  R₁ is phenyl,
    benzyl or
    phenethyl;
  or phenyl, benzyl or phenethyl in which one or more of the phenyl hydrogens are substituted by loweralkyl,
    loweralkoxy,
    halo,
    haloloweralkyl,
    amino,
    nitro,
    acyloxy,
    acylamino,
    hydroxy,
    cyano,
    carboxyl, or
    loweralkylsulfonyl (especially 2'6'-disubstituted phenyl, benzyl or phenethyl);
  pyridyl or substituted pyridyl;
  R₂ is hydrogen or loweralkyl; and
  R₃ and R₄ are each independently selected from the group
    consisting of hydrogen,
    hydroxyl,
    loweralkanoyl, loweralkyl,
loweralkenyl,
loweralkynyl,
loweralkoxy,
haloloweralkyl,
hydroxyloweralkyl,
loweralkoxyloweralkyl,
phenoxyloweralkyl,
diloweralkylamino,
loweralkyl, or $R_3$ and $R_4$ together with the nitrogen to which they are attached form a 5 or 6 membered nitrogen heterocycle containing 0 to 1 additional hetero atoms which may be nitrogen,
oxygen or
sulfur;
and their non-toxic salts.

When $R_1$ is pyridyl in formula I-a above, the preferred groups are those wherein the pyridyl nitrogen is adjacent to the ring carbon attached to the triazinone ring, i.e. a 2-pyridyl and substituted pyridyls is which one or both pyridyl ring carbons adjacent to the carbon attached to the triazinone ring are substituted by loweralkyl,
loweralkoxy, or
haloloweralkyl.

Where $R_1$ is substituted phenyl,
benzyl or phenethyl, the preferred substituents on the phenyl moiety are the loweralkyl,
halo, and
loweralkoxyphenyl groups in the ortho positions.
The substituents may be the same or different.

A more specific group of preferred compounds according to this invention are the s-triazinones of formula I-b.

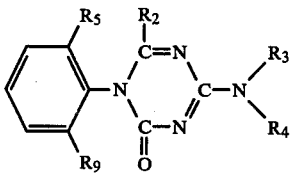

I-b wherein:
$R_2$ is hydrogen or
loweralkyl;
$R_3$ and $R_4$ are each hydrogen,
loweralkyl,
hydroxy,
loweralkoxy,
phenoxy,
diloweralkylaminoloweralkyl,
loweralkanoyl,
loweralkenyl and
loweralkynyl or
$R_3$ and $R_4$ together with the nitrogen to which they are attached form a 5 or 6 membered heterocyclic ring (preferably pyrrolidinyl,
oxazolidinyl,
thiazolidinyl,
pyrazolidinyl,
imidazolidinyl,
piperidyl,
piperazinyl,
thiamorpholinyl, or
morpholinyl).
$R_5$ is hydrogen,
halo,
loweralkyl or
loweralkoxy; and
$R_9$ is halo,
loweralkyl, or
loweralkoxy.

Another more specific preferred group are the s-triazinones of the formula I-c.

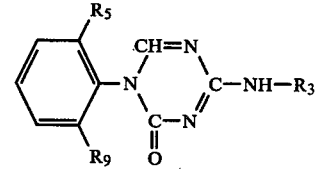

I-c wherein:
$R_3$ is hydrogen,
hydroxy,
loweralkyl,
loweralkoxy, or
diloweralkylaminoloweralkyl; and
$R_5$ and $R_9$ are each loweralkyl,
halo,
haloloweralkyl, or
loweralkoxy; and
$R_5$ and $R_9$ may be the same or different.

As employed above and throughout the disclosure, the following terms, unless otherwise indicated, shall be understood to have the following meanings:

"alkyl" means a saturated aliphatic hydrocarbon which may be either straight or branched chain preferably having no more than about 20 carbon atoms; loweralkyl being preferred; also included are the cycloalkyl groups such as cyclohexyl, cyclopropyl etc. and the cycloalkylalkyl groups such as cyclopropylmethyl and the like.

"loweralkyl" means an alkyl group as above, having 1 to 6 carbon atoms, suitable loweralkyl groups are methyl, ethyl propyl, isopropyl, butyl, sec-butyl, tert-butyl, pentyl and isopentyl.

"cycloalkyl" means an aliphatic monocyclic saturated carbocyclic group having 3 to 6 carbon atoms preferably cyclopropyl, cyclopentyl, and cyclohexyl.

"alkenyl" means an unsaturated aliphatic hydrocarbon having no more than about 20 carbon atoms and which contains one or more double bonds and which may be straight or branched chain with loweralkenyl, i.e. alkenyl of 2 to 6 carbons, being preferred.

"loweralkenyl" means alkenyl of 2 to 6 carbon atoms such as ethylene, propylene, butylene, isobutylene, etc.

"alkynyl" means an unsaturated aliphatic hydrocarbon having no more than about 20 carbon atoms and containing one or more triple bonds with lower alkynyl, i.e. alkynyl of 2 to 6 carbons, being preferred.

"loweralkynyl" means alkynyl of 2 to 6 carbon atoms such as propargyl, butynyl, pentynyl, etc.

"aryl" means phenyl and substituted phenyl.

¢substituted phenyl" means a phenyl group in which one or more of the hydrogens has been replaced by the same or different substituents including halo, loweralkyl, haloloweralkyl, nitro, amino, acylamino, hydroxy, loweralkoxy, aryl-loweralkoxy, acyloxy, cyano, haloloweralkoxy or loweralkylsulfonyl.

"aralkyl" means an alkyl (preferably a loweralkyl) in which one or more hydrogens is substituted by an aryl moiety (preferably phenyl or substituted phenyl), e.g. benzyl, phenethyl, etc.

"5 and 6 membered heterocyclic group" means a 5 or 6 membered ring having 1 to 3 hetero atoms which may be nitrogen, oxygen or sulfur including pyridyl, 2-pyridyl or 3-pyridyl; pyrimidyl, pyrazolyl, imidazolyl, furyl, thienyl, oxazoneyl, thiazolyl, piperidyl, morpholinyl etc. with the pyridyl groups being preferred.

"substituted pyridyl" means a pyridyl in which one or more of the hydrogens on the ring carbons have been replaced by substituents as given above with respect to substituted phenyl.

The terms "halo" and "halogen" include all four halogens; namely, fluorine, chlorine, bromine and iodine. The halo alkyls, halophenyl and halosubstituted pyridyl include groups having more than one halo substituent which may be the same or different such as trifluoromethyl, 1-chloro-2-bromo ethyl, chlorophenyl, 4-chloropyridyl, etc.

The term "acyloxy" is intended to mean an organic acid radical such as acetoxy, propionoxy, and the like.

The term "loweralkanoyl" is intended to include the acid radical of a loweralkanoic acid such as acetyl, propionyl and the like.

Among the compounds of formula I, a particularly preferred group of novel compounds are those in which the $R_1$ substituent is a substituted phenyl and particularly a phenyl having substituents in the 2 and 6 positions (i.e., ortho to the carbon attached to the triazine nitrogen). The preferred phenyl substituents are loweralkyl, loweralkoxy and halo. The preferred $R_3$ and $R_4$ substituents are those where $R_3$ and $R_4$ are the same and both are loweralkyl, halo-loweralkyl or loweralkoxy-loweralkyl. The preferred loweralkyl substituents are methyl, ethyl, propyl and isopropyl. The preferred halo substituents are chlorine and bromine. The preferred halo-lower alkyl are chloromethyl and trifluoromethyl.

The pyridyl substituents may be either 2-, 3-, or 4-pyridyls; preferred substituted pyridyls are those having substituents on the carbon or carbon atoms vicinal to the carbon attached to the triazine nitrogen.

According to the cyclizing process aspect of this invention, it has been found that an amidinourea can be cyclized to the corresponding s-triazinone by condensing the amidinourea with an organic reagent having an activated methylidene group or capable of forming an activated methylidene for example, a methylidene group having at least one available hydrogen atom and a leaving group such as di-substituted amino group attached to the methylidene carbon. As organic reagent for condensing an amidinourea or thiourea starting material to form an s-triazinone or s-triazinthiones there is suitably used an activated form of an acid amine or an ortho ester or acyl derivative such as a Vilsmeir reagent which will bring about acylation and ring closure of the amidinourea or thiourea to give s-triazinones and s-triazinthiones of formula I above. The cyclizing process can be used in the same manner to prepare s-triazinthiones from the corresponding amidinothioureas and it will be understood that in referring to the preparation of triazinones it is intended to include also the thiones. The reagent may be the dialkylacetyl of a di-alkyl-lowercarboxylic acid amide or the reaction product of a di-alkyl-lowercarboxylic acid amide and an alkylating agent. The reagent can be prepared in situ or in advance depending upon its stability. While this reaction finds applicability generally for cyclizing amidinoureas it is especially useful in preparing the novel s-triazinones of this invention. The synthesis of triazinones according to this invention can employ as starting material known amidinoureas or similar starting materials also known in the art, or the materials employed as precursors for cyclizing to form s-triazinones can be readily prepared by analogy to the preparation of the known starting materials. Suitable amidinourea starting materials are those disclosed in U.S. Pat. Nos. 4,060,635 and 4,058,557 and in copending application Ser. No. 671,762 the disclosures of which, as previously noted, are incorporated here by reference. Thus, the novel cyclizing process of this invention can be used to derivatize amidinoureas and thioureas of formula II below.

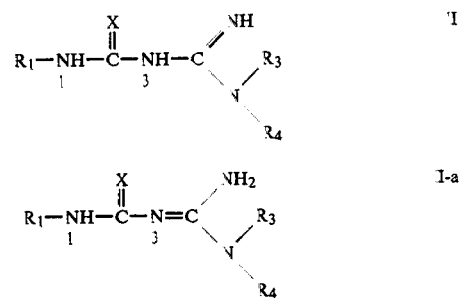

wherein X, $R_1$, $R_3$ and $R_4$ have the same meanings as above.

It should be understood that whereas the structure of the starting materials are shown here in a particular configuration for the purposes of illustration it is intended to include the various structural isomers as previously noted. By way of illustration, an alternative structure is shown by formula II-a. Where reference is made to the terminal nitrogens, it is intended to denote the urea nitrogen designated as position 1 in formula II and the unsubstituted amidino nitrogen.

Thus, there can be prepared in accordance with the process of this invention 1,3,5-triazin-2-ones and 1,3,5-triazin-2-thiones utilizing as starting materials any of the prior art amidinoureas or amidinothioureas including the 1-arylamidinoureas and thioureas of Formula III below which constitute a preferred group of starting materials.

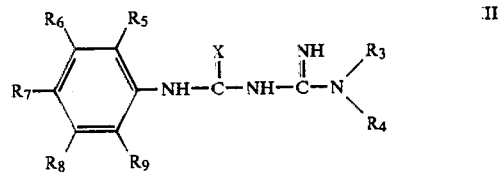

wherein X and the $R_3$ and $R_4$ substituents have the same meanings as the corresponding substituents on the novel triazines of formula I described hereinabove and wherein the substituents on the phenyl ring are as follows:

$R_5$, $R_6$, $R_7$, $R_8$ and $R_9$ may be the same or different and are:
hydrogen,
halo,
loweralkyl,
haloloweralkyl,
nitro,
loweralkoxy,
hydroxy, arylloweralkoxy,
acyloxy,
cyano,
haloloweralkoxy or
loweralkylsulfonyl.

Amidinourea starting materials which can be used to prepare a more preferred group of triazine derivatives are those wherein $R_3$ and $R_4$ are hydrogen,
hydroxy,
loweralkyl,
loweralkoxy,
haloloweralkyl, or
aralkyl; or
$R_3$ and $R_4$ together may form with the nitrogen to which they are attached a 5–7 atom ring which may include 0–2 hetero atoms of N, O or S.

An even more preferred group of starting materials include those there:

$R_5$, $R_6$, $R_7$, $R_8$ and $R_9$ are hydrogen,
halo,
loweralkyl,
haloloweralkyl,
nitro,
hydroxy or
loweralkoxy.

A still more preferred group of starting materials include those where:

$R_5$ and $R_9$ are each hydrogen,
halo,
loweralkyl,
nitro or
loweralkoxy;
$R_6$, $R_7$ and $R_8$ are each hydrogen,
hydroxy,
halo,
loweralkyl, or
loweralkoxy; and
$R_3$ and $R_4$ are each hydrogen,
loweralkyl,
hydroxy,
loweralkoxy,
haloloweralkyl, or
acyl.

The most preferred starting materials are those where:

$R_5$ is methyl,
ethyl,
chloro or
bromo;
$R_6$ is hydrogen;
$R_7$ is hydrogen;
$R_8$ is hydrogen;
$R_9$ is methyl,
ethyl,
nitro,
methoxy,
ethoxy,
chloro,
bromo or
fluoro; and
$R_3$ and $R_4$ are each hydrogen alkyl of $C_1$ to $C_4$,
hydroxy,
methoxy,
ethoxy,
chloromethyl,
trifluoromethyl 2,3,2-trifluoroethyl, or
acetyl.

A special embodiment of this invention comprises compounds where the starting materials have:
X is oxygen; and the phenyl group has
$R_5$, $R_9$ loweralkyl, loweralkoxy or halo substitution independently of each other;
and one of $R_3$ and $R_4$ is hydrogen and the other is loweralkyl,
haloloweralkyl,
hydroxy,
loweralkoxy or
acyl.

Throughout this disclosure, where reference is made to amidinoureas or triazinones, it will be understood that the same applies also to the corresponding amidinothioureas or triazinthiones; and that in all instances the triazinones and thiones are the 1,2-dihydro-1,3,5-triazin-2-ones and 1,2-dihydro-1,2,5-triazin-2-thiones whatever the abbreviated form of nomenclature that may be used.

The preparation of s-triazinone compounds according to this invention is achieved in general by reacting an appropriate amidinourea or amidinothiourea starting material with an activated form of an acid amide or ortho ester or acyl derivative such as a Vilsmeir reagent which will bring about acylation and ring closure of the amidinourea or thiourea to give the corresponding s-triazinone or thiones of the type described above. The reaction can be carried out by simply combining the reactants in a suitable solvent at room temperature with stirring. The reaction time can be shortened by heating the reaction mixture or by using elevated pressure or both. The solvent selected should have a relatively high boiling point and low vapor pressure in order to permit the reaction mixture to be heated above 100° C. Dimethylformamide is a convenient solvent to use particularly where the cyclizing reagent is a dimethylformamide derivative though other organic solvents can also be used. The solvents that can be used include saturated and unsaturated hydrocarbons, aromatic solvents, alcohols such as methanol and ethanol, halogenated hydrocarbons such as chloroform, carbon tetrachloride, ethylene chloride, or others such as methyl acetate, ethyl acetate, acetonitrile, acetone, ether, acetamide, tetrahydrofuran and the like. Suitable mixtures of solvents can also be used. The reaction is preferably carried out under substantially anhydrous conditions though the presence of water can be tolerated. If small amounts of water are present, the effect can be offset by using an excess of the cyclizing reagent.

The conversion of most amidinoureas to the corresponding s-triazine derivative can be achieved in about 20 minutes or less at temperatures in the order of 100° to 120° C. Higher or lower temperatures can be used if desired and the reaction can be carried out at room temperature. In those cases where the reaction proceeds slowly it can be shortened by heat or pressure or both. The reaction can be readily carried out at atmospheric pressure though if desired, the reaction can be facilitated by increased pressure. A convenient method for carrying out the cyclizing reaction is by heating the reaction mixture in a sealed vessel and allowing the reaction to proceed under autogenous pressure. An alternative process is by refluxing the reaction mixture for about an hour or more. Where the starting material utilized is the acid addition salt of an appropriate amidinourea the reaction proceeds almost instantaneously at room temperature in most cases. However, if the amidinourea starting material is used in the form of the free base, a small amount of acid preferably a mineral acid particularly hydrochloric acid is desirably added to the reaction mixture. As mentioned above, the reaction is suitably carried out in the presence of a solvent. The choice of solvent will in general depend upon the cyclizing reagent used. When using a DMF reagent, the preferred solvents are DMF, DMF-dimethylsulfate complex, or a complex with an alcohol (preferably iso-propanol) the particular alcohol will depend on the solubility of the product obtained.

In most cases the cyclized end product can be recovered by filtering after direct crystallization from the reaction mixture particularly where the solvent has been chosen to facilitate recovery of the end product. Where the product does not readily crystallize, the novel s-triazinone derivatives can be conveniently isolated in the pure form by solvent extraction using any of the usual organic solvents which are not miscible with water such as the hydrocarbons, for example, hexane; the chlorinated hydrocarbons, for example, chloroform or carbon tetrafluoride; the aromatic solvents such as benzene, xylene, toluene, o-chloro-toluene and the like; ethers such as dioxane; ketones such as 2 pentanone etc. The s-triazinone product is extracted into the solvent layer generally after stripping the solvent or concentrating the reaction mixture then shaking with an extracting composition of water and solvent and removing the solvent component, leaving the by-product in the aqueous layer. The product is recovered by evaporating off the solvent. If desired, the product can be further purified by recrystallizing from a suitable organic solvent such as those noted above. The selection of solvent is not critical and generally those solvents which are most readily available will be employed.

The amidinourea starting materials which are derivatized in accordance with the process aspect of this invention are known materials prepared as previously noted by known methods such as described in U.S. Pat. Nos. 4,060,635 and 4,058,557.

The cyclizing reagent employed in the reaction can be any cationic reagent system capable of generating in the reaction mixture a stabilized carbonium ion having the oxidation state of an acid or acid amine, preferably an immonium ion. The preferred reagents are the dialkyl carboxylic acid amide dialkyl acetals such as dialkyl formamide dialkyl acetal preferably dimethyl formamide dimethyl acetal; dialkyl acetamide dialkyl acetals preferably dimethyl acetamide dimethyl acetal; dialkyl propionamide dialkyl acetal preferably dimethyl propionamide dimethyl acetal. Other carboxylic acid amide derivatives can also be used including substituted derivatives. Since the carboxyl carbon is incorporated into the ring the choice of reagent will determine the $R_2$ substitution in the products of formula I above. Thus, in the case of the formamide derivative, $R_2$ is hydrogen and the resulting triazine is unsubstituted in the 6-position; in the case where the acetamide derivative is used as the cyclizing reagent, $R_2$ is methyl and the resulting triazine is substituted in the 6-position, and so on. The preferred substituents are lower alkyl for which the cyclizing reagents used are the lower alkanoic acid amide derivatives. Other substituents within the meaning of $R_2$ are obtained by selection of the correspondingly substituted alkanoic acid amide in preparing the cyclizing reagent.

In general, the preferred cyclizing reagents are the alkanoic acid amide diacetals of the formula:

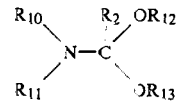

wherein:
$R_2$ is hydrogen or loweralkyl;
and each of $R_{10}$ through $R_{13}$ are loweralkyl or haloloweralkyl.

Other methylidene derivatives that can be used as the cyclizing reagent include the combination of an N,N-disubstituted alkanoic acid amide and any strong alkylating agent preferably a strong methylating agent. Any of the strong alkylating agents known in the art such as methyliodide, methylfluorosulfonate, alkylmethane sulfonates, e.g., methylmethanesulfonate, and alkyl or dialkyl sulfates, e.g., dimethylsulfate can be suitably employed though dimethylsulfate is preferred owing to its ready availability. A preferred cyclizing reagent is a DMF-dimethylsulfate complex particularly DMF-methane methyl-sulfonate or DMF-methylbenzenesulfonate.

Reagents of the type shown in formula IV above are staple products which are commercially available or can be prepared in advance. In carrying out the cyclizing reaction, the cyclizing reagent is preferably used in slight excess of the amount required as the stoichiometric equivalent of the amidinourea or amidinothiourea starting material. The preferred reagent is dimethyl formamide dimethylacetal in which case dimethylformamide is a convenient solvent. A particularly preferred reagent system is a mixture of dimethyl formamide and dimethyl sulfate utilizing excess dimethyl formamide as a solvent. Such reagent systems employing dimethyl sulfate are prepared as necessary for the cyclization or can be formed in situ in the reaction mixture by adding the reagent components to the reaction vessel in a suitable solvent or solvent mixture. When carrying out the cyclizing reaction with a reagent of the type shown in formula IV, it is preferred to use as starting material an acid addition salt of the amidinourea or amidinothiourea or alternatively, if the free base is used, then an acid preferably a mineral acid such as hydrochloric acid can be added to the reaction mixture. When a reagent system comprising an alkanoic acid amide and a strong alkylating agent is employed, the reagent is itself acidic and the reaction proceeds readily with the free base as starting material. In such instances it may be advantageous to add a proton scavenging solvent such as a tertiary amine, e.g., triethylamine or cyclic amines such as pyridine. Other miscible solvents can be used along with the preferred amines e.g., solvents such as triethanolamine, acrylonitrile, ethanol, etc. though dimethyl formamide is preferred. As in the case of cyclizing with dimethylformamide dimethylacetal the reaction can be carried out at room temperature or at elevated temperatures up to the boiling point of the solvent employed. Preferably, the reaction is carried out at room temperature i.e., at about 18° to 25° C. Elevated pressure may also be used. Suitably, the reaction is carried out by refluxing at the boiling temperature of the solvent. The reaction product is easily recovered from the reaction mixture by solvent extraction as described above. The reaction proceeds nearly quantatively based upon the amidinourea starting material and the product can be recovered in nearly quantitative yield, the product can be further purified by recrystallizing if desired.

Alternatively, some of the triazinones can be prepared by using other cyclizing reagents such as triethyl orthoformate catalyzed with either base or acid though generally such processes are less suitable and conventional cyclizing agents such as phosphonyl chloride and thionyl chloride have been found to be unsuited for cyclizing amidinoureas.

Pharmaceutically acceptable salts of the compounds can be obtained as acid addition salts prepared from the corresponding free base by recrystallizing from a solution of a non-toxic pharmaceutically acceptable organic or inorganic acid including strong Lewis acids. Other salts for example quarternary ammonium salts are prepared by known methods for quaternizing organic nitrogen compounds. The non-toxic acid addition salts that can be conveniently prepared from the novel triazine derivatives of this invention are preferably those prepared from strong acids of low volatility. Among the suitable acids that can be named are the following:
hydrochloric acid,
hydrobromic acid,
sulfuric acid,
nitric acid,
phosphoric acid,
methane sulfonic acid,
benzene sulfonic acid,
toluene sulfonic acid, etc.

The synthesis of the novel amidinourea and amidinothiourea derivatives of this invention is accomplished in accordance with the novel cyclizing method of this invention which in its broad process aspect consists of cyclizing amidinoureas and amidinothioureaas and the like by bridging the terminal nitrogens with a methylidene or substituted methylidene group derived from a suitable derivatizing reagent.

The novel cyclizing reaction can be illustrated schematically as follows:

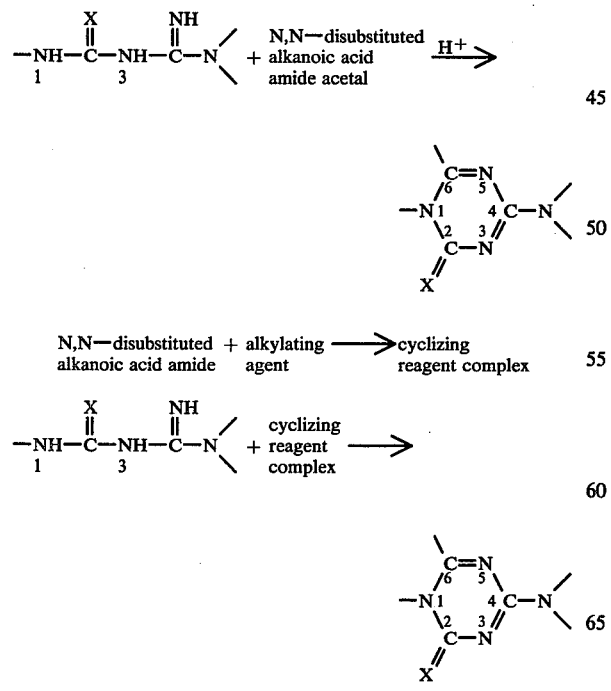

wherein X is sulfur or oxygen indicating that the reaction can employ as starting material either an amidinourea or amidinothiourea. The dangling bonds may be substituted by any appropriate substituent determined by available amidinourea or amidinothiourea starting material.

It will be readily apparent that the dangling bonds on the end product 1,3,5-triazin-2-one or 1,3,5-triazine-2-thione will be substituted by groups corresponding to similar substituents on the starting materials.

In accordance with this invention, the process is particularly useful in preparing compounds of formula I by cyclizing the corresponding starting materials and also to prepare compounds of the type shown in formula I where $R_1$ is an aliphatic group preferably alkyl provided one of $R_3$ and $R_4$ is other than hydrogen.

The numerical designations indicate the nomenclature used herein. It will be readily understood that alternative naming systems for these compounds can be employed.

The novel triazine derivatives prepared in accordance with the method of this invention for derivitizing the corresponding amidinourea or thiourea are those in which the substituent in the one position of the amidinourea or amidinothiourea shown schematically above has an aryl or heterocyclic group, prefereably compounds of the following formula:

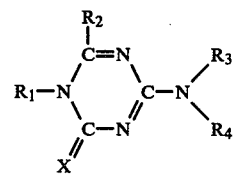

V wherein:
X is oxygen or
  sulfur;
$R_1$ is aryl,
  aralkyl or
  a 5 or 6 membered heterocyclic ring attached directly to the triazine nitrogen or attached through an alkylidene bridge preferably having 1 to 4 carbon atoms;
$R_2$ is hydrogen or
  loweralkyl;
$R_3$ and $R_4$ are each independently selected from the group consisting of hydrogen,
  hyroxyl,
  an aliphatic radical which can be alkyl,
    alkenyl,
    alkynyl,
    cycloalkyl or
    any of said aliphatic radicals wherein one or more hydrogen atoms has been replaced by
      hydroxyl,
      alkoxy,
      phenoxy,
      substituted phenoxy,
      cycloalkyl,
      haloloweralkyl,
      amino,
      loweralkylamino or
      diloweralkylamino,
      phenyl or
      substituted phenyl or a 5 or 6 membered heterocyclic group containing 1 to 3 hetero atoms which may be nitrogen,
oxygen or sulfur,
loweralkoxy,
phenoxy,
substituted phenoxy,
phenyl,
substituted phenyl or
acyl preferably loweralkanoyl; or $R_3$ and $R_4$ taken together with the nitrogen to which they are attached may form a 5 or 6 membered heterocyclic ring containing 1 or 2 additional hetero atoms which may be nitrogen,
oxygen or
sulfur
and the ring may contain 1 or more double bonds; together with their pharmaceutically acceptable salts.

A preferred group of novel triazines prepared by derivetizing amidinoureas are the compounds of the formula:

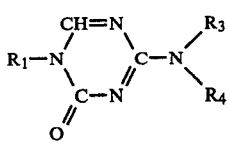

V-a wherein:
$R_1$ is phenyl,
substituted phenyl,
pyridyl,
substituted pyridyl or
phenyl-loweralkyl; and
$R_3$ and $R_4$ are each separately hydrogen,
loweralkyl,
haloloweralkyl,
hydroxy,
alkoxy,
alkoxyloweralkyl, or
loweralkanoyl; and
their non-toxic pharmaceutically acceptable salts.

A particularly preferred group of novel triazinones are the compounds of the formula:

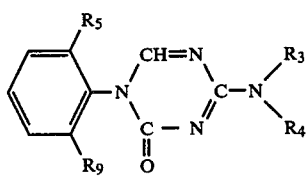

V-b wherein:
the ortho-substituents on the phenyl moiety designated by $R_5$ and $R_9$ are the same or different and are
$C_1$ to $C_4$ alkyl,
bromo,
chloro, or
$C_1$ to $C_4$ alkoxy; and
the $R_3$ and $R_4$ substituents are each hydrogen,
hydroxyl,
loweralkyl,
haloloweralkyl,
loweralkoxy or
loweralkanoyl.

And those compounds of formula V-b wherein one of $R_3$ or $R_4$ is hydrogen are a most preferred group.

Using the general method for cyclizing amidinoureas described above and employing by way of illustration as the starting material any of the amidinoureas in Tables I, Ia and Ib below, there can be obtained the corresponding illustrative triazinone of Tables II, II-a and II-b. The thione analogs and their salts are prepared in the same manner using the corresponding amidinothiourea as starting material. Examples of amidinothioureas starting materials and the corresponding thiones obtained by cyclizing in accordance with the method of this invention are given in Tables III and IV respectively. IV-a, respectively.

TABLE I 1-(2',6'-diethylphenyl)-3-methylamidinourea
1-(2',6'-diethylphenyl)-3-ethylamidinourea
1-(2',6'-diethylphenyl)-3-propylamidinourea
1-(2',6'-diethylphenyl)-3-i-propylamidinourea
1-(2',6'-diethylphenyl)-3-butylamidinourea
1-(2',6'-diethylphenyl)-3-i-butylamidinourea
1-(2',6'-diethylphenyl)-3-pentylamidinourea
1-(2',6'-diethylphenyl)-3-allylamidinourea
1-(2',6'-diethylphenyl)-3-propargylamidinourea
1-(2',6'-diethylphenyl)-3-cyclopropylamidinourea
1-(2',6'-diethylphenyl)-3-methoxyethylamidinourea
1-(2',6'-diethylphenyl)-3-benzyloxyethylamidinourea
1-(2',6'-diethylphenyl)-3-phenethoxyethylamidinourea
1-(2',6'-diethylphenyl)-3-benzylamidinourea
1-(2',6'-diethylphenyl)-3-(N,N-dimethylamidino)urea
1-(2',6'-diethylphenyl)-3-(N,N-diethylamidino)urea
1-(2',6'diethylphenyl)-3-(N,N-tetramethyleneamidino)urea
1-(2',6'-diethylphenyl)-3-(N,N-pentamethyleneamidino)urea
1-(2'-methyl-6'-ethylphenyl)-3-methylamidinourea
1-(2'-methyl-6'-ethylphenyl)-3-ethylamidinourea
1-(2'-methyl-6'-ethylphenyl)-3-propylamidinourea
1-(2'-methyl-6'-ethylphenyl)3-i-propylamidinourea
1-(2'-methyl-6'-ethylphenyl)-3-butylamidinourea
1-(2'-methyl-6'-ethylphenyl)3-i-butylamidinourea
1-(2'-methyl-6'-ethylphenyl)3-t-butylamidinourea
1-(2'-methyl-6'-ethylphenyl)-3-pentylamidinourea
1-(2'-methyl-6'-ethylphenyl)-3-allylamidinourea
1-(2'-methyl-6'-ethylphenyl)-3-propargylamidinourea
1-(2'-methyl-6'-ethylphenyl)-3-cyclopropylamidinourea
1-(2'methyl-6'-ethylphenyl)-3-cyclobutylamidinourea
1-(2'-methyl-6'-ethylphenyl)-3-[N-(3'-cyclopentenyl-)amidino]urea
1-(2'-methyl-6'-ethylphenyl)-3-cyclopropylmethylamidinourea
1-(2'-methyl'6'-ethylphenyl)-3-methoxyethylamidinourea
1-(2'-methyl-6'-ethylphenyl)-3-benzyloxyethylamidinourea
1-(2'-methyl-6'-ethylphenyl)-3-phenethoxyethylamidinourea
1-(2'-methyl-6'-ethylphenyl)-3-benzylamidinourea
1-(2'-methyl-6'-ethylphenyl)-3-(N,N-dimethylamidino)urea
1-(2'-methyl-6'-ethylphenyl)-3-(N,N-diethylamidino)urea
1-(2'-methyl-6'-ethylphenyl)-3-(N,N-tetramethyleneamidino)urea
1-(2'-methyl-6'-ethylphenyl)-3-[N,N(3'-methyl-3'-azapentamethylene)amidino]urea 1-(2'-methyl-6'-ethylphenyl)-3-[N,N-(3'-oxapentamethylene)amidino]urea
1-(2'-methyl-6'-chlorophenyl)-3-methylamidinourea
1-(2'-methyl-6'-chlorophenyl)-3-ethylamidinourea
1-(2'methyl-6'-chlorophenyl)-3-propylamidinourea
1-(2'-methyl-6'-chlorophenyl)3-i-propylamidinourea
1-(2'-methyl-6'-chlorophenyl)-3-butylamidinourea
1-(2'-methyl-6'-chlorophenyl)-3-i-butylamidinourea
1-(2'-methyl-6'-chlorophenyl)-3-t-butylamidinourea
1-(2'-methyl-6'-chlorophenyl)-3-pentylamidinourea
1-(2'-methyl-6'-chlorophenyl)-3-allylamidinourea
1-(2'-methyl-6'-chlorophenyl)-3-propargylamidinourea
1-(2'-methyl-6'-chlorophenyl)-3-cyclobutylamidinourea
1-(2'-methyl-6'-chlorophenyl)-3-cyclohexylamidinourea
1-(2'-methyl-6'-chlorophenyl)-3-benzylamidinourea
1-(2'-methyl-6'-chlorophenyl)-3-methoxyethylamidinourea
1-(2'-methyl-6'-chlorophenyl)-3-benzyloxyethylamidinourea
1-(2'-methyl-6'-chlorophenyl)-3-phenethoxyethylamidinourea
1-(2'-methyl-6'-chlorophenyl)-3-(N,N-diethylamidino)urea
1-(2'-methyl-6'-chlorophenyl)-3-(N,N-diethylamidino)urea
1-(2'-methyl-6'-chlorophenyl)-3-(N,N-pentamethyleneamidino)urea
1-(2'-methyl-6'-bromophenyl)-3-methylamidinourea
1-(2'-methyl-6'-bromophenyl)-3-ethylamidinourea
1-(2'-methyl-6'-bromophenyl)-3-propylamidinourea
1-(2'-methyl-6'-bromophenyl)-3-i-propylamidinourea
1-(2'-methyl-6'-bromophenyl)-3-butylamidinourea
1-(2'-methyl-6'-bromophenyl)-3-t-butylamidinourea
1-(2'-methyl-6'-bromophenyl)-3-pentylamidinourea
1-(2'-methyl-6'-bromophenyl)-3-hexylamidinourea
1-(2'-methyl-6'-bromophenyl)-3-propargylamidinourea
1-(2'-methyl-6'-bromophenyl)-3-allylamidinourea
1-(2'-methyl-6'-bromophenyl)-3-methoxyethylamidinourea
1-(2'-methyl-6'-bromophenyl)-3-benzyloxyethylamidinourea
1-(2'-methyl-6'-bromophenyl)-3-phenethoxyethylamidinourea
1-(2'-methyl-6'-bromophenyl)-3-(N,N-dimethylamidino)urea
1-(2'-methyl-6'-bromophenyl)-3-(N,N-diethylamidino)urea
1-(2'-methyl-6'-bromophenyl)-3-(N-methyl-N-ethylamidino)urea
1-(2'-methyl-6'-bromophenyl)-3-(N,N-tetramethyleneamidino)urea
1-(2'-methyl-6'-bromophenyl)-3-(N,N-pentamethyleneamidino)urea
1-(2'-methyl-6'-bromophenyl)-3-(N,N-hexamethyleneamidino)urea
1-(2'-ethyl-6'-chlorophenyl)-3-methylamidinourea
1-(2'-ethyl-6'-chlorophenyl)-3-ethylamidinourea
1-(2'-ethyl-6'-chlorophenyl)-3-propylamidinourea
1-(2'-ethyl-6'-chlorophenyl)-3-butylamidinourea
1-(2'-ethyl-6'-chlorophenyl)-3-i-butylamidinourea
1-(2'-ethyl-6'-chlorophenyl)-3-pentylamidinourea
1-(2'-ethyl-6'-chlorophenyl)-3-allylamidinourea
1-(2'-ethyl-6'-chlorophenyl)-3-propargylamidinourea
1-(2'-ethyl-6'-chlorophenyl)-3-methoxyethylamidinourea
1-(2'-ethyl-6'-chlorophenyl)-3-benzyloxyethylamidinourea
1-(2'-ethyl-6'-chlorophenyl)-3-(N,N-dimethylamidino)urea
1-(2'-ethyl-6'-chlorophenyl)-3-(N,N-diethylamidino)urea
1-(2'-ethyl-6'-chlorophenyl)-3-(N,N-tetramethyleneamidino)urea
1-(2'-methyl-6'-fluorophenyl)-3-methylamidinourea
1-(2',6'-dimethyl-4'-hydroxyphenyl)-3-methylamidinourea
1-(2',6'-diethyl-4'-hydroxyphenyl)-3-methylamidinourea
1-(2'-methyl-6'-chloro-4'-hydroxyphenyl)-3-methylamidinourea
1-(2'-methyl-6'-bromo-4'-hydroxyphenyl)-3-methylamidinourea
1-(2'-methyl-6'-fluoro-4'-hydroxyphenyl)-3-methylamidinourea
1-(2'-methyl-6'-ethyl-4'-hydroxyphenyl)-3-methylamidinourea
1-(2'-ethyl-6'-chloro-4'-hydroxyphenyl)-3-methylamidinourea
1-(2'-ethyl-6'bromo-4'-hydroxyphenyl)-3-methylamidinourea
1-(2'-ethyl-6'-fluoro-4'-hydroxyphenyl)-3-methylamidinourea
1-(2',6'-dimethyl-4'-aminophenyl)-3-methylamidinourea
1-(2',6'-diethyl-4'-aminophenyl)-3-methylamidinourea
1-(2'-methyl-6'-ethyl-4'-aminophenyl)-3-methylamidinourea
1-(2'-methyl-6'-chloro-4'-aminophenyl)-3-methylamidinourea
1-(2'-methyl-6'-bromo-4'-aminophenyl)-3-methylamidinourea
1-(2'-methyl-6'-fluoro-4'-aminophenyl)-3-methylamidinourea
1-(2'-ethyl-6'-chloro-4'-aminophenyl)-3-methylamidinourea
1-(2'-ethyl-6'-bromo-4'-aminophenyl)-3-methylamidinourea
1-(2'-ethyl-6'-fluoro-4'-aminophenyl)-3-methylamidinourea
1-(2',6'-dimethyl-4'-acetylamino)-3-methylamidinourea
1-(2',6'-diethyl-4'-acetylamino)-3-methylamidinourea
1-(2'-methyl-6'-ethyl-4'-acetylamino)-3-methylamidinourea
1-(2'-methyl-6'-chloro-4'-acetylamino)-3-methylamidinourea
1-(2'-methyl-6'-bromo-4'-acetylamino)-3-methylamidinourea
1-(2'-methyl-6'-fluoro-4'-acetylamino)-3-methylamidinourea
1-(2'-ethyl-6'-chloro-4'-acetylamino)-3-methylamidinourea
1-(2'-ethyl-6'-bromo-4'-acetylamino)-3-methylamidinourea
1-(2'-ethyl-6'-fluoro-4'-acetylamino)-3-methylamidinourea
1-(2',6'-diethyl-4'-nitrophenyl)-3-methylamidinourea hydrochloride
1-(4'amino-2',6'-diethylphenyl)-3-methylamidinourea dihydrochloride
1-(2',6'-dimethyl-4'-aminophenyl-3-methylamidinourea hydrochloride
1-(2',6'-dimethylphenyl)-3-(N,N-diethylamidino)urea hydrochloride
1-(2',6'-dimethylphenyl)-3-(N-ethyl-N-methylamidino)urea hydrochloride 1-(2',6'-dimethylphenyl)-3-(N-methyl-N-propylamidino)urea hydrochloride
1-(2',6'-dimethylphenyl)-3-(N-methyl-N-butylamidino)urea hydrochloride
1-(2',6'-dimethylphenyl)-3-(N,N-dipropylamidino)urea hydrochloride
1-(2',6'-dimethylphenyl)-3-(N-ethyl-N-propylamidino)urea hydrochloride
1-(2',6'-dimethylphenyl)-3-(N-methyl-N-benzyloxypropylamidino)urea hydrochloride
1-(2',6'-dimethylphenyl)-3-(N-methyl-N-phenethoxyethylamidino)urea hydrochloride
1-(2',6'-dimethylphenyl)-3-(N-methyl-N-benzyloxyethylamidino)urea hydrochloride
1-(2',6'-dimethylphenyl)-3-(N,N-tetramethyleneamidino)urea hydrochloride
1-(2',6'-dimethylphenyl)-3-(N,N-pentamethyleneamidino)urea hydrochloride
1-(2',6'-dimethylphenyl)-3-(N,N-hexamethyleneamidino)urea hydrochloride
1-(2',6'-dimethylphenyl)-3-[N,N-(3'-oxapentamethylene)amidino]urea hydrochloride
1-(2',6'-dimethylphenyl)-3-[N,N-(3'-methyl-3'-azapentamethylene)-amidino]urea hydrochloride
1-(2',6'-dimethylphenyl)-3-[N,N-(3'-methyl-3'-azahexemethylene)-amidino]urea hydrochloride
1-(2',6'-dimethylphenyl)-3-[N,N-(3'-thiapentamethylene)-amidino]urea hydrochloride
1-(2',6'-dimethylphenyl)-3-[N,N-(2'-thiatetramethylene)-amidino]urea hydrochloride
1-(2',6'-dimethylphenyl)-3-[N-(2'-butenyl)-amidino]urea hydrochloride
1-(2',6'-dimethylphenyl)-3-[N-(2'-butynyl)-amidino]urea hydrochloride
1-(2',6'-dimethylphenyl)-3-[N-(3'-butynyl)-amidino]urea hydrochloride
1-(2',6'-dimethylphenyl)-3-(N-methyl-N-allylamidino)-urea hydrochloride
1-(2',6'-dimethylphenyl)-3-(N-methyl-N-propargylamidino)-urea hydrochloride
1-(2',6'-dimethylphenyl)-3-(N-methyl-N-cyclopropylamidino)-urea hydrochloride
1-(2',6'-dimethylphenyl)-3-(N-methylamidino)urea
1-(2',6'-dimethylphenyl)-3-(N,N-dimethylamidino)urea
1-(2'-methyl-6'-methoxyphenyl)-3-(N-methylamidino)urea
1-(2'-methylphenyl)-3-(N-methylamidino)urea
1-(2',4',6'-trimethylphenyl)-3-(N-methylamidino)urea
1-(2'-methyl-4'-bromo-6'-chlorophenyl)-3-(N-methylamidino)urea
1-(2'-chloro-6'-fluorophenyl)-3-(N-methylamidino)urea
1-(2',5'-dichlorophenyl)-3-(N-methylamidino)urea
1-(2'-chloro-6'-bromophenyl)-3-(N-methylamidino)urea
1-(2'-chloro-5'-bromophenyl)-3-(N-methylamidino)urea
1-(2'-chloro-5'-fluorophenyl)-3-(N-methylamidino)urea
1-(2'-fluoro-5'-chlorophenyl)-3-(N-methylamidino)urea
1-(2'-fluoro-5'-bromophenyl)-3-(N-methylamidino)urea
1-(2',4',6'-triethylphenyl)-3-(N-methylamidino)urea
1-(2',4'-dimethyl-6'-ethylphenyl)-3-(N-methylamidino)urea
1-(2',6'-dimethyl-4'-ethylphenyl)-3-(N-methylamidino)urea
1-(2'-ethylphenyl)-3-(N-methylamidino)urea
1-(2'-ethyl-4'-bromo-6'-chlorophenyl)-3-(N-methylamidino)urea
1-(2'-ethyl-6'-methoxyphenyl)-3-(N-methylamidino)urea
1-(2'-methyl-6'-ethoxyphenyl)-3-(N-methylamidino)urea
1-(2',6'-dimethylphenyl)-3-(N-ethylamidino)urea
1-(2',6'-dimethylphenyl)-3-(N-propylamidino)urea
1-(2',6'-dimethylphenyl)-3-(N-i-propylamidino)urea
1-(2',6'-dimethylphenyl)-3-(N-butylamidino)urea
1-(2',6'-dimethylphenyl)-3-(N-i-butylamidino)urea
1-(2',6'-dimethylphenyl)-3-(N-sec-butylamidino)urea
1-(2',6'-dimethylphenyl)-3-(N-t-butylamidino)urea
1-(2',6'-dimethylphenyl)-3-(N-pentylamidino)urea
1-(2',6'-dimethylphenyl)-3-(N-hexylamidino)urea
1-(2',6'-dimethylphenyl)-3-(N-heptylamidino)urea
1-(2',6'-dimethylphenyl)-3-(N-cyclopropylamidino)urea
1-(2',6'-dimethylphenyl)-3-(N-cyclobutylamidino)urea
1-(2',6'-dimethylphenyl)-3-(N-cyclopentylamidino)urea
1-(2',6'-dimethylphenyl)-3-(N-cyclohexylamidino)urea
1-(2',6'-dimethylphenyl)-3-(N-phenylamidino)urea
1-(2',6'-dimethylphenyl)-3-(N-benzylamidino)urea
1-(2',6'-dimethylphenyl)-3-(N-phenethylamidino)urea
1-(2',6'-dimethylphenyl)-3-(N-methyl-N-benzylamidino)urea
1-(2',6'-dimethylphenyl)-3-(N,N-dibenzylamidino)urea
1-(2'-methyl-6'-chlorophenyl)-3-amidinourea
1-(2'-methyl-6'-fluorophenyl)-3-amidinourea
1-(2'-methyl-6'-bromophenyl)-3-amidinourea
1-(2'-methyl-6'-iodophenyl)-3-amidinourea
1-(2'-methyl-6'-methoxyphenyl)-3-amidinourea
1-(2'-methyl-6'-ethoxyphenyl)-3-amidinourea
1-(2'-methyl-6'-ethylphenyl)-3-amidinourea
1-(2'-methyl-6'-propylphenyl)-3-amidinourea
1-(2'-methyl-6'-i-propylphenyl)-3-amidinourea
1-(2'-methyl-6'-butylphenyl)-3-amidinourea
1-(2'-methyl-6'-cyano phenyl)-3-amidinourea
1-(2'methyl-6'-trifluoromethylphenyl)-3-amidinourea
1-(2'-methyl-6'-nitrophenyl)-3-amidinourea
1-(2'-methyl-6'-methylsulfonylphenyl)-3-amidinourea
1-(2'-ethyl-6'-chlorophenyl)-3-amidinourea
1-(2'-ethyl-6'-fluorophenyl)-3-amidinourea
1-(2'-ethyl-6'-bromophenyl)-3-amidinourea
1-(2'-ethyl-6'-methoxyphenyl)-3-amidinourea
1-(2'-ethyl-6'-ethoxyphenyl)-3-amidinourea
1-(2',6'-diethylphenyl)-3-amidinourea
1-(2'-ethyl-6'-propylphenyl)-3-amidinourea
1-(2'-ethyl-6'-trifluoromethylphenyl)-3-amidinourea
1-(2'-propyl-6'-chlorophenyl)-3-amidinourea
1-(2'-propyl-6'-bromophenyl)-3-amidinourea
1-(2'-propyl-6'-methoxyphenyl)-3-amidinourea
1-(2'-propyl-6'-ethoxyphenyl)-3-amidinourea
1-(2',6'-dipropylphenyl)-3-amidinourea
1-(2'-i-propyl-6'-chlorophenyl)-3-amidinourea
1-(2',6'-dichlorophenyl)-3-amidinourea
1-(2'-chloro-3'-methylphenyl)-3-amidinourea
1-(2'-chloro-4'-methylphenyl)-3-amidinourea
1-(2'-chloro-5'-methylphenyl)-3-amidinourea
1-(2'-chloro-5'-trifluoromethylphenyl)-3-amidinourea
1-(2'-chloro-6'-fluorophenyl)-3-amidinourea
1-(2',6'-difluorophenyl)-3-amidinourea
1-(2'-propylphenyl)-3-amidinourea
1-(4'-trifluoromethylphenyl)-3-amidinourea
1-(3',4'-dimethoxyphenyl)-3-amidinourea
1-(3',4',5'-trimethoxyphenyl)-3-amidinourea
1-(3',4'-diethoxyphenyl)-3-amidinourea
1-(2',4'-dimethylphenyl)-3-amidinourea
1-(2',4'-diethylphenyl)-3-amidinourea
1-(2'-methyl-4'-ethylphenyl)-3-amidinourea
1-(2'-methyl-4'-chlorophenyl)-3-amidinourea
1-(2'-ethyl-4'-chlorophenyl)-3-amidinourea 1-(2',4',6'-trimethylphenyl)-3-amidinourea
1-(2',4'-dimethyl-6'-ethylphenyl)-3-amidinourea
1-(2',4'-dimethyl-6'-trifluoromethylphenyl)-3-amidinourea
1-(2',4'-dimethyl-6'-nitrophenyl)-3-amidinourea
1-(2',4'-dimethyl-6'-methoxyphenyl)-3-amidinourea
1-(2',6'-dimethyl-4'-chlorophenyl)-3-amidinourea
1-(2',6'-dimethyl-4'-bromophenyl)-3-amidinourea
1-(2',6'-dimethyl-4'-methoxyphenyl)-3-amidinourea
1-(2'-methyl-4',6'-dichlorophenyl)-3-amidinourea
1-(2'-methyl-4',6'-difluorophenyl)-3-amidinourea
1-(2'-methyl-4'-fluoro-6'-bromophenyl)-3-amidinourea
1-(2'-methyl-4'-chloro-6'-trifluoromethylphenyl)-3-amidinourea
1-(2'-methyl-4'-trifluoromethyl-6'-chlorophenyl)-3-amidinourea
1-(2'-ethyl-4',6'-dichlorophenyl)-3-amidinourea
1-(2',6'-diethyl-4'-chlorophenyl)-3-amidinourea
1-(2',6'-diethyl-4'-bromophenyl)-3-amidinourea
1-(2',6'-diethyl-4'-fluorophenyl)-3-amidinourea
1-(2'-chloro-6'-methylphenyl)-3-amidinourea
1-(2',6'-dimethylphenyl)-3-amidinourea
1-(2',6'-diethylphenyl)-3-amidinourea
1-(2'-methyl-6'-methoxyphenyl)-3-amidinourea
1-(2'-methyl-6'-chlorophenyl)-3-amidinourea
1-(2'-methylphenyl)-3-amidinourea
1-(2'-chloro-6'-fluorophenyl)-3-amidinourea
1-(2'-methyl-6'-ethylphenyl)-3-amidinourea
1-(2',4',6'-trimethylphenyl)-3-amidinourea
1-(2'-methyl-6'-methoxyphenyl)-3-(N-methylamidino)urea
1-(2'-methylphenyl)-3-(N-methylamidino)urea
1-(2',4',6'-trimethylphenyl)-3-(N-methylamidino)urea
1-(2'-methyl-4'-bromo-6'-chlorophenyl)-3-(N-methylamidino)urea
1-(2'-chloro-6'-fluorophenyl)-3-(N-methylamidino)urea
1-(2',5'-dichlorophenyl)-3-(N-methylamidino)urea
1-(2'-chloro-6'-bromophenyl)-3-(N-methylamidino)urea
1-(2'-chloro-5'-bromophenyl)-3-(N-methylamidino)urea
1-(2'-chloro-5'-fluorophenyl)-3-(N-methylamidino)urea
1-(2'-fluoro-5'-chlorophenyl)-3-N-methylamidino)urea
1-(2'-fluoro-5'-bromophenyl)-3-(N-methylamidino)urea
1-(2',4',6'-triethylphenyl)-3-(N-methylamidino)urea
1-(2',4'-dimethyl-6'-ethylphenyl)-3-(N-methylamidino)urea
1-(2',6'-dimethyl-4'-ethylphenyl)-3-(N-methylamidino)urea
1-(2'-ethylphenyl)-3-(N-methylamidino)urea
1-(2'-ethyl-4'-bromo-6'-chlorophenyl)-3-(N-methylamidino)urea
1-(2'ethyl-6'-methoxyphenyl)-3-(N-methylamidino)urea
1-(2'methyl-6'-ethoxyphenyl)-3-(N-methylamidino)urea
1-(2',6'-dimethylphenyl)-3-[N-(2',6-dimethylphenyl)amidino]urea
1-(2',6'-dimethyllphenyl)-3-[N-(2'-methylpheynl)amidino]yrea
1-(2',6'-dimethylphenyl)-3-[N-(2',6'-diethylphenyl)amidino]urea
1-(2',6'-dimethylphenyl)-3-[N-(2'methyl-6'-chlorophenyl)amidino]urea
1-(2',6'-dimethylphenyl)-3-[N-(2',4',6'-trimethylphenyl)amidino]urea

TABLE II 1-(2',6'-diethylphenyl)-4-methylamino-1,2-dihydro-1,3,5-triazin-2-one
1-(2'6'-diethylphenyl)-4-ethylamino-1,2-dihydro-1,3,5-triazin-2-one
1-(2',6'-diethylphenyl)-4-propylamino-1,2-dihydro-1,3,5-triazin-2-one
1-(2',6'-diethylphenyl)-4-i-propylamino-1,2-dihydro-1,3,5-triazin-2-one
1-(2',6'-diethylphenyl)-4-butylamino-1,2-dihydro-1,3,5-triazin-2-one
1-(2',6'-diethylphenyl)-4-i-butylamino-1,2-dihydro-1,3,5-triazin-2-one
1-(2',6'-diethylphenyl)-4-pentylamino-1,2-dihydro-1,3,5-triazin-2-one
1-(2',6'-diethylphenyl)-4-allylamino-1,2-dihydro-1,3,5-triazin-2-one
1-(2'6'-diethylphenyl)-4-propargylamino-1,2-dihydro-1,3,5-triazin-2-one
1-(2',6'-diethylphenyl)-4-cyclopropylamino-1,2-dihydro-1,3,5-triazin-2-one
1-(2',6'-diethylphenyl)-4-methoxyethylamino-1,2-dihydro-1,3,5-triazin-2-one
1-(2',6'-diethylphenyl)-4-benzyloxyethylamino-1,2-dihydro-1,3,5-triazin-2-one
1-(2',6'-diethylphenyl)-4-phenethoxyethylamino-1,2-dihydro-1,3,5-triazin-2-one
1-(2',6'-diethylphenyl)-4-benzylamino-1,2-dihydro-1,3,5-triazin-2-one
1-(2',6'-diethylphenyl)-4-(N,N-dimethylamino)-1,2-dihydro-1,3,5-triazin-2-one
1-(2',6'-diethylphenyl)-4-(N,N-diethylamino)-1,2-dihydro-1,3,5-triazin-2-one
1-(2',6'-diethylphenyl)-4-(N-pyrrolidinyl)-1,2-dihydro-1,3,5-triazin-2-one
1-(2',6'-diethylphenyl)-4-(N-piperidyl)-1,2-dihydro-1,3,5-triazin-2-one
1-(2'-methyl-6'-ethyl-phenyl)-4-methylamino-1,2-dihydro-1,3,5-triazin-2-one
1-(2'-methyl-6'-ethyl-phenyl)-4-ethylamino-1,2-dihydro-1,3,5-triazin-2-one
1-(2'-methyl-6'-ethyl-phenyl)-4-propylamino-1,2-dihydro-1,3,5-triazin-2-one
1-(2'-methyl-6'-ethyl-phenyl)-4-i-propylamino-1,2-dihydro-1,3,5-triazin-2-one
1-(2'-methyl-6'ethyl-phenyl)-4-butylamino-1,2-dihydro-1,3,5-triazin-2-one
1-(2'methyl-6'ethyl-phenyl)-4-i-butylamino-1,2-dihydro-1,3,5-triazin-2-one
1-(2'-methyl-6'-ethyl-phenyl)-4-t-butylamino-1,2-dihydro-1,3,5-triazin-2-one
1-(2'-methyl-6'-ethyl-phenyl)-4-pentylamino-1,2-dihydro-1,3,5-triazin-2-one
1-(2'methyl-6'ethyl-phenyl)-4-allylamino-1,2-dihydro-1,3,5-triazin-2-one
1-(2'methyl-6'-ethyl-phenyl)-4-propargylamino-1,2-dihydro-1,3,5-triazin-2-one
1-(2'-methyl-6'-ethylphenyl)-4-cyclopropylamino-1,2-dihydro-1,3,5-triazin-2-one
1-(2'-methyl-6'-ethyl-phenyl)-4-cyclobutylamino-1,2-dihydro-1,3,5-triazin-2-one
1-(2'-methyl-6'-ethyl-phenyl)-4-cyclopenten-3-yl-amino-1,3,5-triazin-2-one
1-(2'methyl-6'ethyl-phenyl)-4-cyclopropylmethylamino-1,2-dihydro-1,3,5-triazin-2-one
1-(2'methyl-6'-ethyl-phenyl)-4-methoxyethylamino-1,2-dihydro-1,3,5-triazin-2-one
1-(2'-methyl-6'-ethyl-phenyl)-4-benzyloxyethylamino-1,2-dihydro-1,3,5-triazin-2-one
1-(2'methyl-6'-ethyl-phenyl)-4-phenethoxyethylamino-1,2-dihydro-1,3,5-triazin-2-one
1-(2'methyl-6'-ethyl-phenyl)-4-benzylamino-1,2-dihydro-1,3,5-triazin-2-one 1-(2'methyl-6'-ethyl-phenyl)-4-(N,N-dimethylamino-)-1,2-dihydro-1,3,5-triazin-2-one
1-(2'methyl-6'-ethyl-phenyl)-4-(N,N-diethylamino)-1,2-dihydro-1,3,5-triazin-2-one
1-(2'methyl-6-ethyl-phenyl)-4-(N-pyrrolidinyl)-1,2-dihydro-1,3,5-triazin-2-one
1-(2'methyl-6'-ethyl-phenyl)-4-[3-(N-methyl-piperidyl)]-1,2-dihydro-1,3,5-triazin-2-one
1-(2'-methyl-6'-chlorophenyl)-4-methylamino-1,2-dihydro-1,3,5-triazin-2-one
1-(2'methyl-6'-ethylphenyl)-4-(N-morpholinyl)-1,2-dihydro-1,3,5-triazin-2-one
1-(2'-methyl-6'-chlorophenyl)-4-ethylamino-1,2-dihydro-1,3,5-triazin-2-one
1-(2'-methyl-6'-chlorophenyl)-4-propylamino-1,2-dihydro-1,3,5-triazin-2-one
1-(2'-methyl-6'-chlorophenyl)-4-i-propylamino-1,2-dihydro-1,3,5-triazin-2-one
1-(2'-methyl-6'-chlorophenyl)-4-butylamino-1,2-dihydro-1,3,5-triazin-2-one
1-(2'-methyl-6'-chlorophenyl)-4-i-butylamino-1,2-dihydro-1,3,5-triazin-2-one
1-(2'-methyl-6'-chlorophenyl)-4-t-butylamino-1,2-dihydro-1,3,5-triazin-2-one
1-(2'-methyl-6'-chlorophenyl)-4-pentylamino-1,2-dihydro-1,3,5-triazin-2-one
1-(2'-methyl-6'-chlorophenyl)-4-pentylamino-1,2-dihydro-1,3,5-triazin-2-one
1-(2'-methyl-6'-chlorophenyl)-4-propargylamino-1,2-dihydro-1,3,5-triazin-2-one
1-(2'-methyl-6'-chlorophenyl)-4-cyclobutylamino-1,2-dihydro-1,3,5-triazin-2-one
1-(2'-methyl-6'-chlorophenyl)-4-cyclohexylamino-1,2-dihydro-1,3,5-triazin-2-one
1-(2'-methyl-6'-chlorophenyl)-4-benzylamino-1,2-dihydro-1,3,5-triazin-2-one
1-(2'-methyl-6'-chlorophenyl)-4-methoxyethylamino-1,2-dihydro-1,3,5-triazin-2-one
1-(2'-methyl-6'-chlorophenyl)-4-benzyloxyethylamino-1,2-dihydro-1,3,5-triazin-2-one
1-(2'-methyl-6'-chlorophenyl)-4-phenethoxyethylamino-1,2-dihydro-1,3,5-triazin-2-one
1-(2'-methyl-6'-chlorophenyl)-4-(N,N-diethylamino)-1,2-dihydro-1,3,5-triazin-2-one
1-(2'-methyl-6'-chlorophenyl)-4-(N-piperidinyl)-1,2-dihydro-1,3,5-triazin-2-one
1-(2'-methyl-6'-bromophenyl)-4-methylamino-1,2-dihydro-1,3,5-triazin-2-one
1-(2'-methyl-6'-bromophenyl)-4-ethylamino-1,2-dihydro-1,3,5-triazin-2-one
1-(2'-methyl-6'-bromophenyl-4-propylamino-1,2-dihydro-1,3,5-triazin-2-one
1-(2'-methyl-6'-bromophenyl)-4-i-propylamino-1,2-dihydro-1,3,5-triazin-2-one
1-(2'-methyl-6'-bromophenyl)-4-butylamino-1,2-dihydro-1,3,5-triazin-2-one
1-(2'-methyl-6'-bromophenyl)-4-t-butylamino-1,2-dihydro-1,3,5-triazin-2-one
1-(2'-methyl-6'-bromophenyl)-4-pentylamino-1,2-dihydro-1,3,5-triazin-2-one
1-(2'-methyl-6'-bromophenyl)-4-hexylamino-1,2-dihydro-1,3,5-triazin-2-one
1-(2-methyl-6'-bromophenyl)-4-propargylamino-1,2-dihydro-1,3,5-triazin-2-one
1-(2'-methyl-6'-bromophenyl)-4-allylamino-1,2-dihydro-1,3,5-triazin-2-one
1-(2'-methyl-6'-bromophenyl)-4-methoxyethylamino-1,2-dihydro-1,3,5-triazin-2-one
1-(2'-methyl-6'-bromophenyl)-4-benzyloxyethylamino-1,2-dihydro-1,3,5-triazin-2-one
1-(2'-methyl-6'-bromophenyl)-4-phenethoxyethylamino-1,2-dihydro-1,3,5-triazin-2-one
1-(2'-methyl-6'-bromophenyl)-4-(N,N-dimethylamino)-1,2-dihydro-1,3,5-triazine-2-one
1-(2'-methyl-6'-bromophenyl)-4-(N,N-diethylamino)-1,2-dihydro-1,3,5-triazin-2-one
1-(2'-methyl-6'-bromophenyl)-4-(N-methyl-N-ethylamino)-1,2-dihydro-1,3,5-triazin-2-one
1-(2'-methyl-6'-bromophenyl)-4-(N-pyrrolidyl)-1,2-dihydro-1,3,5-triazin-2-one
1-(2'-methyl-6'-bromophenyl)-4-(N-piperidyl)-1,2-dihydro-1,3,5-triazin-2-one
1-(2'-methyl-bromophenyl)-4-(N-azepinyl)-1,2-dihydro-1,3,5-triazin-2-one
1-(2'-ethyl-6'-chlorophenyl)-4-methylamino-1,2-dihydro-1,3,5-triazin-2-one
1-(2'-ethyl-6'-chlorophenyl)-4-ethylamino-1,2-dihydro-1,3,5-triazin-2-one
1-(2'-ethyl-6'-chlorophenyl)-4-propylamino-1,2-dihydro-1,3,5-triazin-2-one
1-(2'-ethyl-6'-chlorophenyl)-4-butylamino-1,2-dihydro-1,3,5-triazin-2-one
1-(2'-ethyl-6'-chlorophenyl)-4-i-butylamino-1,2-dihydro-1,3,5-triazin-2-one
1-(2'-ethyl-6'-chlorophenyl)-4-pentylamino-1,2-dihydro-1,3,5-triazin-2-one
1-(2'-ethyl-6'-chlorophenyl)-4-allylamino-1,2-dihydro-1,3,5-triazin-2-one
1-(2'-ethyl-6'-chlorophenyl)-4-propargylamino-1,2-dihydro-1,3,5-triazin-2-one
1-(2'-ethyl-6'-chlorophenyl)-4-methoxyethylamino-1,2-dihydro-1,3,5-triazin-2-one
1-(2'-ethyl-6'-chlorophenyl)-4-benzyloxyethylamino-1,2-dihydro-1,3,5-triazin-2-one
1-(2'-ethyl-6'-chlorophenyl)-4-(N,N-dimethylamino)-1,2-dihydro-1,3,5-triazin-2-one
1-(2'-ethyl-6'-chlorophenyl)-4-(N,N-diethylamino)-1,2-dihydro-1,3,5-triazin-2-one
1-(2'-ethyl-6'-chlorophenyl)-4-(N-pyrrolidinyl)-1,2-dihydro-1,3,5-triazin-2-one
1-(2'-methyl-6'-fluorophenyl)-4-methylamino-1,2-dihydro-1,3,5-triazin-2-one
1-(2',6'-dimethyl-4'-hydroxyphenyl)-4-methylamino-1,2-dihydro-1,3,5-triazin-2-one
1-(2',6'-diethyl-4'-hydroxyphenyl)-4-methylamino-1,2-dihydro-1,3,5-triazin-2-one
1-(2'-methyl-6'-chloro-4'-hydroxyphenyl)-4-methylamino-1,2-hydro-1,3,5-triazin-2-one
1-(2'-methyl-6'-bromo-4'-hydroxyphenyl)-4-methylamino-1,2-dihydro-1,3,5-triazin-2-one
1-(2'-methyl-6'-fluoro-4'-hydroxyphenyl-4-methylamino-1,2-dihydro-1,3,5-triazin-2-one
1-(2'-methyl-6'-ethyl-4'-hydroxyphenyl)-4-methylamino-1,2-dihydro-1,3,5-triazin-2-one
1-(2'-ethyl-6'-chloro-4'-hydroxyphenyl)-4-methylamino-1,2-dihydro-1,3,5-triazin-2-one
1-(2'-ethyl-6'-bromo-4'-hydroxyphenyl)-4-methylamino-1,2dihydro-1,3,5-triazin-2-one
1-(2'-ethyl-6'-fluoro-4'-hydroxyphenyl)-4-methylamino-1,2-dihydro-1,3,5-triazin-2-one
1-(2',6'-dimethyl-4'-aminophenyl)-4-methylamino-1,2-dihydro-1,3,5-triazin-2-one
1-(2',6'-diethyl-4'-aminophenyl)-4-methylamino-1,2-dihydro-1,3,5-triazin-2-one
1-(2'-methyl-6'-ethyl-4'-aminophenyl)-4-methylamino-1,2-dihydro-1,3,5,-triazin-2-one 1-(2'-methyl-6'-ethyl-4'-aminophenyl)-4-methylamino-1,2-dihydro-1,3,5-triazin-2-one
1-(2'-methyl-6'-chloro-4'-aminophenyl)-4-methylamino-1,2-dihydro-1,3,5-triazin-2-one
1-(2'-methyl-6'-bromo-4'-aminophenyl)-4-methylamino-1,2-dihydro-1,3,5-triazin-2-one
1-(2'-methyl-6'-fluoro-4'-aminophenyl)-4-methylamino-1,2-dihydro-1,3,5-triazin-2-one
1-(2'-ethyl-6'-chloro-4'-aminophenyl)-4-methylamino-1,2-dihydro-1,3,5-triazin-2-one
1-(2'-ethyl-6'-bromo-4'-aminophenyl)-4-methylamino-1,2-dihydro-1,3,5-triazin-2-one
1-(2'-ethyl-6'-fluoro-4'-aminophenyl)-4-methylamino-1,2-dihydro-1,3,5-triazin-2-one
1-(2',6'-dimethyl-4'-acetylamino)-4-methylamino-1,2-dihydro-1,3,5-triazin-2-one
1-(2',6'-diethyl-4'-acetylamino)-4-methylamino-1,2-dihydro-1,3,5-triazin-2-one
1-(2'-methyl-6'-ethyl-4'-acetylamino)-4-methylamino-1,2-dihydro-1,3,5-triazin-2-one
1-(2'-methyl-6'-chloro-4'-acetylamino)-4-methylamino-1,2-dihydro-1,3,5-triazin-2-one
1-(2'-methyl-6'-bromo-4'-acetylamino)-4-methylamino-1,2-dihydro-1,3,5-triazin-2-one
1-(2'-methyl-6'-fluoro-4'-acetylamino)-4-methylamino-1,2-hydro-1,3,5-triazin-2-one
1-(2'-ethyl-6'-chloro-4'-acetylamino)-4-methylamino-1,2-hydro-1,3,5-triazin-2-one
1-(2'-ethyl-6'-bromo-4'-acetylamino)-4-methylamino-1,2-hydro-1,3,5-triazin-2-one
1-(2'-ethyl-6'-fluoro-4'-acetylamino-4-methylamino-1,2-dihydro-1,3,5-triazin-2-one
1-(2',6'-diethyl-4'-nitrophenyl)-4-methylamino-1,2-dihydro-1,3,5-triazin-2-one
1-(4'-amino-2',6'-diethylphenyl)-4-methylamino-1,2-dihydro-1,3,5-triazin-2-one
1-(2',6'-dimethyl-4'-aminophenyl-4-methylamino-1,2-dihydro-1,3,5-triazin-2-one
1-(2',6'-dimethylphenyl)-4-(N,N-diethylamino-1,2-dihydro-1,3,5-triazin-2-one
1-(2',6'-dimethylphenyl)-4-(N-ethyl-N-methylamino)-1,2-dihydro-1,3,5-triazin-2-one
1-(2',6'-dimethylphenyl)-4-(N-methyl-N-propylamino)-1,2-dihydro-1,3,5-triazin-2-one
1-(2',6'-dimethylphenyl)-4-(N-methyl-N-butylamino)-B 1,2-dihydro-1,3,5-triazin-2-one
1-(2',6'-dimethylphenyl)-4-(N,N-dipropylamino)-1,2-dihydro-1,3,5-triazin-2-one
1-(2',6'-dimethylphenyl)-4-(N-ethyl-N-propylamino)-1,2-dihydro-1,3,5-triazin-2-one
1-(2',6'-dimethylphenyl)-4-(N-methyl-N-benzyloxypropylamino)-1,2-dihydro-1,3,5-triazin-2-one
1-(2',6'-dimethylphenyl)-4-(N-methyl-N-phenethoxythylamino)-1,2-dihydro-1,3,5-triazin-2-one
1-(2',6'-dimethylphenyl)-4-(N-methyl-N-benzyloxyethylamino)-1,2-dihydro-1,3,5-triazin-2-one
1-(2',6'-dimethylphenyl)-4-(N-pyrrolidinyl)-1,2-dihydro-1,3,5-triazin-2-one
1-(2',6'-dimethylphenyl)-4-(N-piperidyl)-1,2-dihydro-1,3,5-triazin-2-one
1-(2',6'-dimethylphenyl)-4-(N-azipinyl)-1,2-dihydro-1,3,5-triazin-2-one
1-(2',6'-dimethylphenyl)-4-(N-morpholinyl)-1,2-dihydro-1,3,5-triazin-2-one
1-(2',6'-dimethyl)-4-[3-(N-methyl piperidyl]-1,2-dihydro-1,3,5-triazin-2-one
1-(2',6'-dimethylphenyl)-4-[3-(N-methyl acepinyl]-1,2-dihydro-1,3,5-triazin-2-one 1-(2',6'-dimethylphenyl)-4-[N-(3-thiomorpholinyl)]-1,2-dihydro 1,3,5-triazin-2-one
1-(2',6'-dimethylphenyl)-4-[N(]-thioazolinyl)]-1,2-dihydro-1,3,5-triazin-2-one
1-(2',6'-dimethylphenyl)4-(2-butenylamino)-1,2-dihydro-1,3,5-triazin-2-one
1-(2',6'-dimethylphenyl)-4-(2-butylnylamino)-1,2-dihydro-1,3,5-triazin-2-one
1-(2',6'-dimethylphenyl)-4-(3-butynylamino)-1,2-dihydro-1,3,5-triazin-2-one
1-(2',6'-dimethylphenyl)-4-(N-methyl-N-allylamino)-1,2-dihydro-1,3,5-griazin-2-one
1-(2',6'-dimethylphenyl)-4-(N-methyl-N-propargylamino)-1,2-dihydro-1,3,5-triazin-2-one
1-(2',6'-dimethylphenyl)-4-(N-methyl-N-cyclopropylamino)-1,2-dihydro-1,3,5-triazin-2-one
1-(2',6'-dimethylphenyl)-4-methylamino-1,2-dihydro-1,3,5-triazin-2-one
1-(2',6'-dimethylphenyl)-4-(N,N-dimethylamino)-1,2-dihydro-1,3,5-triazin-2-one
1-(2'-methyl-6'-methoxyphenyl)-4-methylamino-1,2-dihydro-1,3,5-triazin-2-one
1-(2'-methylphenyl)-4-methylamino-1,2-dihydro-1,3,5-triazin-2-one
1-(2',4',6'-trimethylphenyl)-4-methylamino-1,2-dihydro-1,3,5-triazin-2-one
1-(2'-methyl-4'-bromo-6'-chlorophenyl)-4-methylamino-1,2-dihydro-1,3,5-triazin-2-one
1-(2'-chloro-6'-fluorophenyl)-4-methylamino-1,2-dihydro-1,3,5-triazin-2-one
1-(2',5'-dichlorophenyl)-4-methylamino-1,2-dihydro-1,3,5-triazin-2-one
1-(2'-chloro-6'-bromophenyl)-4-methylamino-1,2-dihydro-1,3,5-triazin-2-one
1-(2'-chloro-5'-bromophenyl)-4-methylamino-1,2-dihydro-1,3,5-triazin-2-one
1-(2'-chloro-5'-fluorophenyl)-4-methylamino-1,2-dihydro-1,3,5-triazin-2-one
1-(2'-fluoro-5'-chlorophenyl)-4-methylamino-1,2-dihydro-1,3,5-triazin-2-one
1-(2'-fluoro-5'-bromophenyl)-4-methylamino-1,2-dihydro-1,3,5-triazin-2-one
1-(2',5',6'-triethylphenyl)-4-methylamino-1,2-dihydro-1,3,5-triazin-2-one
1-(2',4'-dimethyl-6'-ethylphenyl)-4-methylamino-1,2-dihydro-1,3,5-triazin-2-one
1-(2',6'-dimethyl-4'-ethylphenyl)-4-methylamino-1,2-dihydro-1,3,5-triazin-2-one
1-(2'-ethylphenyl)-4-methylamino-1,2-dihydro-1,3,5-triazin-2-one
1-(2'-ethyl-4'-bromo-6'-chlorophenyl)-4-methylamino-1,2-dihydro-1,3,5-triazin-2-one
1-(2'-ethyl-6'-methoxyphenyl)-4-methylamino-1,2-dihydro-1,3,5-triazin-2-one
1-(2'-methyl-6'-ethoxyphenyl)-4-methylamino-1,2-dihydro-1,3,5-triazin-2-one
1-(2',6'-dimethylphenyl)-4-ethylamino-1,2-dihydro-1,3,5-triazin-2-one
1-(2',6'-dimethylphenyl)-4-propylamino-1,2-dihydro-1,3,5-triazin-2-one
1-(2',6'-dimethylphenyl)-4-(i-propylamino)1,2-dihydro-1,3,5-triazin-2-one
1-(2',6'-dimethylphenyl)-4-butylamino-1,2-dihydro-1,3,5-triazin-2-one
1-(2',6'-dimethylphenyl)-4-(i-butylamino)-1,2-dihydro-1,3,5-triazin-2-one
1-(2',6'-dimethylphenyl)-4-(sec-butylamino-1,2-dihydro-1,3,5-triazin-2-one 1-(2',6'-dimethylphenyl)-4-(t-butylamino)-1,2-dihydro-1,3,5-triazin-2-one
1-(2',6'-dimethylphenyl)-4-pentylamino-1,2-dihydro-1,3,5-triazin-2-one
1-(2',6'-dimethylphenyl)-4-hexylamino-1,2-dihydro-1,3,5-triazin-2-one
1-(2',6'-dimethylphenyl)-4-heptylamino-1,2-dihydro-1,3,5-triazin-2-one
1-(2',6'-dimethylphenyl)-4-cyclopropylamino-1,2-dihydro-1,3,5-triazin-2-one
1-(2',6'-dimethylphenyl)-4-cyclobutylamino-1,2-dihydro-1,3,5-triazin-2-one
1-(2',6'-dimethylphenyl)-4-cyclopentylamino-1,2-dihydro-1,3,5-triazin-2-one
1-(2',6'-dimethylphenyl)-4-cyclohexylamino-1,2-dihydro-1,3,5-triazin-2-one
1-(2',6'-dimethylphenyl)-4-anilino-1,2-dihydro-1,3,5-triazin-2-one
1-(2',6'-dimethylphenyl)-4-benzylamino-1,2-dihydro-1,3,5-triazin-2-one
1-(2',6'-dimethylphenyl)-4-phenethylamino-1,2-dihydro-1,3,5-triazin-2-one
1-(2',6'-dimethylphenyl)-4-(N-methyl-N-benzylamino)-1,2-dihydro-1,3,5-triazin-2-one
1-(2',6'-dimethylphenyl)-4-(N,N-dibenzylamino)-1,2-dihydro-1,3,5-triazin-2-one
1-(2'-methyl-6'-chlorophenyl)-4-amino-1,2-dihydro-1,3,5-triazin-2-one
1-(2'-methyl-6'-fluorophenyl)-4-amino-1,2-dihydro-1,3,5-triazin-2-one
1-(2'-methyl-6'-bromophenyl)-4-amino-1,2-dihydro-1,3,5-triazin-2-one
1-(2'-methyl-6'-iodophenyl)-4-amino-1,2-dihydro-1,3,5-triazin-2-one
1-(2'-methyl-6'-methoxyphenyl)-4-amino-1,2-dihydro-1,3,5-triazin-2-one
1-(2'-methyl-6'-ethoxyphenyl)-4-amino-1,2-dihydro-1,3,5-triazin-2-one
1-(2'-methyl-6'-ethylphenyl)-4-amino-1,2-dihydro-1,3,5-triazin-2-one
1-(2'-methyl-6'-propylphenyl)-4-amino-1,2-dihydro-1,3,5-triazin-2-one
1-(2'-methyl-6'-i-propylphenyl)-4-amino-1,2-dihydro-1,3,5-triazin-2-one
1-(2'-methyl-6'-butylphenyl)-4-amino-1,2-dihydro-1,3,5-triazin-2-one
1-(2'-methyl-6'-cyano phenyl)-4-amino-1,2-dihydro-1,3,5-triazin-2-one
1-(2'methyl-6'-trifluoromethylphenyl)-4-amino-1,2-dihydro-1,3,5-triazin-2-one
1-(2'-methyl-6'-nitrophenyl)-4-amino-1,2-dihydro-1,3,5-triazin-2-one
1-(2'-methyl-6'-methylsulfonylphenyl)-4-amino-1,2-dihydro-1,3,5-triazin-2-one
1-(2'-ethyl-6'-chlorophenyl)-4-amino-1,2-dihydro-1,3,5-triazin-2-one
1-(2'-ethyl-6'-fluorophenyl)-4-amino-1,2-dihydro-1,3,5-triazin-2-one
1-(2'-ethyl-6'-bromophenyl)-4-amino-1,2-dihydro-1,3,5-triazin-2-one
1-(2'-ethyl-6'-methoxyphenyl)-4-amino-1,2-dihydro-1,3,t-triazin-2-one
1-(2'-ethyl-6'-ethoxyphenyl)-4-amino-1,2-dihydro-1,3,5-triazin-2-one
1-(2',6'-diethylphenyl)-4-amino-1,2-dihydro-1,3,5-triazin-2-one
1-(2'-ethyl-6'-propylphenyl)-4-amino-1,2-dihydro-1,3,5-triazin-2-one
1-(2'-ethyl-6'-trifluoromethylphenyl)-4-amino-1,2-dihydro-1,3,5-triazin-2-one
1-(2'-propyl-6'-chlorophenyl)-4-amino-1,2-dihydro-1,3,5-triazin-2-one
1-(2'-propyl-6'-bromophenyl)-4-amino-1,2-dihydro-1,3,5-triazin-2-one
1-(2'-propyl-6-methoxyphenyl)-4-amino-1,2-dihydro-1,3,5-triazin-2-one
1-(2'-propyl-6'-ethoxyphenyl)-4-amino-1,2-dihydro-1,3,5-triazin-2-one
1-(2',6'-dipropylphenyl)-4-amino-1,2-dihydro-1,3,5-triazin-2-one
1-(2'-i-propyl-6'-chlorophenyl)-4-amino-1,2-dihydro-1,3,5-triazin-2-one
1-(2',6'-dichlorophenyl)-4-amino-1,2-dihydro-1,3,5-triazin-2-one
1-(2'-chloro-3'-methylphenyl)-1,2-dihydro-1,3,5-triazin-2-one
1-(2'-chloro-4'-methylphenyl)-4-amino-1,2-dihydro-1,3,5-triazin-2-one
1-(2'-chloro-5'-methylphenyl)-4-amino-1,2-dihydro-1,3,5-triazin-2-one
1-(2'-chloro-5'-trifluoromethylphenyl)-4-1,2-dihydro-1,3,5-triazin-2-one
1-(2'-chloro-6'-fluorophenyl)-4-amino-1,2-dihydro-1,3,5-triazin-2-one
1-(2',6'-difluorophenyl)-4-amino-1,2-dihydro-1,3,5-triazin-2-one
1-(2'-propylphenyl)-4-amino-1,2-dihydro-1,3,5-triazin-2-one
1-(4'-trifluoromethylphenyl)-4-amino-1,2-dihydro-1,3,5-triazin-2-one
1-(3',4'-dimethoxyphenyl)-4-amino-1,2-dihydro-1,3,5-triazin-2-one
1-(3',4',5',-trimethoxyphenyl)-4-amino-1,2-dihydro-1,3,5-triazin-2-one
1-(3',4',diethoxyphenyl)-4-amino-1,2-dihydro-1,3,5-triazin-2
1-(2, 4'-dimethylphenyl)-4-amino-1,2-dihydro-1,3,5-triazin-2-one
1-(2, 4'-diethylphenyl)4-4amino-1,2-dihydro-1,3,5-triazin-2-one
1-(2'-methyl-4'-ethylphenyl)-4-amino-1,2-dihydro-1,3,5-triazin-2-one
1-(2'-methyl-4'-chlorophenyl)-4-amino-1,2-dihydro-1,3,5-triazin-2-one
1-(2'-ethyl-4'-chlorophenyl)-4-amino-1,2-dihydro-1,3,5-triazin-2-one
1-(2',4',6'-trimethylphenyl)-4-amino-1,2-dihydro-1,3,5-triazin-2-one
1-(2',4'-dimethyl-6'-ethylphenyl)-4-amino-1,2-dihydro-1,3,5-triazin-2-one
1-(2',4'-dimethyl-6'-trifluoromethylphenyl)-4-amino-1,2-dihydro-1,3,5-triazin-2-one
1-(2',4'-dimethyl-6'-nitrophenyl-4-amino-1,2-dihydro-1,3,5-triazin-2-one
1-(2',4'-dimethyl-6'-methoxyphenyl)-4-amino-1,2-dihydro-1,3,5-triazin-2-one
1-(2',6'-dimethyl-4'-chlorophenyl)-4-amino-2-dihydro-1,3,5-triazin-2-one
1-(2',6'-dimethyl-4'-bromophenyl)-4-amino-1,2-dihydro-1,3,5-triazin-2-one
1-(2',6'-dimethyl-4'-methoxyphenyl)-4-amino-1,2-dihydro-1,3,5-triazin-2-one
1-(2'-methyl-4',6'-dichlorophenyl)-4-amino-1,2-dihydro-1,3,5-triazin-2-one
1-(2'-methyl-4',6'-difluorophenyl)-4-amino-1,2-dihydro-1,3,5-triazin-2-one 1-(2'-methyl-4'-fluoro-6'-bromophenyl)-4-amino-1,2-dihydro-1,3,5-triazin-2-one
1-(2'-methyl-4'-chloro-6'-trifluoromethylphenyl)-4-amino-1,2-dihydro-1,3,5-triazin-2-one
1-(2'-methyl-4'-trifluoromethyl-6-chlorophenyl)-4-amino-1,2-dihydro-1,3,5-triazin-2-one
1-(2'-ethyl-4',6'-dichlorophenyl)-4-amino-1,2-dihydro-1,3,5-triazin-2-one
1-(2',6'-diethyl-4'-chlorophenyl)-4-amino-1,2-dihydro-1,3,5-triazin-2-one
1-(2',6'-diethyl-4'-bromophenyl)-4-amino-1,2-dihydro-1,3,5-triazin-2-one
1-(2',6'-diethyl-4'-fluorophenyl)-4-amino-1,2-dihydro-1,3,5-triazin-2-one
1-(2'-chloro-6'-methylphenyl)-4-amino-1,2-dihydro-1,3,5-triazin-2-one
1-(2',6'-dimethylphenyl)-4-amino-1,2-dihydro-1,3,5-triazin-2-one
1-(2',6'-diethylphenyl)-4-amino-1,2-dihydro-1,3,5-triazin-2-one
1-(2'-methyl-6'-methoxyphenyl)-4-amino-1,2-dihydro-1,3,5-triazin-2-one
1-(2'-methyl-6'-chlorophenyl)-4-amino-1,2-dihydro-1,3,5-triazin-2-one
1-(2'-methylphenyl)-4-amino-1,2-dihydro-1,3,5-triazin-2-one
1-(2'-chloro-6'-fluorophenyl)-4-amino-1,2-dihydro-1,3,5-triazin-2-one
1-(2'-methyl-6'-ethylphenyl)-4-amino-1,2-dihydro-1,3,5-triazin-2-one
1-(2',4',6'-trimethylphenyl)-4-amino-1,2-dihydro-1,3,5-triazin-2-one
1-(2'-methyl-6'-methoxyphenyl)-4-methylamino-1,2-dihydro-1,3,5-triazin-2-one
1-(2'-methylphenyl)-4-methylamino-1,2-dihydro-1,3,5-triazin-2-one
1-(2',4',6'-trimethylphenyl)-4-methylamino-1,2-dihydro-1,3,5-triazin-2-one
1(2'-methyl-4'-bromo-6'-chlorophenyl)-4-methylamino-1,2-dihydro-1,3,5-triazin-2-one
1-(2'-chloro-6'-fluorophenyl)-4-methylamino-1,2-dihydro-1,3,5-triazin-2-one
1-(2',5'-dichlorophenyl)-4-methylamino-1,2-dihydro-1,3,5-triazin-2-one
1-(2'-chloro-6'-bromophenyl)-4-methylamino-1,2-dihydro-1,3,5-triazin-2-one
1-(2'-chloro-5'-bromophenyl)-4-methylamino-1,2-dihydro-1,3,5-triazin-2-one
1-(2'-chloro-5'-fluorophenyl)-4-methylamino-1,2-dihydro-1,3,5-triazin-2-one
1-(2'-fluoro-5'-chlorophenyl)-4-methylamino-1,2-dihydro-1,3,5-triazin-2-one
1-(2'-fluoro-5'-bromophenyl)-4-methylamino-1,2-dihydro-1,3,5-triazin-2-one
1-(2',4',6'-triethylphenyl)-4-methylamino-1,2-dihydro-1,3,5-triazin-2-one
1-(2',4'-dimethyl-6'-ethylphenyl)-4-methylamino-1,2-dihydro-1,3,5-triazin-2-one
1-(2'6'-dimethyl-4'-ethylphenyl)-4-methylamino-1,2-dihydro-1,3,5-triazin-2-one
1-(2'-ethylphenyl)-4-methylamino-1,2-dihydro-1,3,5-triazin-2-one
1-(2'-ethyl-4'-bromo-6'-chlorophenyl)-4-methylamino-1,2-dihydro-1,3,5-triazin-2-one
1-(2'-ethyl-6'-methoxyphenyl)-4-methylamino-1,2-dihydro-1,3,5-triazin-2-one
1-(2'-methyl-6'-ethoxyphenyl)-4-methylamino-1,2-dihydro-1,3,5-triazin-2-one
1-(2',6'-dimethylphenyl)-4-(2',6'-dimethylphenylamino)-1,2-dihydro-1,3,5-triazin-2-one
1-(2',6'-dimethylphenyl)-4-(2'-methylphenylamino)-1,2-dihydro-1,3,5-triazin-2-one
1-(2',6'-dimethylphenyl)-4-(2'6'-diethylphenylamino)-1,2-dihydro-1,3,5-triazin-2-one
1-(2',6'-dimethylphenyl)-4-(2'-methyl-6'-chlorophenylamino-1,2-dihydro-1,3,5-triazin-2-one
1-(2',6'-dimethylphenyl)-4-(2',4',6'-trimethylphenylamino)-1,2-dihydro-1,3,5-triazin-2-one

TABLE III 1-(2',6'-diethylphenyl)-3-methylamidinothiourea
1-(2',6'-diethylphenyl)-3-ethylamidinothiourea
1-(2',6'-diethylphenyl)-3-i-propylamidinothiourea
1-(2',6'-diethylphenyl)-3-pentylamidinothiourea
1-(2',6'-diethylphenyl)-3-allylamidinothiourea
1-(2',6'-diethylphenyl)-3-propargylamidinothiourea
1-(2',6'-diethylphenyl)-3-cyclopropylamidinothiourea
1-(2',6'-diethylphenyl)-3-methoxyethylamidinothiourea
1-(2',6'-diethylphenyl)-3-benzyloxyethylamidinothiourea
1-(2',6'-diethylphenyl)-3-phenethoxyethylamidinothiourea
1-(2',6'-diethylphenyl)-3-benzylamidinothiourea
1-(2',6'-diethylphenyl)-3-(N,N-dimethylamidino)thiourea
1-(2',6'-diethylphenyl)-3-(N,N-tetramethyleneamidino)thiourea
1-(2'-methyl-6'-ethylphenyl)-3-methylamidinothiourea
1-(2'-methyl-6'-ethylphenyl)-3-t-butylamidinothiourea
1-(2'-methyl-6'-ethylphenyl)-3-propargylamidinothiourea
1-(2'-methyl-6'-ethylphenyl)-3-cyclopropylamidinothiourea
1-(2'-methyl-6'-ehtylphenyl)-3-[N-(3'-cyclopentenyl)amidino]thiourea
1-(2'-methyl-6'-ethylphenyl)-3-phenethoxyethylamidinothiourea
1-(2'-methyl-6'-ethylphenyl-3-benzylamidinothiourea
1-(2'-methyl-6'-ethylphenyl)-3-[N,N-diethylamidino)thiourea
1-(2'-methyl-6'-ethylphenyl)-3-[N,N(3'-methyl-3'-azapentamethylene)amidino]thiourea
1-(2'-methyl-6-ethylphenyl)-3-[N,N-(3'-oxapentamethylene)amidino]thiourea
1-(2'-methyl-6'-chlorophenyl)-3-methylamidinothiourea
1-(2'-methyl-6'-chlorophenyl)-3-ethylamidinothiourea
1-(2'-methyl-6'-chlorophenyl)-3-propargylamidinothiourea
1-(2'-methyl-6'-chlorophenyl)-3-cyclohexylamidinothiourea
1-(2'-methyl-6'-chlorophenyl)-3-benzylamidinothiourea
1-(2'-methyl-6'-chlorophenyl)-3-methoxyethylamidinothiourea
1-(2'-methyl-6'-chlorophenyl)-3-(N,N-diethylamidino)thiourea
1-(2'-methyl-6'-chlorophenyl)-3-(N,N-pentamethyleneamidino)thiourea
1-(2'-methyl-6'-bromophenyl)-3-ethylamidinothiourea
1-(2'-ethyl-6'-chlorophenyl)-3-methylamidinothiourea
1-(2'-ethyl-6'-chlorophenyl)-3-benzyloxyethylamidinothiourea
1-(2'-methyl-6'-fluorophenyl)-3-methylamidinothiourea
1-(2',6'-dimethyl-4'-hydroxyphenyl)-3-methylamidinothiourea 1-(2',6'-diethyl-4'-hydroxyphenyl)-3-methylamidinothiourea
1-(2'-methyl-6'-chloro-4'-hydroxyphenyl)-3-methylamidinothiourea
1-(2',6'-dimethyl-4'-aminophenyl)-3-methylamidinothiourea
1-(2',6'-diethyl-4'-aminophenyl)-3-methylamidinothiourea
1-(2',6'-dimethyl-4'-acetylamino)-3-methylamidinothiourea
1-(2'-methyl-6'-chloro-4'-acetylamino)-3-methylamidinothiourea
1-(2',6'-diethyl-4'-nitrophenyl)-3-methylamidinothiourea hydrochloride
1-(2',6'-dimethyl-4'-aminophenyl-3-methylamidinothiourea hydrochloride
1-(2',6'-dimethylphenyl)-3-(N,N-diethylamidino)thiourea hydrochloride
1-(2',6'-dimethylphenyl)-3-(N,N-dipropylamidino)thiourea hydrochloride
1-(2',6'-dimethylphenyl)-3-(N-methyl-N-benzyloxyethylamidino)thiourea hydrochloride
1-(2',6'-dimethylphenyl)-3-(N,N-tetramethyleneamidino)thiourea hydrochloride
1-(2',6'-dimethylphenyl)-3-(N-methylamidino)thiourea
1-(2',6'-diemthylphenyl)-3-(N,N-dimethylamidino)thiourea
1-(2',4',6'-trimethylphenyl)-3-(N-methylamidino)thiourea
1-(2',5'-dichlorophenyl)-3-(N-methylamidino)thiourea
1-(2',4',6'-triethylphenyl)-3-(N-methylamidino)thiourea
1-(2'-ethylphenyl)-3-(N-methylamidino)thiourea
1-(2',6'-dimethylphenyl)-3-(N-ethylamidino)thiourea
1-(2',6'-dimethylphenyl)-3-(N-propylamidino)thiourea
1-(2',6'-dimethylphenyl)-3-(N-i-propylamidino)thiourea
1-(2',6'-dimethylphenyl)-3-(N-t-butylamidino)thiourea
1-(2',6'-dimethylphenyl)-3-(N-cyclohexylamidino)thiourea
1-(2',6'-dimethylphenyl)-3-(N-phenylamidino)thiourea
1-(2',6'-dimethylphenyl)-3-(N-benzylamidino)thiourea
1-(2',6'-dimethylphenyl)-3-(N-methyl-N-benzylamidino)thiourea
1-(2',6'-dipropylphenyl)-3-amidinothiourea
1-(2',6'-difluorophenyl)-3-amidinothiourea
1-(2'-propylphenyl)-3-amidinothiourea
1-(4'-trifluoromethylphenyl)-3-amidinothiourea
1-(2',6'-dimethyl-4'-chlorophenyl)-3-amidinothiourea
1-(2',6'-dimethylphenyl)-3-amidinothiourea
1-(2',6'-diethylphenyl)-3-amidinothiourea
1-(2'-methylphenyl)-3-amidinothiourea
1-(2'-methyl-6'-ethylphenyl)-3-amidinothiourea
1-(2',4',6'-trimethylphenyl)-3-amidinothiourea
1-(2',6'-dimethylphenyl)-3-[N-(2',6'-dimethylphenyl)amidino]thiourea

TABLE IV 1-(2',6'-diethylphenyl)-4-methylamino-1,2-dihydro-1,3,5-triazin-2-thione
1-(2',6'-diethylphenyl)-4-ethylamino-1,2-dihydro-1,3,5-triazin-2-thione
1-(2',6'-diethylphenyl)-4-i-propylamino-1,2-dihydro-1,3,5-triazin-2-thione
1-(2',6'-diethylphenyl)-4-pentylamino-1,2-dihydro-1,3,5-triazin-2-thione
1-(2',6'-diethylphenyl)-allylamino-1,2-dihydro-1,3,5-triazin-2-thione
1-(2',6'-diethylphenyl)-4-propargylamino-1,2-dihydro-1,3,5-triazin-2-thione
1-(2',6'-diethylphenyl)-4-cyclopropylamino-1,2-dihydro-1,3,5-triazin-2-thione
1-(2',6'-diethylphenyl)-4-methoxyethylamino-1,2-dihydro-1,3,5-triazin-2-thione
1-(2',6'-diethylphenyl)-4-benzyloxyethylamino-1,2-dihydro-1,3,5-triazin-2-thione
1-(2',6'-diethylphenyl)-4-phenethoxyethylamino-1,2-dihydro-1,3,5-triazin-2-thione
1-(2',6'-diethylphenyl)-4-benzylamino-1,2-dihydro-1,3,5-triazin-2-thione
1-(2',6'-diethylphenyl)-4-(N,N-dimethylamino)-1,2-dihydro-1,3,5-triazin-2-thione
1-(2',6'-diethylphenyl)-4-(N-pyrrolidinyl)-1,2-dihydro-1,3,5-triazin-2-thione
1-(2'-methyl-6'-ethyl-phenyl)-4-methylamino-1,2-dihydro-1,3,5-triazin-2-thione
1-(2'-methyl-6'-ethyl-phenyl)-4-t-butylamino-1,2-dihydro-1,3,5-triazin-2-thione
1-(2'-methyl-6'-ethyl-phenyl)-4-propargylamino-1,2-dihydro-1,3,5-triazin-2-thione
1-(2'-methyl-6'-ethylphenyl)-4-cyclopropylamino-1,2-dihydro-1,3,5-triazin-2-thione
1-(2'-methyl-6'-ethyl-phenyl)-4-cyclopentenyl-3-amino-1,3,5-triazin-2-thione
1-(2'-methyl-6'-ethyl-phenyl)-4-phenethoxyethylamino-1,2-dihydro-1,3,5-triazin-2-thione
1-(2'-methyl-6'-ethyl-phenyl)-4-benzylamino-1,2-dihydro-1,3,5-triazin-2-thione
1-(2'-methyl-6'-ethyl-phenyl)-4-(N,N-diethylamino)-1,2-dihydro-1,3,5-triazin-2-thione
1-(2'-methyl-6'-ethyl-phenyl)-4-[3-(N-methylpiperidyl)]-1,2-dihydro-1,3,5-triazin-2-thione
1-(2'-methyl-6'-ethylpheny)-4-(N-morpholinyl)-1,2-dihydro-1,3,5-triazin-2-thione
1-(2'-methyl-6'-chlorophenyl)-4-methylamino-1,2-dihydro-1,3,5-triazin-2-thione
1-(2',6'-dimethyl-4'-acetylamino)-4-methylamino-1,2-dihydro-1,3,5-triazin-2-thione
1-(2'-methyl-6'-chloro-4'-acetylamino)-4-methylamino-1,2-dihydro-1,3,5-triazin-2-thione
1-(2',6'-diethyl-4'-nitrophenyl)-4-methylamino-1,2-dihydro-1,3,5-triazin-2-thione
1-(2',6'-dimethyl-4'-aminophenyl)-4-methylamino-1,2-dihydro-1,3,5-triazin-2-thione
1-(2',6'-dimethylphenyl)-4-(N,N-diethylamino-1,2-dihydro-1,3,5-triazin-2-thione
1-(2',6'-dimethylphenyl)-4-(N,N-dipropylamino)-1,2-dihydro-1,3,5-triazin-2-thione
1-(2',6'-dimethylphenyl)-4-(N-methyl-N-benzyloxethylamino)-1,2-dihydro-1,3,5-triazin-2-thione
1-(2',6'-dimethylphenyl)-4-(N-pyrrolidinyl)-1,2-dihydro-1,3,5-triazin-2-thione
1-(2',6'-dimethylphenyl)-4-methylamino-1,2-dihydro-1,3,5-triazin-2-thione
1-(2',6'-dimethylphenyl)-4-(N,N-dimethylamino)-1,2-dihydro-1,3,5-triazin-2-thione
1-(2',4',6'-trimethylphenyl)-4-methylamino-1,2-dihydro-1,3,5-triazin-2-thione
(1-(2',5'-dichlorophenyl)-4-methylamino-1,2-dihydro-1,3,5-triazin-2-thione
1-(2',4',6'-triethylphenyl)-4-methylamino-1,2-dihydro-1,3,5-triazin-2-thione
1-(2'-ethylphenyl)-4-methylamino-1,2-dihydro-1,3,5 triazin-2-thione
1-(2',6'-dimethylphenyl)-4-ethylamino-1,2-dihydro-1,3,5-triazin-2-thione
1-(2',6'-dimethylphenyl)-4-propylamino-1,2-dihydro-1,3,5-triazin-2-thione 1-(2',6'-dimethylphenyl)-4-(i-propylamino)-1,2-dihydro-1,3,5-triazin-2-thione
1-(2',6'-dimethylphenyl)-4-(t-butylamino)-1,2-dihydro-1,3,5-triazin-2-thione
1-(2',6'-dimethylphenyl)-4-cyclohexylamino-1,2-dihydro-1,3,5-triazin-2-thione
1-(2',6'-dimethylphenyl)-4-anilino-1,2-dihydro-1,3,5-triazin-2-thione
1-(2',6'-dimethylphenyl)-4-benzylamino-1,2-dihydro-1,3,5-triazin-2-thione
1-(2',6'-dimethylphenyl)-4-(N-methyl-N-benzylamino)-1,2-dihydro-1,3,5-triazin-2-thione
1-(2',6'-dipropylphenyl)-4-amino-1,2-dihydro-1,3,5-triazin-2-thione
1-(2',6'-difluorophenyl)-4-amino-1,2-dihydro-1,3,5-triazin-2-thione
1-(2'-propylphenyl)-4-amino-1,2-dihydro-1,3,5-triazin-2-thione
1-(4'-trifluoromethylphenyl)-4-amino-1,2-dihydro-1,3,5-triazin-2-thione
1-(2',6'-dimethyl-4'-chlorophenyl)-4-amino-1,2-dihydro-1,3,5-triazin-2-thione
1-(2',6'-dimethylphenyl)-4-amino-1,2-dihydro-1,3,5-triazin-2-thione
1-(2',6'-diethylphenyl)-4-amino-1,2-dihydro-1,3,5-triazin-2-thione
1-(2'-methylphenyl)-4-amino-1,2-dihydro-1,3,5-triazin-2-thione
1-(2'-methyl-6'-ethylphenyl)-4-amino-1,2-dihydro-1,3,5-triazin-2-thione
1-(2',4',6'-trimethylphenyl)-4-amino-1,2-dihydro-1,3,5-triazin-2-thione
1-(2',6'-dimethylphenyl)-4-(2',6'-dimethylphenylamino)-1,2-dihydro-1,3,5-triazin-2-thione

TABLE I $$R_1-NHCONHC\begin{matrix}\diagup NH \\ \diagdown N\diagup R_3 \\ \phantom{xx}\diagdown R_4\end{matrix}$$

| $R_1$ | $R_3$ | $R_4$ |
|---|---|---|
| 2,6-dimethylbenzyl | H | —CH$_3$ |
| 2,6-dimethylbenzyl | —CH$_3$ | —CH$_3$ |
| 2,6-dimethylbenzyl | H | —OCH$_3$ |

TABLE I-continued $$R_1-NHCONHC\begin{matrix}\diagup NH \\ \diagdown N\diagup R_3 \\ \phantom{xx}\diagdown R_4\end{matrix}$$

| $R_1$ | $R_3$ | $R_4$ |
|---|---|---|
| 2-methyl-6-ethylbenzyl | H | —CH$_3$ |
| 2,6-dichlorobenzyl | H | —CH$_3$ |
| 2-methyl-6-chlorobenzyl | H | —CH$_3$ |
| 2,4,6-trimethylbenzyl | H | —CH$_3$ |
| 2,6-diethylbenzyl | H | —CH$_3$ |
| 2-methyl-6-trifluoromethylbenzyl | H | —CH$_3$ |
| 2-(2,6-dimethylphenyl)ethyl | H | —CH$_3$ |
| 2-(2,6-diethylphenyl)ethyl | H | H |

TABLE I-continued $$R_1-NHCONHC\overset{NH}{\underset{\underset{R_4}{N}}{\diagdown}}R_3$$

| $R_1$ | $R_3$ | $R_4$ |
|---|---|---|
| 2,6-dimethylphenyl-CH₂CH₂- | —CH₃ | —CH₃ |
| 2-CF₃-6-Cl-phenyl-CH₂CH₂- | H | —CH₃ |
| 2,6-dimethylphenyl-CH₂- | H | —C₃H₇ |
| 2,6-diethylphenyl-CH₂- | H | —C₂H₅ |
| 2,6-dimethylphenyl-CH₂- | H | —C₄H₉ |
| 2,6-bis(CF₃)phenyl-CH₂- | H | —CH₃ |
| 2,6-diethoxyphenyl-CH₂- | H | —CH₃ |
| 2-pyridyl | H | H |
| 2-pyridyl | H | —CH₃ |
| 2-pyridyl | H | —C₂H₅ |
| 2-pyridyl | —CH₃ | —CH₃ |
| 2-pyridyl | H | —OCH₃ |
| 3-methyl-2-pyridyl | H | —CH₃ |
| 3-methyl-2-pyridyl | —CH₃ | —CH₃ |
| 3-methyl-2-pyridyl | —C₂H₅ | —C₂H₅ |
| 3,4-dimethyl-2-pyridyl | H | H |
| 3,4-dimethyl-2-pyridyl | H | —CH₃ |
| 3,4-dimethyl-2-pyridyl | H | —C₂H₅ |

TABLE I-continued $$R_1-NHCONHC\begin{matrix}NH\\ \parallel\\ \diagdown\end{matrix}\begin{matrix}R_3\\ \diagup\\ N\\ \diagdown R_4\end{matrix}$$

| $R_1$ | $R_3$ | $R_4$ |
|---|---|---|
| 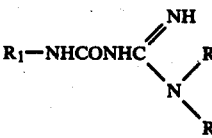 (3,5-dimethylpyridine) | H | —OCH$_3$ |
| 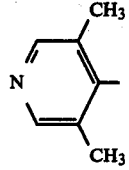 (3,5-dimethylpyridine) | —CH$_3$ | —CH$_3$ |
| 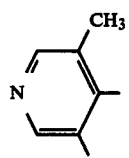 (3,5-dimethylpyridine) | —CH$_3$ | —C$_2$H$_5$ |
| 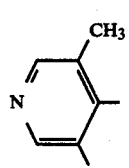 (2-pyridylmethyl) | H | H |
| 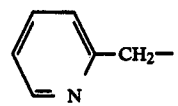 (2-pyridylmethyl) | H | —CH$_3$ |
| 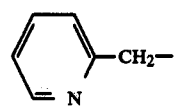 (2-pyridylmethyl) | H | —C$_2$H$_5$ |
| 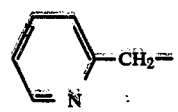 (pyrimidine) | H | H |
| 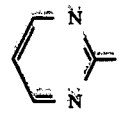 (pyrimidine) | H | —CH$_3$ |
|  (pyrimidine) | —CH$_3$ | —CH$_3$ |
|  (tetrahydropyrimidine) | —H | —CH$_3$ |
| 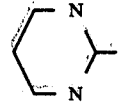 (tetrahydropyrimidine) | —H | —C$_2$H$_5$ |
| 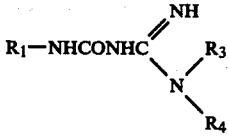 (tetrahydropyrimidine) | —CH$_3$ | —CH$_3$ |
| 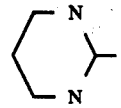 (dimethylpyrimidine) | H | H |
| 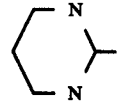 (dimethylpyrimidine) | H | —CH$_3$ |
| 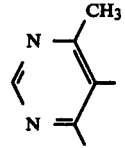 (dimethyltetrahydropyrimidine) | —CH$_3$ | —CH$_3$ |
| 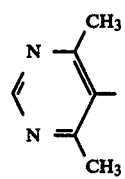 (dimethyltetrahydropyrimidine) | H | —C$_2$H$_5$ |
| 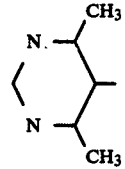 (4-pyridyl) | H | H |
| 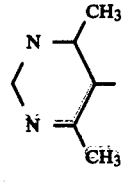 (4-pyridyl) | H | —CH$_3$ |
|  (imidazole) | H | H |
|  (imidazole) | H | —CH$_3$ |

TABLE I-continued
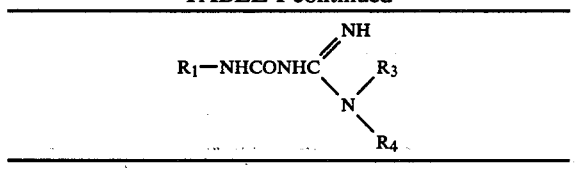
| R group | R₃ | R₄ |
|---|---|---|
| 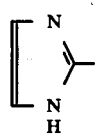 | H | —C₂H₅ |
| 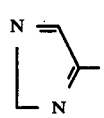 | H | H |
| 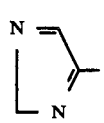 | H | —CH₃ |
| 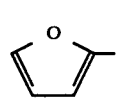 | H | —CH₃ |
|  | H | H |
| 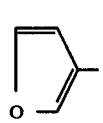 | H | —CH₃ |
| 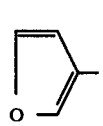 | H | —C₂H₅ |
| 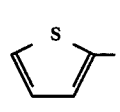 | H | —CH₃ |
| 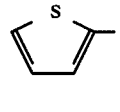 | —CH₃ | —CH₃ |
| 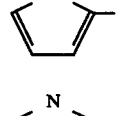 | —H | —CH₃ |
| 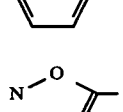 | —H | —C₂H₅ |
| 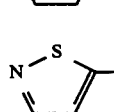 | —H | —CH₃ |
| 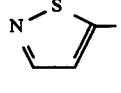 | H | —CH₃ |
TABLE I-continued
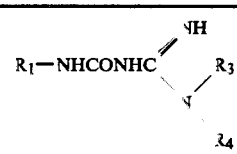
| R group | R₃ | R₄ |
|---|---|---|
| 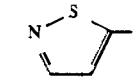 | H | —C₂H₅ |
| 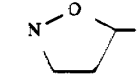 | H | —CH₃ |
| 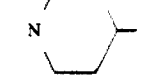 | H | —C₂H₅ |
| 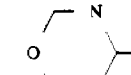 | H | —CH₃ |
| 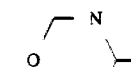 | H | —C₂H₅ |
| 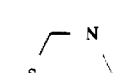 | H | —CH₃ |
| 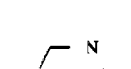 | H | —C₂H₅ |
| 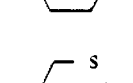 | H | —CH₃ |
| 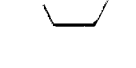 | H | —C₂H₅ |
|  | H | 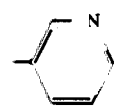 |
| 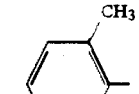 | —CH₃ | 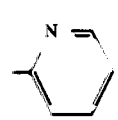 |

TABLE I-continued $$R_1\text{—NHCONHC}\overset{NH}{\underset{\underset{R_4}{N}}{\diagup}}R_3$$

| $R_1$ | $R_3$ | |
|---|---|---|
| 2,6-dimethylphenyl | —CH$_3$ | 4-pyridyl |
| 2,6-dimethylphenyl | —CH$_3$ | 2-pyridyl |
| 2,6-diethylphenyl | —CH$_3$ | 2-pyridyl |
| 3-methyl-2-pyridyl | —CH$_3$ | 2-pyridyl |

| $R_1$ | $-N\overset{R_3}{\underset{R_4}{\diagdown}}$ (ring) |
|---|---|
| 2,6-dimethylphenyl | pyrrolidinyl |
| 2,6-dimethylphenyl | aziridinyl |
| 2,6-dimethylphenyl | hexahydropyrimidinyl |
| 2,6-dimethylphenyl | morpholinyl |
| 2,6-dimethylphenyl | thiomorpholinyl |
| 2,6-dimethylphenyl | piperazinyl |
| 2,6-dimethylphenyl | pyrazolidinyl |
| 2,6-dimethylphenyl | piperidinyl |
| 2,6-diethylphenyl | piperidinyl |
| 2-methyl-6-ethylphenyl | piperidinyl |
| 2,6-dichlorophenyl | piperidinyl |

TABLE I-continued
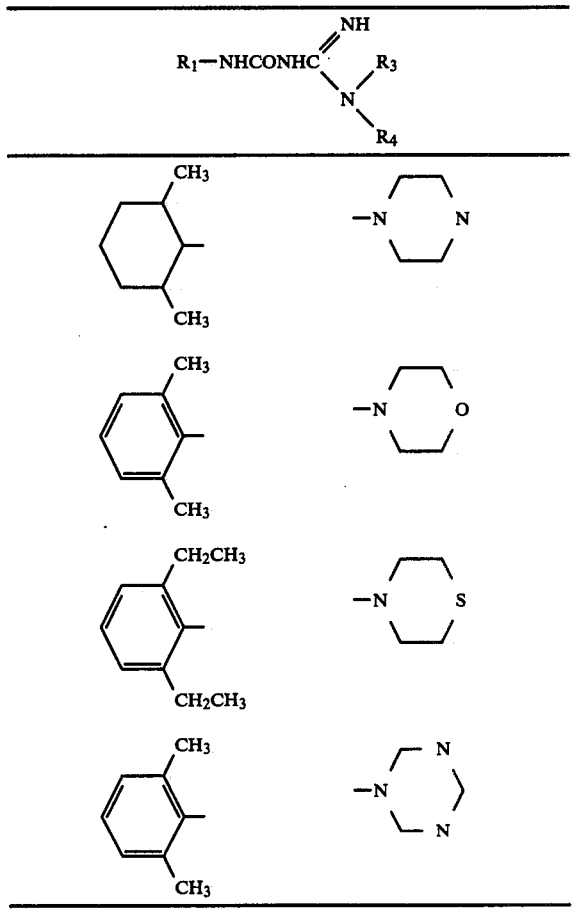
TABLE II
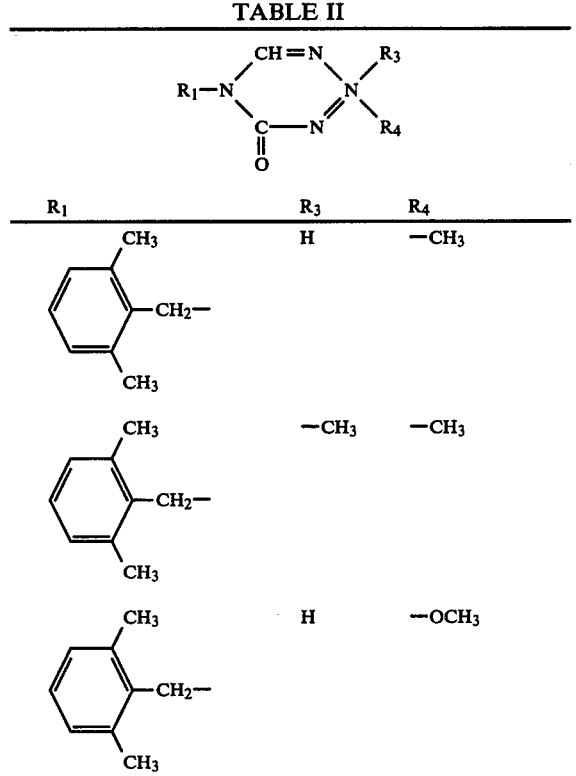

TABLE II-continued
| | | |
|---|---|---|
| 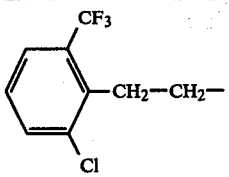 | H | —CH₃ |
| 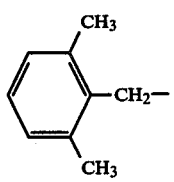 | H | —C₃H₇ |
| 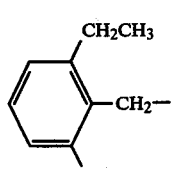 | H | —C₂H₅ |
| 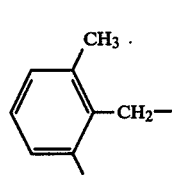 | H | —C₄H₉ |
| 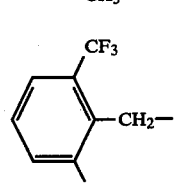 | H | —CH₃ |
| 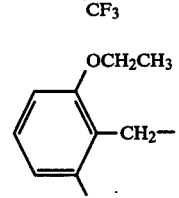 | H | —CH₃ |
| 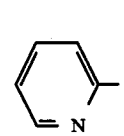 | H | H |
| 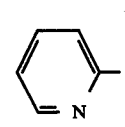 | H | —CH'₃ |
| 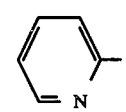 | H | —C₂H₅ |
| 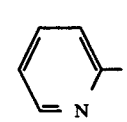 | —CH₃ | —CH₃ |
| 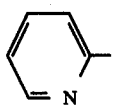 | H | —OCH₃ |
| 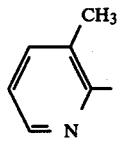 | H | —CH₃ |
| 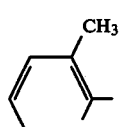 | —CH₃ | —CH₃ |
| 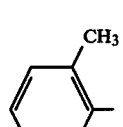 | —C₂H₅ | —C₂H₅ |
| 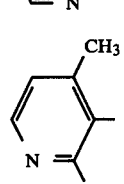 | H | H |
| 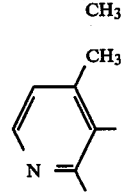 | H | —CH₃ |
| 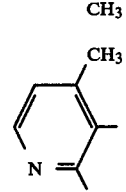 | H | —C₂H₅ |
| 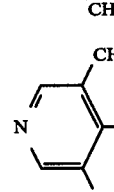 | H | —OCH₃ |
| 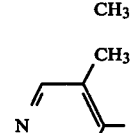 | —CH₃ | —CH₃ |
| 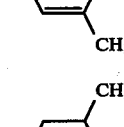 | —CH₃ | —C₂H₅ |

TABLE II-continued
| | | |
|---|---|---|
| 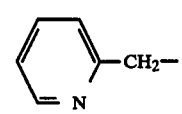 | H | H |
| 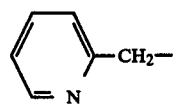 | H | —CH₃ |
| 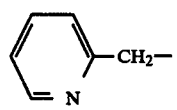 | H | —C₂H₅ |
| 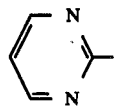 | H | H |
| 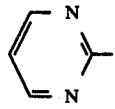 | H | —CH₃ |
| 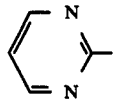 | —CH₃ | —CH₃ |
| 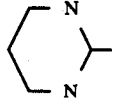 | —H | —CH₃ |
| 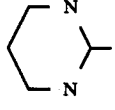 | —H | —C₂H₅ |
| 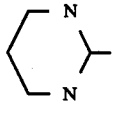 | —CH₃ | —CH₃ |
| 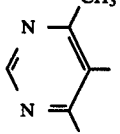 | H | H |
| 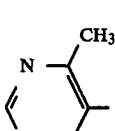 | H | —CH₃ |
TABLE II-continued
| | | |
|---|---|---|
| 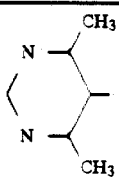 | —CH₃ | —CH₃ |
| 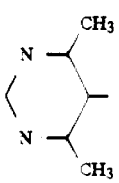 | H | —C₂H₅ |
| 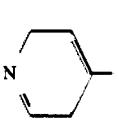 | H | H |
| 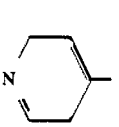 | H | —CH₃ |
| 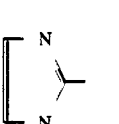 | H | H |
| 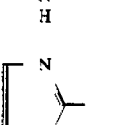 | H | —CH₃ |
| 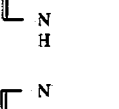 | H | —C₂H₅ |
| 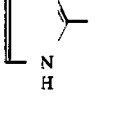 | H | H |
| 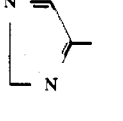 | H | —CH₃ |
| 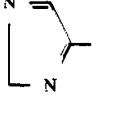 | H | —CH₃ |
| 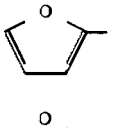 | H | H |
|  | H | —CH₃ |

TABLE II-continued

| Structure | R | R' |
|---|---|---|
| 3-furyl | H | —C$_2$H$_5$ |
| 2-thienyl | H | —CH$_3$ |
| 2-thienyl | —CH$_3$ | —CH$_3$ |
| 2-pyrrolyl | —H | —CH$_3$ |
| 2-pyrrolyl | —H | —C$_2$H$_5$ |
| 5-isoxazolyl | —H | —CH$_3$ |
| 5-isothiazolyl | H | —CH$_3$ |
| 5-isothiazolyl | H | —C$_2$H$_5$ |
| 5-isoxazolidinyl | H | —CH$_3$ |
| 2-(1,3-oxazinan-2-yl) | H | —C$_2$H$_5$ |
| 4-(1,3-oxazinan-4-yl) | H | —CH$_3$ |
| 4-(1,3-oxazinan-4-yl) | H | —C$_2$H$_5$ |
| 4-(1,3-thiazinan-4-yl) | H | —CH$_3$ |
| 2-(1,3-thiazinan-2-yl) | H | —C$_2$H$_5$ |
| 4-(1,3-thiazinan-4-yl) | H | —CH$_3$ |
| 2-(1,3-thiazinan-2-yl) | H | —C$_2$H$_5$ |
| 2,3-dimethylphenyl | H | 3-pyridyl |
| 2,3-dimethylphenyl | —CH$_3$ | 2-pyridyl |
| 2,3-dimethylphenyl | —CH$_3$ | 4-pyridyl |
| 2,3-dimethylphenyl | —CH$_3$ | 2-pyridyl |
| 2,3-diethylphenyl | —CH$_3$ | 2-pyridyl |
| 2-methyl-3-pyridyl | —CH$_3$ | 2-pyridyl |

$$\underset{\underset{O}{\|}}{R_1-N}\overset{CH=N}{\underset{N}{\diagdown}}\overset{R_{10}}{\diagdown}$$

| R$_1$ | R$_{10}$ |
|---|---|
| 2,3-dimethylphenyl | 1-pyrrolidinyl |

TABLE II-continued
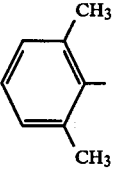 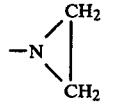
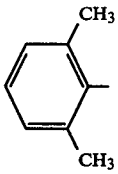 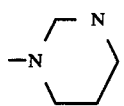
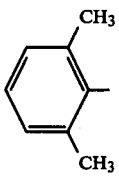 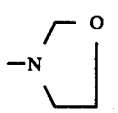
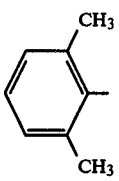 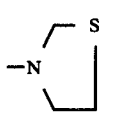
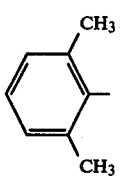 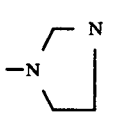
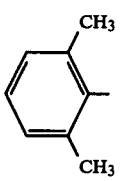 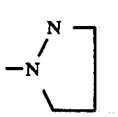
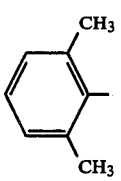 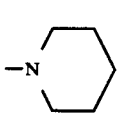
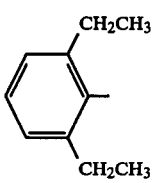 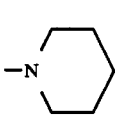
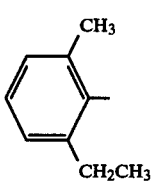 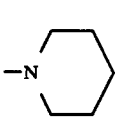
TABLE II-continued
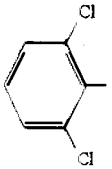 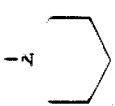
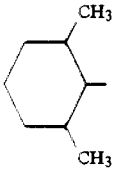 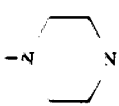
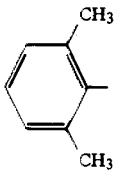 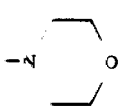
 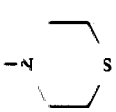
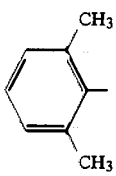 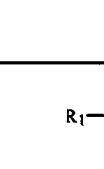
TABLE III
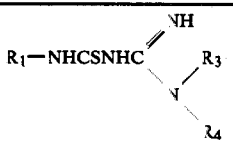
$R_1$—NHCSNHC
| $R_1$ | $R_3$ | $R_4$ |
|---|---|---|
| 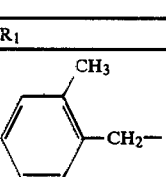 | H | —$CH_3$ |
| 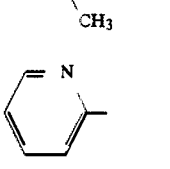 | H | —$CH_3$ |
| 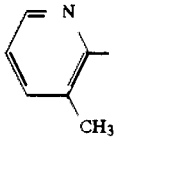 | H | —$CH_3$ |

TABLE III-continued $$R_1\text{—NHCSNHC}\overset{\displaystyle NH}{\underset{\displaystyle N\diagdown_{R_4}^{R_3}}{\|}}$$

| $R_1$ | | |
|---|---|---|
| 2,6-dimethylphenyl | H | pyridin-3-yl |
| 2,6-dimethylphenyl | —CH₃ | pyridin-2-yl |
| 2,6-dimethylphenyl | —H | piperidin-4-yl |

| $R_1$ | $-N\diagdown_{R_4}^{R_3}$ |
|---|---|
| 2,6-dimethylphenyl | piperidin-1-yl |
| 2,6-dimethylphenyl | morpholin-4-yl |
| 2,6-dimethylphenyl | piperidin-1-yl |

TABLE IV $$R_1\text{—N}\diagdown_{\underset{\displaystyle S}{\overset{\displaystyle CH=N}{C}}}^{CH=N}\text{—N}\diagdown_{R_4}^{R_3}$$

| $R_1$ | $R_3$ | $R_4$ |
|---|---|---|

TABLE IV-continued $$R_1\text{—N}\diagdown_{\underset{\displaystyle S}{\overset{\displaystyle CH=N}{C}}}^{CH=N}\text{—N}\diagdown_{R_4}^{R_3}$$

| $R_1$ | $R_3$ | $R_4$ |
|---|---|---|
| 2,6-dimethylbenzyl | H | —CH₃ |
| pyridin-2-yl | H | —CH₃ |
| 3-methylpyridin-2-yl | H | —CH₃ |
| 2,6-dimethylphenyl | H | pyridin-3-yl |
| 2,6-dimethylphenyl | —CH₃ | pyridin-2-yl |
| 2,6-dimethylphenyl | —H | piperidin-4-yl |

| $R_1$ | $-N\diagdown_{R_4}^{R_3}$ |
|---|---|
| 2,6-dimethylphenyl | piperidin-1-yl |
| 2,6-dimethylphenyl | morpholin-4-yl |

TABLE IV-continued

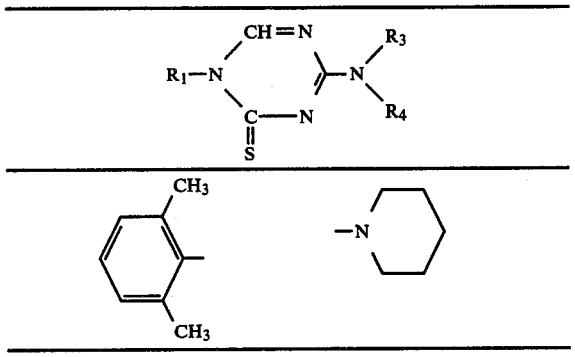

In accordance with the analytical process aspect of this invention, the gas chromatographic separations are carried out in packed columns prepared according to known methods. Such methods are described for example in *Methods of Biochemical Analysis* Vol. II., Ed.; D. Glick, Inter-Science, New York, 1963.

Generally speaking, the gas chromatographic assay method is carried out by subjecting a sample containing an amidinourea to the derivatizing reaction as disclosed herein and injecting the derivatized sample into the inlet port of a gas chromatograph of conventional design. The separation is readily achieved on either a GSC or GLC column using known methods such as described, for example, in *Analytical Letters* 5 (8) at page 521, the disclosure of which is hereby incorporated by reference. Suitable fixed phase materials for the GC can be chosen from commercially available column packing materials. For quantitative assays, an internal reference standard is employed to develop a calibration curve. Suitable materials for use as internal reference standards are, for example, triphenylethylene and tetraphenylethylene which give good separations when mixed with amidinourea samples. The derivatization of an amidinourea containing sample is done in accordance with the derivatizing method of this invention and is conveniently carried out on small samples by simply mixing with the derivatizing reagent in a sealed vial, preferably in a suitable solvent such as DMF and assisted by heating.

In addition to their use as derivatives for gas chromatographic analysis, the 1-aryl-1,2-dihydro-1,3,5-triazin-2-ones and thiones of this invention have been shown to possess useful pharmacological properties which can be advantageously used by administering the compounds to humans for a variety of therapeutic benefits without harm.

1-aryl-1,2-dihydro-2-triazine derivatives are known to possess a broad spectrum of biological activity (Heterocyclic Compounds, Vol. 7, John Wiley & Sons, Inc., 1961, p. 717-718). The novel compounds of this invention constitute a new class of 1-aryl-1,2-dihydro-2-triazines, particularly 1-aryl-1,2-dihydro-1,3,5-triazin-2-ones which similarly have a broad spectrum of biological activity. Thus, these compounds have demonstrated useful gastrointestinal actions and can be used for example as antidiarrheal agents for the treatment of gastrointestinal disorders. Whereas amidinoureas also have local anesthetic and other pharmacological effects when administered at dose levels for effective antidiarrheal action, certain of the novel triazinones show good antidiarrheal activity without local anesthetic or other side effects at active dose levels. Certain of the novel triazine derivatives have shown other gastrogenic and related effects, particularly antisecretory action, making them useful in the treatment of such gastrointestinal disorders as peptic ulcers. Compounds of this series have also shown anti-motility and spasmolytic effects making them useful in the control of muscle spasm particularly stomach or intestinal spasms. Certain of the compounds have also been found to exhibit novel effects on nerve impulse transmissions wherein single impulse nerve transmissions are unaffected while multiple high frequency nerve transmissions are blocked.

The amidinoureas from which the novel triazine derivatives are prepared according to this invention are known to possess useful pharmacological properties including antidiarrheal activity in mammalian species. Generally, it has been found that the antidiarrheal properties of the amidinourea are not lost in cyclizing to the corresponding triazine derivative. Accordingly, the novel triazine derivatives of this invention are also useful antidiarrheal agents as shown by test results in animals which, based on previous experience with the corresponding amidinoureas, show good correlation to activity in humans.

Various tests can be carried out in animal models to show the ability of the amidinoureas of this invention to exhibit reactions that can be correlated with anti-diarrheal activity in humans. The following tests show the ability of the compounds of this invention to inhibit diarrhea in animals and are known to correlate well with antidiarrheal activity in humans. These are considered to be standard tests used to determine antidiarrhea properties. This correlation can be shown by the activities of compounds known to be clinically active. In view of results with these tests, the novel 1,3,5-triazin-2-ones and 1,3,5-triazin-2-thiones of this invention can be considered to be anti-diarrheal agents.

The test compound is dissolved in distilled water, unless otherwise stated. The $ED_{50}$ values and 95% confidence limits are calculated according to a method described by D. F. Finney (Probit Analysis, 2nd Ed., University Press, Cambridge, p. 236, 1964).

1. Antagonism of Castor Oil-induced Diarrhea in Mice

A modified test described by Niemegeers et al. (Arzneim-Forscth 22, 516-518, 1972) was used. Groups of ten male Swiss Webster mice (22-25 g) were randomly selected for dosing. Castor oil (Fischer Scientific Co.), 0.3 ml/mouse, was given orally one hour after an oral dose of test compound or the vehicle. After dosing with castor oil, each mouse was placed into an individual wire cage and observed for six hours for diarrhea.

2. Antagonism of Castor Oil-induced Diarrhea in Rats

A test described by Niemegeers et al. (supra) was used. Groups of ten female Wistar rats (180-200 g) were randomly selected for dosing. In addition, groups of ten female Sprague-Dawly rats (180-200 g) were used to determine strain difference. Castor oil (Fisher Scienfitic Co.), 1 ml/rat, was given orally one hour after an oral dose of test compound or the vehicle. After dosing with castor oil, each rat was placed into an individual wire cage and observed for six hours for diarrhea.

3. Antagonism of Chemically-induced Diarrhea in Mice

Male Swiss Webster mice (18-22 g) in groups of 10-20 mice were randomly selected for oral dosing with test compound or the vehicle one hour before the intraperitoneal injection of either 400 μg/kg of Carbachol (carbamycholine chloride, Sigma Chemical Co., St. Louis, Mo.); or, 200 μg/kg of serotonin creatinine sulfate (Schwartz/Mann Biochemicals, Orangeburg, N.Y.). After each mouse was injected, it was placed into an individual wire cage and observed for diarrhea.

4. Inhibition of the Gastrointestinal Transit Time of a Charcoal Meal in Mice

A charcoal suspension (10 ml/kg of a 10% suspension) was given orally to groups of ten Swiss Webster male mice (18–22 g) one hour after an oral dose of test compound or vehicle. The mice were sacrificed by cervical dislocation 30 minutes after the charcoal meal and the distance in millimeters that the charcoal meal traveled through the small intestine was measured and compared to the controls.

$$\frac{\text{Mean distance in controls} - \text{mean distance in treated}}{\text{Mean distance in controls}} \times 100 = \% \text{ Inhibition}$$

5. The Effect of Naloxone on the Inhibitory Actions of Triazinones on Gastrointestinal Motility Male Swiss Webster mice (18–20 g) in groups of ten were randomly selected for dosing with test compound or the vehicle alone and concomitantly with naloxone. The naloxone was dissolved in saline.

The mice were given a charcoal meal (10 ml/kg of a 10% suspension) one hour after an oral does of the vehicle or a test compound(s). Thiety minutes after the charcoal meal the mice were sacrificed by cervical dislocation and the distance in millimeters that the charcoal meal traveled through the small intestine was measured and compared to the controls.

6. Fecal Output Tolerance Study in Rats

Male Wistar rats (140–180 g) were given oral doses of either test compound, diphenoxylate HCl (suspended in methylcellulose or the vehicle (distilled water or methyl-cellulose) once a day for five consecutive days. Vehicle or the test compound were given daily 30 minutes before fecal collection. The feces were collected in a completely automated four-tiered metabolic cage over a 12-hour period consisting of three, four-hour intervals. Following collection, the feces were dried for four hours at 200° C. and weighed.

7. Prostaglandin test

An intraperitoneal injection of 100 micrograms per kilogram of PGE$_2$ causes diarrhea in mice within ten minutes. Groups of mice were orally dosed with test compound at various dose levels after which the PGE$_2$ is given and ten minutes later the mice are checked for diarrhea to determine the ED$_{50}$.

Representative compounds of Formula I when subjected to testing in accordance with the above methods showed antidiarrheal activity comparable to that of the corresponding amidinoureas.

The results with a representative novel triazinone [1-(2',6'-dimethylphenyl)-4-methylamino-1,2-dihydro-1,3,5-triazin-2-one hydrochloride] are as follows.

1. Antagonism of Castor Oil-induced Diarrhea in Mice

An oral dose of 0.3 mls of castor oil caused diarrhea in 20 control mice within three hours. Test compound, given to ten mice per dose level one hour before an oral dose of castor oil, protected the mice from diarrhea in a dose-related way over a period of six hours.

2. Antagonism of Castor Oil-induced Diarrhea in Rats 1-(2',6'-dimethylphenyl)-4-methylamino-1,2-dihydro-1,3,5-triazin-2-one hydrochloride protected castor oil treated Wistar and Sprague-Dawley female rats from diarrhea. The compounds have a potency ratio which compares favorably with diphenoxylate and loperamide with duration of action better sustained.

3. Antagonism of Chemically-induced Diarrhea

Serotonin injected intraperitoneally at 200 µg/kg caused diarrhea in 15 control mice within 15 minutes after its injection. 1-(2',6-dimethylphenyl)-4-methylamino-1,2-dihydro-1,3,5-triazin-2-one hydrochloride given orally to ten mice per dose level protected the mice from serotonin-induced diarrhea.

An intraperitoneal injection of 400 µg/kg of carbachol caused diarrhea in 15 control mice within 20 minutes after its injection. 1-(2',6'-dimethylphenyl)-4-methylamino-1,2-dihydro-1,3,5-triazin-2-one hydrochloride given orally to five or ten mice per dose level protected the mice from carbachol-induced diarrhea.

4. Inhibition of the Gastrointestinal Transit Time of a Charcoal Meal in Mice

Twenty mice were used as controls and ten mice at each dose level. Inhibition with 1-(2',6'-dimethylphenyl)-4-methylamino-1,2-dihydro-1,3,5-triazin-2-one hydrochloride was dose-related.

5. The Effect of Naloxone on the Inhibitory Actions of 1-(2,6-dimethylphenyl)-3-methylamino-1,2-dihydro-1,3,5-triazin-2-one hydrochloride Naloxone is a well-known specific antagonist of morphine-like compounds. As previously reported, diphenoxylate was antagonized by naloxone competitively in the charcoal meal test. Naloxone had no effect on the actions of 1-(2',6'-dimethylphenyl)-4-methylamino-1,2-dihydro-1,3,5-triazin-2-one hydrochloride. The dose of naloxone used in this test did not, by itself, change the gastrointestinal transit time of a charcoal meal.

6. Fecal Output Tolerance Study in Rats

Groups of rats, five in each group, were given 1-(2',6'-dimethylphenyl)-4-methylamino-1,2-dihydro-1,3,5-triazin-2-one hydrochloride, 30 mg/kg, and diphenoxylate, 5 mg/kg. for five consecutive days. The triazinone showed no tolerance over the five day period, while diphenoxylate caused a decrease in activity starting on day 2 and continuing through day 5. After 5 days, diphenoxylate had lost 72% of its original activity seen on day 1.

7. Antagonism of Prostaglandin E$_2$ (PGE$_2$)-induced Diarrhea in Mice

An intraperitoneal injection of 100 µg/kg PGE$_3$ (Analabs Inc., North Haven, Conn.) caused diarrhea in 15 control mice within 15 minutes after its injection. 1-(2',6'-dimethylphenyl)-4-methylamino-1,2-dihydro-1,3,5-trizin-2-one hydrochloride given orally to ten mice per dose level protected the mice from PGE$_3$-induced diarrhea in a dose-related way.

The amidinourea starting materials, in addition to having antidiarrheal properties, are also known to possess other pharmacological activities such as local anesthetic and cardiovascular activity. Unlike the amidinoureas which generally have local anesthetic properties, the pharmaceutically useful 1-aryl-1,2-dihydro-1,3,5-triazin-2-ones and thiones of this invention have been found to be more specific and surprisingly effective antidiarrheal doses show little or no classical local anesthetic effects nor do they show any significant cardiovascular effects. The compounds of Formula I are particularly useful as antidiarrheal agents where it is desirable to achieve an antidiarrheal effect with a minimum of side effects and these compounds are therefore especially suited to the treatment of gastrogenic diarrhea. A preferred subclass of novel triazine derivatives having these properties are represented by the formula

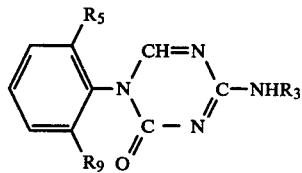

VI wherein:
R$_3$ is hydrogen,
  loweralkyl or
  loweralkoxy;
R$_5$ and R$_9$ are each independently loweralkyl,
  halo,
  nitro,
  loweralkoxy or
  hydroxyloweralkyl.

Compounds where R$_5$ and R$_9$ are loweralkyl of 1 to 4 C-atoms are especially preferred.

The tests employed to determine the separation of local anesthetic and cardiovascular activity at effective antidiarrheal doses with representative compounds of the formula above are as follows:

Several different procedures generally employed in testing for local anesthetic activity are used to determine local anesthetic effects. These tests have been used extensively in the past and have given satisfactory results in defining the local anesthetic properties of compounds.

A discussion of experimental methods for evaluating local anesthetic properties of drugs is found in *Evaluation of Drug Activities: Pharmacometrics*, Vol. 1, Ed by D. R. Lawrence and A. L. Bacharach, Academic Press, Inc. (London) Ltd. (1964). Applicants herewith incorporate by reference Chapter 9 of this book entitled "Local Anesthetics", pages 204–214.

Tests which show the lack of side effects of the preferred antidiarrheal triazinones include the following.

1. Effect on Hexobarbital-induced Loss of Righting Reflex 1-(2',6'-dimethylphenyl)-4-methylamino-1,2-dihydro-1,3,5-triazin-2-one hydrochloride and a vehicle given orally 30 minutes before hexobarbital were compared for their effect on the duration of the loss of righting reflex (failure to right within five seconds) induced in groups of Swiss Webster mice (10/group, 18–20 g) by the intraperitoneal injection of hexobarbital (100 mg/kg, I.P.).

2. Effect on Plasma Glucose in Rats

Groups of 5–10 male Sprague-Dawley rats (170–210 g) were orally dosed with 1-(2',6'-dimethylphenyl)-b 4-methylamino-1,2-dihydro-1,3,5-triazin-2-one hydrochloride or the vehicle. Three hours after dosing, the rats were sacrificed by decapitation and blood was collected for plasma glucose evaluation.

3. Effect on Inducing Emesis in Dogs

Female beagle dogs (6.0–10 kg) were randomly selected for intravenous dosing with 1-(2',6'-dimethylphenyl)-4-methylamino-1,2-dihydro-1,3,5-triazin-2-one hydrochloride. Each dose of the test compounds was given to either two or four dogs. Immediately after the injection, the dogs were observed for emesis for a period of up to one hour.

The results with a representative triazinone are as follows:

1. Effect on Hexobarbital-induced Loss of Righting Reflex 1-(2',6'-dimethylphenyl)-4-methylamino-1,2-dihydro-1,3,5-triazin-2-one hydrochloride in doses as great as four times the ED$_{100}$ dose in the castor oil test in mice, had no effect on the duration of hexobarbital-induced loss of righting reflex.

2. Effect on Plasma Glucose in Rats

Groups of rats, five per group, were given oral doses of 1-(2',6'-dimethylphenyl)-4-methylamino-1,2-dihydro-1,3,5-triazin-2-one hydrochloride. A dose-related elevation of plasma glucose resulted.

3. Effect on Inducing Emesis in Dogs

There is a marked difference between 1-(2',6'-dimethylphenyl)-4-methylamino-1,2-dihydro-1,3,5-triazin-2-one hydrochloride and the corresponding amidinourea in causing emesis in beagle dogs. 1-(2',6'-dimethylphenyl)-4-methylamino-1,2-dihydro-1,3,5-triazin-2-one hydrochloride caused no emesis, at doses ten times the dose of the amidinourea within a three minute period following i.v. administration.

Various tests and the results intended to illustrate the effects of the triazinones on the cardiovascular system are given below.

Cardiovascular Activity of 1-(2',6'-dimethylphenyl)-4-methylamino-1,2-dihydro-1,3,5-triazin-2-one hydrochloride Intravenous doses of 1-(2',6'-dimethylphenyl)-4-methylamino-1,2-dihydro-1,3,5-triazin-2-one hydrochloride at antidiarrheally effective levels did not significantly change arterial blood pressure, but produced moderate reductions in heart rate. Sympathetically-mediated cardiovascular reflex activity was only slightly reduced. Blood pressure responses to challenge doses of autonomic agonists were not significantly changed.

Antiarrhythmic Effects in Ouabain-intoxicated Dogs

Following ouabain intoxication, one dog received an I.V. infusion of 1-(2',6'-dimethylphenyl)-4-methylamino-1,2-dihydro-1,3,5-triazin-2-one hydrochloride. After the total dose was infused, the heart rate was slightly reduced and the bloood pressure elevated in association with partial conversion from ectopic ventricular tachycardia to a primarily nodal rhythm. A second day dog received an I.V. infusion of 1-(2',6'-dimethylphenyl)-4-methylamino-1,2-dihydro-1,3,5-triazin-2-one hydrochloride, at a higher rate. In this dog, heart rate was slightly reduced and blood pressure was elevated following the infusion, but there was no conversion from the ouabain-intoxicated dogs receiving the corresponding amidinourea consistently converted to normal sinum rhythm at lower total doses.

Local Anesthetic Effects in Guinea Pigs

Intradermal injections of 1-(2'6'-dimethylphenyl)-4-methylamino-1,2-dihydro-1,3,5-triazin-2-one hydrochloride as a 0.25% solution were essentially ineffective in protecting against dermal pain responses. Higher concentration gave some protection.

An additional test method used to examine the unique local anesthetic activity of the novel triazine compounds of this invention involves direct application to the isolated desheathed sciatic-perineal-tibial trunk of the bullfrog. The methodology used is as follows:

All drug solutions were applied to 15 mm segments of desheathed trunks situated betwen stimulating and recording electrodes employing a standard pharmacologic technique for observing the conduction blocking effects of local anesthetics.

Briefly summarized, the technique allows nerve impulses to be initiated by means of an electrical stimulus applied to a drug-free segment of a trunk and to be conducted through the treated segment. Recording electrodes placed on the distal side of the treated segment detect only those impulses that were conducted through the 15 mm segment. By relating the amplitude of the recorded compound spike potential to that recorded before the application of drug treatment, an index is available for the proportion of fibers that could conduct impulses through 15 mm of treated length. This index is referred to as "percent of control spike height" or "percent reduction of spike height" or "percent block of conduction".

The source of the nerves is the bullfrog, *Rana castesbeiana*. During dissection, the nerves are exposed to Ringer solution having the following composition: 110 mM NaCl, 3.0 mM KCl, 1.8 mM $CaCl_2$, 20 mM $NaHCO_3$, 2 mN phosphate buffer. The solution is bubbled with 95% $O_2$, 5% $CO_2$ to maintain a pH of 7.2±0.05 at room temperature (22°-24° C.).

Preparation of Ringer solution with test substance:

First, a quantity of drug is weighed out which would make a 50 mM solution when dissolved in 5.0 ml of Ringer. The drug is dissolved in 0.4 ml of absolute ethanol by stirring for 10 minutes at high speed on a Genie Vortex apparatus. The solution is then brought to 5.0 ml with standard Ringer solution. The drug solution is then diluted 10 times with Ringer solution to give a final concentration of 5.0 mM. The final solution is bubbled with 95% $O_2$, 5% $CO_2$ to give a pH of 7.2. The final concentration of ethanol is 0.172 M.

To control for the ethanol in the drug solution, the drug-free Ringer solution used to recover nerves from drug effect was made with the same final concentration of ethanol. This ethanol had no effect on conduction.

The same general procedure was used to prepare a solution of the test drug in a dimethylsulfoxide Ringer solution. The final concentration of dimethylsulfoxide (DMSO) was 0.101 M. DMSO had no effect on conduction.

Representative compounds of Formula I when tested by this method showed the following results.

1-(2',6'-dimethylphenyl)-4-methylamino-1,2-dihydro-1,3,5-triazin-2-one hydrochloride proved to have essentially no conduction blocking action at a concentration of 5 mM, which is the high end of concentrations used on desheathed frog trunks with bonafide local anesthetic agents. In 4 separate experiments, the average reduction in the A B spike potential was only 10%±1.6 (S.E.M.) after 30 minutes contact with the drug. This feeble effect is contrasted with that of 5 mM of the corresponding amidino urea which caused a mean reduction of 77%±8.3 (N=3) within 10 minutes of contact; and a total block within 20 minutes in 2 of 3 trunks.

This test shows 1-(2',6'-dimethylphenyl)-4-methylamino-1,2-dihydro-1,3,5-triazin-2-one hydrochloride to be devoid of any important local anesthetic activity on bullfrog peripheral nerves of the A B classification. Accordingly, this class of compounds find use in the treatment of diarrhea without causing side effects particularly local anesthesia.

Still another useful subclass of 2-triazine derivatives are those which possess unique local nerve/muscles effects. In particular, certain of the derivatives have been found to be capable of differentiated responses to single impulse and high frequency stimulation in nerve transmission of electrical impulses. Thus, a particular group of novel 2-triazine derivatives have been shown to produce complete blocking of high frequency stimulation while permitting complete transmission of single impulse stimulation. Accordingly, these compounds are useful in those clinical situations where excitable nerve membrane is spontaneously activated at exaggerated rates. Under such conditions, this particular group of novel triazine derivatives can be utilized to limit the exaggerated rate without limiting the original impulse. In view of the unique pharmacological effects of certain of these compounds they provide an effective tool for use in the study and understanding of muscle fiber excitation and nerve impulse transmission. Compounds which have been found to be particularly useful for their ability to block high frequency impulse stimulation are compounds of the general formula:

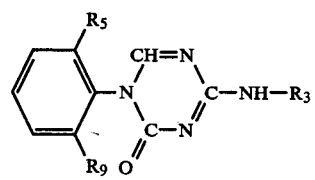

VII wherein:
$R_3$ is hydrogen,
 loweralkyl or
 loweralkoxy; and
$R_5$ and $R_9$ are each separately loweralkyl of 2 to 6 carbon atoms.

The test employed in showing the differentiated local anesthetic activity between single impulse blocking and blocking of high frequency electrical stimulation and the results with representative compounds of the above formula are given below. The methodology is substantially the same desheathed nerve test as that described above.

In this test 1-(2',6'-diethylphenyl)-4-methylamino-1,2-dihydro-1,3,5-triazin-2-one hydrochloride was found to possess weak conduction blocking properties on isolated bullfrog nerves, but to have a substantial capacity to produce high frequency failure (h.f.f.).

At a concentration of 5 mM 1-(2',6'-diethylphenyl)-4-methylamino-1,2-dihydro-1,3,5-triazin-2-one hydrochloride reduces the amplitude of a single compound spike by 19%±2.4 in 30 minutes (N=6). This minimal amount of conduction block with 5 mM of the triazine is to be contrasted with an 82%±13.4 (N=3) block within 3 minutes with the corresponding amidino urea.

This difference is illustrated by a comparison of the effects and time-course of 1-(2',6'-diethylphenyl)-4-methylamidinourea (5 mM) with the corresponding cyclized derivative (5 mM) applied to the left and right trunks from the same animal. The amidinourea at this concentration caused a complete block of conduction within 3 minutes; and the triazinone caused only a minimal block of conduction of single impulses. With continued contact, however, the triazinone produced its characteristic h.f.f. which developed slowly but continually.

Recovery from h.f.f. effects of the triazinone were fairly rapid as shown by good recovery in 10 minutes and nearly complete recovery in 30 minutes.

Clearly, the triazinone has very weak blocking action, and in relation to the corresponding amidinourea, is virtually inactive in depressing excitability under widely spaced stimuli. This compound, therefore, reflects a dissociation between simple conduction block and high frequency failure.

1-(2',6'-diethylphenyl)-4-methylamino-1,2-dihydro-1,3,5-triazin-2-one hydrochloride was also compared with lidocaine in 2 trunks. By comparing 1(2',6'-diethylphenyl)-4-methylamino-1,2-dihydro-1,3,5-triazin-2-one hydrochloride with lidocaine on the same trunk, the experiment was biased in favor of the triazinone showing any conduction blocking effect, yet it showed no block of single impulses at 5 mM, whereas lidocaine showed blockade at 0.75 and 1.0 mM concentrations. Hence, 1-(2',6'-diethylphenyl)-4-methylamino-1,2-dihydro-1,3,5-triazin-2-one hydrochloride is virtually without conduction blocking action; and is less than 1/5 as active as lidocaine on h.f.f. (The apparently low potency of lidocaine in this trunk is most likely due to the use of "winter" frogs whose sensitivity to local anesthetics is reduced in comparison to "summer" frogs.

Since 1-(2',6'-diethylphenyl)-4-methylamino-1,2-dihydro-1,3,5-triazin-2-one hydrochloride is poorly soluble in Ringer solution, it was dissolved first in either of two solvents, DMSO or ethanol. Nearly all the experiments were done using ethanol as the initial solvent, but the results were obtained using the triazinone with 2 different solvents in a pair of trunks from the same animal. Ethanol or DMSO were present in their respective concentrations in both the triazinone solutions and in the normal, drug-free Ringer solution used in the recovery of the nerves. The results show that neither of the two solvents were responsible for the nerve membrane effects observed.

1-(2',6'-diethylphenyl)-4-methylamino-1,2-dihydro-1,3,5-triazin-2-one hydrochloride is virtually without blocking action in nerves stimulated at a low frequency, i.e., 0.5 Hz, at a concentration of 5 mM. The average reduction in the compound spike of only 20% in 30 minutes stands in marked contrast to the total block within a few minutes by 5 mM 1-(2',6'-diethylphenyl)-3-methylamidinourea, its amidinourea precurror.

1-(2',6'-diethylphenyl)-4-methylamino-1,2-dihydro-1,3,5-triazin-2-one hydrochloride has a substantial effect on the membrane recovery processes as evidenced by the development of high frequency failure. This phenomenon is associated with the prolongation of the refractory period of the membrane which, in turn, limits the nerve in its ability to respond to repetitive stimulation at higher frequencies.

In elaborating the above described pharmacological properties of the triazin-2-ones and triazin-2-thiones of this invention particularly the useful antidiarrheal properties, it was found that certain of the compounds show differentiated levels of effectiveness as antisecretory or antimotility agents when administered in generally used tests in laboratory animals which tests are known to correlate to human application. The test utilized in establishing the antisecretory activity of the triazine derivatives and results with one of the compounds preferred for use as an antisecretory agent are as follows:

Inhibition of Gastric Acid Secretion in the Rat

The method used has been reported by Shay. Male Sprague-Dawley rats (140–160 g) were fasted 24 hours prior to the test. The rats were allowed water ad libitum only during the fasting period. One hour before pyloric ligation the rats (5/group) were given either 1-(2',6'-dimethylphenyl)-4-methylamino-1,2-dihydro-1,3,5-triazin-2-one hydrochloride, atropine sulfate or the vehicle. The compounds were prepared in methylcellulose. Pyloric ligation was performed in the rats under sodium methohexital anesthesia. Four hours after pyloric ligation the rats were sacrificed by several dislocation, the stomachs were removed and the gastric contents were assayed for volume, titratable acidity, and titratable acid output (TAO). A 1 ml aliquot of the gastric contents was titrated with 0.1 N naOH to pH 7.0 for titratable acidity. The percent of inhibition was calculated according to the formula:

$$\frac{\text{Mean control} - \text{mean treated}}{\text{Mean control}} \times 100$$

The antisecretory effects of compounds of Formula I is shown by the results with a representative triazinone. 1-(2',6'-dimethylphenyl)-4-methylamino-1,2-dihydro-1,3,5-triazin-2-one hydrochloride inhibited gastric acid secretion by the Shay rat as follows: Oral dose mg/kg., 20; No. of rats, 5; Volume, 81; Concentration, 78; Total Acid Output, 96. In contrast to atropine, a specific anticholinergic drug which caused mydriasis at doses as low as 2 mg/kg., 1-(2',6'-dimethylphenyl)-4-methylamino-1,2-dihydro-1,3,5-triazin-2-one hydrochloride was devoid of the mydriatic effect at 20 and 16 mg/kg., respectively.

Compounds of this invention which show antisecretory activity, particularly those in which the antisecretory effects are obtained at dose rates that produce little or no other effects, are especially useful in the treatment of gastrointestinal problems resulting from abnormal secretory action. A preferred group of compounds for use as differentiated antisecretory agents may be represented by the following formula:

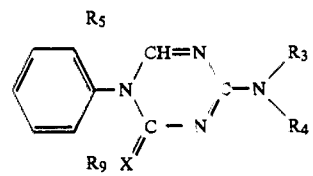

wherein:
X is oxygen or sulfur (preferably oxygen);
$R_3$ and $R_4$ have the same meaning as above; and
$R_5$ and $R_9$ are each independently loweralkyl of 2 to 6 carbon atoms; or
halo.

As indicated, the compounds of the above formula suppress acid secretion with little or no side effects by acting on those parts of mammalian systems which control gastric secretions thereby aiding in the prevention and alleviation of such disorders as gastritis and ulcers.

Generally speaking, the antidiarrheal compounds of this invention also exhibit the ability to suppress gastric motility and among them a preferred group which generally show good anti-motility also have useful antispasmodic effects making them suitable as spasmolytic agents at dose levels below which any other effects are exhibited. A preferred group of compounds for use as spasmolytics are the compounds of the formula:

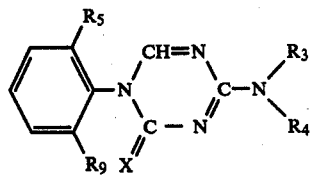

wherein:
X is oxygen or sulfur (preferably oxygen);
$R_3$ and $R_4$ are hydrogen,
   loweralkyl or
   loweralkoxy; and
$R_5$ and $R_9$ are each loweralkyl, loweralkoxy or halo.

In general, compounds of formula I are indicated for use as pharmacotherapeutic agent in a wide variety of mammalian conditions which require relief of symptoms or altering the action of the gastrointestinal or neuro-muscular systems. These compounds when used for example, as antidiarrheal, antisecretory or antispasmodic agents, are found to be effective for these purposes when administered orally and/or parenterally. The term "parenteral" as used herein includes intravenous, intramuscular, intraperatoneal and the like injection or infusion techniques.

The dosage regimens in carrying out the pharmacotherapeutic methods utilizing the triazin-2-ones and triazin-2-thiones of this invention are those which insure maximum therapeutic response until improvement is obtained and thereafter the minimum effective level which gives relief. Thus, in general, the dosages are those that are therapeutically effective in the treatment of diarrhea and related gastrointestinal disorders. In general, the oral daily dose can be between about 0.1 mg/kg and 70 mg/kg (preferably in the range of 0.5–50 mg/kg/day), bearing in mind, of course, that in selecting the appropriate dosage in any specific case, consideration must be given to the patient's weight, general health, age, and other factors which may influence response to the drug.

Compositions intended for oral use may be prepared according to any method known to the art for the manufacture of pharmaceutical compositions and such compositions may contain one or more agents selected from the group consisting of sweetening agents, flavoring agents, coloring agents and preserving agents, in order to provide a pharmaceutically elegant and palatable preparation. Orally, they may be administered in tablets, aqueous or oily suspensions, dispersible powders or granules, emulsions, hard or soft capsules, or syrups or elixers. Tablets which contain the active ingredient in admixture with non-toxic pharmaceutically acceptable excipients are suitable for the manufacture of tablets. These excipients may be, for example, inert diluents, for example, calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. The tablets may be uncoated or they may be coated by known techniques to delay disintegration and absorption.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active substance and similar compositions formulated for ease of administration depending upon the particular therapeutic or prophylatic objective form a separate development with respect to the active compound disclosed herein. Excipients suitable for aqueous suspensions, may be employed if desired. These excipients are suspending agents, for example, sodium carboxymethyl-cellulose, methyl-cellulose, hydroxypropylmethylcellulose, sodium alginate, polyvinylpyrrolidine, gum tragacanth and gum acacia; dispersing or wetting agents may be a naturally occurring phosphatide, for example, lecithin; or condensation products of an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol monooleate; or condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occuring phosphatides, for example, soya bean lecithin, and esters or partial esters derived from fatty acids and hexitol anhydrides, for example, sorbitan mono-oleage. The emulsions may also contain sweeping and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as an aqueous solution buffered to a pH of 4.0 to 7.0 and made isotonic with sodium chloride.

Further, the active triazine may be administered alone or in admixture with other agents having the same or different pharmacological properties.

Further, these compounds may be tableted or otherwise formulated for oral use so that for every 100 parts by weight of the composition, there are present between 5 and 95 parts by weight of the active ingredient. The dosage unit form will generally contain between about 1 mg. and about 500 mg. of the active ingredients of this invention. The preferred unit dose is between about 10 mg. and about 100 mg. The compositions may be taken 1-8 times daily depending on the dosage unit required.

Parenteral administration may be carried out using comparative dosages taken from the oral compositions. In general, the parenteral dosage will be less than the oral dose and normally within the range of ½ to 1/10 the oral dose but, of course, this would depend on the absorption characteristics of the compound employed. Dosages would be in the customary manner; however, in general, parenteral administration may be carried out neat or the compound may be utilized with a sterile vehicle as mentioned above. Dosage unit forms between 1 mg. and 500 mg. and preferably in the range of 10 mg. and 100 mg. are useful. The daily parenteral dose would be between 0.1 mg/Kg/day and 70 mg/Kg/day and preferably in the range of 0.5 mg/Kg and 50 mg/Kg/day.

The compounds of this invention are also useful as veterinary medicines. In particular, these compounds are useful in the treatment of animal scours, particularly in food animals. When administered in suitable formulations, for example, as additives to food or water, these compounds prevent or relieve scours in lambs, calves, piglets and fowls.

EXAMPLE 1

Derivatization of 1-(2',6'-dimethylphenyl)-3-methylamidinourea is carried out by dissolving about 10 mg. of 1-(2',6'-dimethylphenyl)-3-methylamidinourea hydrochloride in 1 ml. of dimethylformamide and adding 0.1 ml. of dimethylformamide dimethylacetal in a 1 ml. hpyo-vial. The vial is sealed with a silicone rubber septum. The mixture is shaken and 2 μl of it is injected into a gas chromatograph (G.C.)

Instrument Conditions:
Column: 6'×4 mm I.D., glass, 10% Se-30 on Chromosorb W (AW-DMCS) H.P.
Oven Temperature: 250° C.
Injection Port Temperature: 270° C.
Detector Temperature: 270° C.
Carrier Gas: $N_2$, 45 ml/min.
Range: $10^3$
Recorder Presentation: 100 mv full scale
Injection Volume: 2.0 μl The best separation of the 1-(2',6'-dimethylphenyl)-3-methylamidinourea derivative ($t_R$=5.5 min.) from the solvent peak is achieved on an SE-30 column. Tetraphenylethylene ($t_R$=4.7 min.) is chosen as an internal standard, since it gives a well shaped peak and does not interfere with other peaks. Triphenylmethane ($t_R$=10.1 min.) may also be used as an internal standard.

To evaluate optimum derivatization temperature and time, a sample containing 1-(2',6'-dimethylphenyl)-3-methylamidinourea hydrochloride and triphenylethylene is derivatized and the mixture is injected into G.C. The peak area ratio of 1-(2',6'-dimethylphenyl)-3-methylamidinourea derivative to that of the internal standard is followed up to three hours at room temperature. It is found that the derivatization is not complete during the period of time. The same experiment at an elevated temperature (110° C.) gives complete derivatization within 16 minutes.

Dimethylformamide is chosen as the solvent because it is a relatively good solvent for both 1-(2',6'-dimethylphenyl)-4-methylamidinourea hydrochloride and triphenylethylene or tetraphenylethylene and has a high boiling point (153° C.).

EXAMPLE 2

Derivatized samples are prepared in the following manner. About 10 mg. of the appropriate amidinourea are weighed out and dissolved in a 1 ml. hypo-vial in 1 ml. of DMF. The internal standard (triphenylethylene or tetraphenylethylene) is then added using as much as ⅓ of the sample weight. 0.1 ml. of dimethylformamide dimethylacetal is added with a syringe. The vial is sealed with a crimper and shaken. The vial is placed in an oven at about 105°-110° C. for 20 minutes. Analysis is run by injecting 2.0 μl, in duplicate, into the inlet port of the G.C.

To evaluate the response linearity of the G.C. process, mixtures containing 4.5, 9.0, 13.5, 18.0 and 22.5 mg. of 1-(2',6'-dimethylphenyl)-4-methylamidinourea hydrochloride and 3.5 mg. of triphenylethylene are derivatized at 110° C. in an oven for 20 minutes and chromatographed. A plot of the peak area ratio of 1-(2',6'-dimethylphenyl)-4-methylamidinourea derivative to that of the internal standard against the concentration of 1-(2',6'-dimethylphenyl)-3-methylamidinourea hydrochloride in the mixture shows a linear relationship. Mixtures containing below 5 mg. level of 1-(2',6'-dimethylphenyl)-4-methylamidinourea hydrochloride and the internal standard (0.9, 1.8, 2.7 and 3.6 mg. of 1-(2',6'-dimethylphenyl)-4-methylamidinourea hydrochloride and 0.7 mg. of triphenylethylene) also show a linearity. In both cases, however, the lines have negative intercepts indicating that some of 1-(2',6'-dimethylphenyl)-3-methylamidinourea derivative is absorbed on the column. The G.C. method, therefore, should be used with a calibration curve of more than two points.

Instrument Conditions:
Column: 6'×4 mm I.D., glass, 10% SE-30 on Chromosorb W (AW-DMCS) H.P.
Oven Temperature: 250° C.
Injection Port Temperature: 270° C.
Detector Temperature: 270° C.
Carrier Gas: $N_2$, 45 ml/min.
Range: $10^3$
Recorder Presentation: 100 mv full scale
Injection Volume: 2.0 μl Mixtures containing different concentrations of 1-(2',6'-dimethylphenyl)-3-methylamidinourea hydrochloride in DMF-DMA, and internal standard when injected into G.C., show the peak area ratio to be linear when plotted against the concentration of 1-(2',6'-dimethylphenyl)-3-methylamidinourea hydrochloride. Similar results are obtained when the method is used for the analysis of 1-(2',6'-diethylphenyl)-3-methylamidinourea hydrochloride and 1-(2',6'-dimethylphenyl)-3-(N,N-dimethyl)-amidinourea. The G.C. method thus developed shows validity of the assay of 1-(2',6'-dimethylphenyl)-3-methylamidinourea hydrochloride and related compounds.

EXAMPLE 3

Isolation and Confirmation of DMF-DMA Derivative of 1-(2',6'-dimethylphenyl)-3-methylamidinourea Derivatization of 1-(2',6'-dimethylphenyl)-3-methylamidinourea is carried out according to the procedure outlined in Example 2 above. The DMF-DMA derivative of 1-(2',6'-dimethylphenyl)-3-methylamidinourea is extracted into chloroform leaving the by-product, tetramethylammonium chloride in aqueous layer. The chloroform solution is evaporated to dryness and the resulting product is recrystallized in 2-pentanone.

The pure form of the derivative is subjected to I.R., N.M.R., mass spectrometric and elemental analyses to confirm the structure of the derivative.

I.R. Analysis-The I.R. spectrum of the crystallized material from chloroform shows a singlet at 3300 cm$^{-1}$ representing —NH stretch of secondary amine, a doublet at 1700 cm$^{-1}$, indicating the presence of —C=N stretches and a strong bond at 1620 cm$^{-1}$ confirming carbonyl function from an amide group. However, the spectrum of the material crystallized from 2-pentanone is slightly different which indicates different polymorphic forms of the derivative.

N.M.R. Analysis—The N.M.R. spectrum shows six protons of the two methyl groups on the aromatic ring at 2.20 p.p.m. (singlet), three protons of the methyl group (NHCH$_3$) at 3.10 p.p.m. (doublet), three protons of the aromatic ring at 7.26 p.p.m. (singlet) and one proton (N—CH=N) at 7.75 p.p.m. (singlet). The doublet at 3.10 p.p.m. becomes singlet on deuteration.

Mass Spectrometric Analysis—The chemical ionization mass spectrum of this derivative, (GC/MS Finnigan Instrument) is carried out with methane as a reagent gas. The intense protonated molecular ion (m/e) 231 in the spectrum confirms the molecular weight of the derivative as 230.

Based on the above spectral data, the structure of the DMF-DMA derivative of 1-(2',6'-dimethylphenyl)-3-methylamidinourea is assigned as a 1,2-dihydro-1,3,5-triazine-2-one.

EXAMPLE 4

Preparation of 1-(2',6'-dimethylphenyl)-4-methylamino-1,2-dihydro-1,3,5-triazin-2-one About 200 mg. of 1-(2',6'-dimethylphenyl)-3-methylamidinourea is introduced into a gas chromatograph hypo vial and dissolved in 1 ml. of acetonitrile. To the solution is added 0.2 ml. of DMF DMA reagent. The vial is sealed with crimper and heated at 105° C. for 15 minutes in an oven. Seven vials are made. The contents of the vials are then put into a long-neck round bottom flask and evaporated to dryness by a flask evaporator. The solid mass is dissolved in a mixture of 30 ml. of CH Cl$_3$ and 20 ml. of water and shaken vigorously in a 60 ml. separatory funnel. The aqueous layer is discarded and 20 ml. of water is added and shaken. The CH Cl$_3$ layer is then taken off and about 10 g. of anhydrous Na$_2$SO$_4$ is added, the CH Cl$_3$ solution is decanted into a flask and evaporated to dryness. The solid material is dissolved in pentanone-2 (about 80 ml.) at 70° C. The solution is concentrated and crystallizes upon cooling. The crystals are collected and dried in a desiccator with P$_2$O$_5$ with vacuum for one hour.

| Elemental Analysis | MW:230.26 | MP:225-226° C. | |
|---|---|---|---|
| | C | H | N |
| Calculated | 62.59 | 6.13 | 24.33 |
| Found | 62.84 | 6.15 | 24.28 |

EXAMPLE 5

Preparation of 1-(2',6'-diethylphenyl)-4-methylamino-1,2-dihydro-1,3,5-triazin-one The same procedure is followed as in Example 4 above using 1-(2',6'-diethylphenyl)-3-methylamidinourea as the starting material and using as the recrystallization medium a mixed solvent of pentanone and hexane (30:10).

| Elemental Analysis | MP: 210-211° C. | | |
|---|---|---|---|
| | C | H | N |
| Calculated | 65.09 | 7.02 | 21.89 |
| Found | 65.34 | 7.01 | 21.83 |

EXAMPLE 6

1-(2',6'-dimethylphenyl)-4-methylamino-1,2-dihydro-1,3,5-triazin-2-one hydrochloride To a suspension of 10.0 g. (39.0 m. mol) of 1-(2',6'-dimethylphenyl)-3-methylamidinourea hydrochloride in acrylonitrile (CH$_3$CN) (50 ml.) is added 9.3 g. (78.0 m mol) of dimethylformamide dimethylacetal (DMF-DMA) and the resulting solution, in a bomb, is heated to 100°–105° C. for one hour. After cooling the reaction mixture is placed in a round bottom flask and concentrated under reduced pressure. The residue is partitioned between H$_2$O and CHCl$_3$ and the layers separated. The aqueous layer is extracted with CHCl$_3$ (1×50 ml). The combined CHCl$_3$ extracts are washed with H$_2$O (1×50 ml) dried (MgSO$_4$) and concentrated under reduced pressure. A small amount of the residue is triturated in hexane to give a white solid, having melting point 224. NMR and IR show the product to be identical with that of Example 3. The remainder of the residue is dissolved in MeOH and acidified with HCl/MeOH. The MeOH is removed under vacuum and the residue crystallized from CH$_3$CN to give 6.8 g. (65%) of 1-(2',6'-dimethylphenyl)-4-methylamino-1,2-dihydro-1,3,5-triazin-2-one hydrochloride, melting point 234°–8° C. (decomposition).

| Analysis calculated for: C$_{12}$H$_{15}$ClN$_4$O | | | |
|---|---|---|---|
| | C | H | N | Cl |
| Calculated | 54.04 | 5.67 | 21.01 | 13.29 |
| Found | 54.14 | 5.80 | 21.90 | 13.28 |

EXAMPLE 7

1-(2',6'-dimethylphenyl)-4-methylamino-1,2-dihydro-1,3,5-triazin-2-one 1-(2',6'-dimethylphenyl)-3-methylamidinourea hydrochloride is suspended in 500 ml. of acrylonitrile in a 1 liter round bottom flask. 95 grams of DMF-DMA is added. The mixture is heated to reflux with magnetic stirring for 2 hours then cooled to room temperature. The mixture is concentrated to dryness and the residue precipitated from $CH_2Cl_2$ and $H_2O$. The aqueous portion is extracted with 200 ml. of $CH_2Cl_2$ and the combined organic layers are washed with $CH_2Cl_2$ ($2 \times 300$ ml) then with a saturated NaCl solution and dried over anhydrous $MgSO_4$ and weighed. The mixture is filtered to give a white solid which is crystallized from absolute ethanol and recrystallized from $CH_2Cl_2$. There is obtained a white solid which is dried under vacuum at 80° C. for 4 hours, to give 67.6 grams of white solid having a melting point of 224°-5° C.; NMR confirmed; TLC (3% $NH_4OH$/iPA) one spot at $R_f$ 0.575 no other point spots; elemental analysis for $C_{12}H_{14}N_4O$ molecular weight 230.272.

|  | C | H | N |
|---|---|---|---|
| Calculated | 62.59 | 6.13 | 24.34 |
| Found | 62.46 | 6.32 | 24.34 |

The 67.6 grams (0.394 m.) of the product obtained is dissolved in 1 liter of iPA 22.8 ml. (0.353 mole) of methane sulfonic acid is added to the solution with magnetic stirring. After 25 minutes crystals form. The solution is cooled to room temperature and filtered. The solid is washed with iPA and ethanol and dried under vacuum overnight to give the methane sulfonic acid salt of 1-(2',6'-dimethylphenyl)-4-methylamino-1,2-dihydro-1,3,5-triazin-2-one.

EXAMPLE 8

1-(2',6'-dimethylphenyl)-4-methylamino-1,2-dihydro-1,3,5-triazin-2-one methanesulfonate; Alternative Preparation of Methane Sulfonic Acid Salt A solution of 6.0 g. (0.026 moles) of 1-(2',6'-dimethylphenyl)-4-methylamino-1,2-dihydro-1,3,5-triazine-2-one in 100 ml. iPA is prepared with warming. To the warm solution is added 2.0 ml. (0.031 moles) of methane-sulfonic acid. The mixture becomes hot and crystals of white crystalline solid begin to form almost immediately. The mixture is allowed to cool to room temperature in tap water and filtered. The solution is washed with iPA/EtOH and dried overnight at 50°-60° C. in a vacuum to give 8.0 g. of 1-(2',6'-dimethylphenyl)-4-methylamino-1,2-dihydro-1,3,5-triazin-2-one methanesulfonate.

| Calculated for: $C_{13}H_{18}N_4O_4S$ | | MW: 326.35 | MP: 262-65° C. dec. | |
|---|---|---|---|---|
|  | C | H | N | S |
| Calculated | 47.84 | 5.57 | 17.17 | 9.80 |
| Found | 48.03 | 5.71 | 17.25 | 10.27 |

EXAMPLE 9

1-(2',6'-diethylphenyl)-4-methylamino-1,2-dihydro-1,3,5-triazin-2-one hydrochloride To a suspension of 22.8 g. (80.0 mmol) of 1-(2',6'-diethylphenyl)-3-methylamidinourea hydrochloride in $CH_3CN$ (100 ml.) are added 19.1 g. (160.0 mmol) of DMF-DMA and the reaction mixture is heated at reflux for 3 hours. The $CH_3CN$ is removed under reduced pressure and the residue partitioned between $CHCl_3$ and $H_2O$. The layers are separated and the aqueous layer extracted with $CHCl_3$ ($1 \times 100$). The combined $CHCl_3$ extracts are washed with $H_2O$ ($1 \times 100$ ml.), dried ($MgSO_4$) and concentrated under reduced pressure to give an off-white solid, which by NMR confirms the desired free base. The solution is dissolved in $H_2OH$ and acidified with HCl/MeOH and the MeOH removed under reduced pressure to give an off-white solid which is crystallized from $CH_3CN$ to give after vacuum drying over the weekend (105° C., house vacuum) 16.7 g. (71%) of crude product. The material is recrystallized from $CH_3CN$ (a hot filtration is necessary to remove some undissolved solid) to give 11.0 g. (47%) of desired product as a white crystalline solid.

| Analysis calculated for: $C_{14}H_{18}N_4OHCl$ | | MP: 208–15° C. | |
|---|---|---|---|
|  | C | H | N | Cl |
| Calculated | 57.04 | 5.50 | 19.01 | 12.03 |
| Found | 57.14 | 5.51 | 19.38 | 12.01 |

EXAMPLE 10

1-(2',6'-dimethylphenyl)-6-methyl-4-methylamino-1,2-dihydro-1,3,5-triazin-2-one

To a suspension of 10.3 g. (40.0 mmol) of 1-(2',6'-dimethylphenyl)-3-methylamidinourea hydrochloride in $CH_3CN$ (50.0 mmol) is added 10.7 g. (80.0 mmol) of N,N-dimethylacetamide dimethylacetal and the resulting mixture heated at reflux for 2½ hours. The solvent is removed under vacuum to give a semisolid residue which is diluted with $H_2O$ and the precipitated solid filtered and washed well with $H_2O$ then air dried. NMR taken on the crude wet solid shows that the desired product is formed. The solid is recrystallized from $CH_3CN$ to give 7.8 g. (80%) of product as a white crystalline solid.

| Analysis calculated for: $C_{13}H_{16}N_4$ | | MP: 251.5° C. to 252.5° C. | |
|---|---|---|---|
|  | C | H | N |
| Calculated | 63.91 | 6.60 | 22.93 |
| Found | 63.52 | 6.33 | 23.01 |

EXAMPLE 11

4-dimethylamino-1-(2',6'-dimethylphenyl)-1,2-dihydro-1,3,5-triazin-2-one hydrochloride To a suspension of 19.0 g. (0.07 mole) of 1-(2',6'-dimethylphenyl)-3-(N,N-dimethyl)-amidinourea in acrylonitrile (100 m.) is added 16.7 g. (0.14 mole) of DMF-DMA and the mixture refluxed for 2 hours. The acrylonitrile is removed under reduced pressure and the residue partitioned between $H_2O$ and $CHCl_3$. The layers are separated and the aqueous layer extracted with $CHCl_3$ ($1 \times 100$ ml.). The $CHCl_3$ extracts are washed $H_2O$ ($1 \times 50$ ml.), dried over $MgSO_4$ and concentrated at reduced pressure to give an oil. Trituration of the oil in EtOH precipitates a white solid which is filtered and washed with EtOH to give the desired product after air drying. The solid is dissolved in MeOH and acidified with HCl/MeOH. The MeOH is removed under reduced pressure to give a white solid which is triturated with $CH_3CN$, filtered and washed with $CH_3CN$ to give 7.5 g. (38%) of product which by NMR seems to be a hydrate or wet. The solid is vacuum dried for 6 hours at 100° C. under vacuum.

| Analysis calculated for: $C_{13}H_{10}N_4O\cdot HCl$ | | | |
|---|---|---|---|
| | C | H | N | Cl |
| Calculated | 55.61 | 6.10 | 19.96 | 12.63 |
| Found | 55.81 | 5.96 | 20.31 | 12.46 |

EXAMPLE 12

1-(2-chloro-6-methylphenyl)-4-methylaminodihydro-1,3,5-triazin-2-one

To a suspension of 11.1 g (40 mmol) of 1-(2-chloro-6-methylphenyl)-3-methyl amidinourea hydrochloride in 45 ml of CH$_3$CN was added 5.7 g (48 mmol) of dimethylformamide dimethylacetal which was washed into the flask with an additional 5 ml of CH$_3$CN.

The reaction mixture was stirred for 1.5 hours after which an aliquot of the reaction product which had been dissolved in MeOH showed there to be one major spot with R$_f$ equal to that of 1-(2-chloro-6-methylphenyl)-4-methylaminodihydro-1,3,5-triazin-2-one and two minor spots of very small R$_f$, one at the origin and one of the same R$_f$ as the starting material amidinourea hydrochloride. The reaction mixture was allowed to stir an additional 0.5 hour and the solid was filtered to yield 1-(2-chloro-6-methylphenyl)-4-methylaminodihydro-1,3,5-triazin-2-one, (EtOAc:MeOH; 9:1). It has the same two impurities as the crude reaction mixture. 7.7 g of the crude mixture was recrystallized from absolute EtOH; melting point 257.5°–258.5° C.

Most of the 1-(2-chloro-6-methylphenyl)-4-methylaminodihydro-1,3,5-triazin-2-one (5.0 g, 65%) was insoluble in hot absolute EtOH. The residue was filtered off to yield product having melting point 254°–255.5° C. The product was placed in the vaccum dissicator at 100° C. for 3 hours to yield 1-(2-chloro-6-methylphenyl)-4-methylaminodihydro-1,3,5-triazin-2-one, melting point 255.5°–257.5° C.; NMR still showed about 2% CH$_3$CN impurity. 1-(2-chloro-6-methylphenyl)-4-methylaminodihydro-1,3,5-triazin-2-one was returned to the dissicator at 100° C. for overnight. 4.40 g. of the product was dissolved in hot MeOH (100 ml.) and EtOAc was added and the solution was concentrated on a hot plate until the solution became cloudy. The solution was allowed to cool to ambient temperature and then was placed in the refrigerator. The solid was filtered to yield 0.99 g., melting point 257.5°–258.5° C.

The filtrate produces a second crop of crystals after sitting overnight. This is filtered to yield an additional 1.41 g. of product with melting point 258° C.

The crystal products are combined and submitted for analysis as 1-(2'-chloro-6'-methylphenyl)-4-methylamino-1,2-dihydro-1,3,5-triazin-2-one.

| Analysis calculated for: $C_{11}H_{11}ClN_4O$ | | | |
|---|---|---|---|
| | C | H | N | Cl |
| Calculated | 52.70% | 4.42% | 22.35% | 14.14% |
| Found | 52.61% | 4.48% | 22.69% | 13.89% |

IR Analysis (Nujol: 1695, 1655, 1640, 1585, 148, 1465, 1415, 1400, 1375, 1305, 1265, 1245, 1225, 1180, 875, 835, 790, 730 and 665 cm.$^{-1}$

EXAMPLE 13

To a magnetically stirred suspension of 9.7 g. (40 mmol) of 1-(2',6'-dimethylphenyl)amidinourea hydrochloride in 50 ml. of CH$_3$CN at room temperature is added 5.7 g. (48 mmol) of N,N-dimethylformamide dimethylacetal. The reaction mixture is stirred for 10 minutes after which all of the solid material goes into solution. The solution is stirred for 5 minutes after which a seed crystal is added. A white solid precipitates. The reaction mixture is stirred for an additional 1.5 hours, after which the solid precipitate is filtered to yield 1-(2',6'-dimethylphenyl)-4-amino-1,2-dihydro-1,3,5-triazin-2-one, melting point 248.5°–249.5° C. When recrystallized from absolute EtOH the product is obtained as a white solid with melting point 258.6°–259° C.

| Elemental analysis calculated for: $C_{11}H_{12}N_4O$ | | |
|---|---|---|
| | C | H | N |
| Calculated | 61.10% | 6.59% | 25.91% |
| Found | 60.75% | 5.76% | 25.90% |

EXAMPLE 14

To a magnetically stirred suspension of 12.06 g. (38 mmol) of 1-N-butoxy-3-(2',6'-dimethylphenyl)amidinourea hydrochloride in 25 ml. of CH$_3$CN is added 9.11 g. (76 mmol) of N,N-dimethylformamide dimethyl acetal and another 25 ml. of CH$_3$CN. All of the solid dissolves after the reaction is stirred for 5 minutes. The reaction solution is refluxed for 2 hours and allowed to come to ambient temperature, then concentrated in vacuo to yield the desired product as a white solid. This is combined with 200 ml. of H$_2$O to an insoluble, thin gummy solid which is transferred to a separatory funnel and extracted with CHCl$_3$ (3×75 ml). The organic layers are combined, washed with H$_2$O (2×75 ml) and saturated aqueous brine (1×75 ml). All aqueous washes are combined and back-extracted with (2×50 ml.), dried (Mg$_2$SO$_4$), filtered and concentrated in vacuo to yield 1-(2',6'-dimethylphenyl)-4-n-butoxyamino-1,2-dihydro-1,3,5-triazin-2-one, as a white solid containing some liquid. The product is triturated with iPA to yield a white solid: m.p. 144°–145° C.

| Elemental analysis calculated for: $C_{15}H_{20}N_4$ | | |
|---|---|---|
| | C | H | N |
| Calculated | 62.48% | 6.99% | 19.43% |
| Found: | 62.49% | 6.98% | 19.57% |

The filtrate is concentrated in vacuo to yield a yellow oil. This oil is triturated with about 20 ml. iPA and a white solid crystallizes out. The solid is filtered and washed with cold iPA to yield product with melting point 144°–145.5° C. which appears to be identical to the product obtained above.

EXAMPLE 15

To a magnetically stirred suspension of 15.6 g. (49.5 mmol) of 1-(2',6'-dimethylphenyl)-3-sec-butoxyamidinourea hydrochloride in 25 ml. of CH$_3$CN is added 11.8 g. (99 mmol) of N,N-dimethylformamide dimethylacetal and another 25 ml. of CH$_3$CN. The solid dissolves at this point. The reaction solution is heated to reflux. After 2 hours the reaction solution is removed from the heat and allowed to cool to ambient temperature transferred to a larger flask and concentrated in vacuo.

The white solid residue is taken up in CHCl$_3$ and washed with H$_2$O (3×50 ml). All aqueous layers are combined and back-extracted with CHCl₃ (2×50 ml). All organic layers are combined and washed with saturated aqueous brine (1×50 ml). The organic layer is separated, dried (MgSO₄), filtered and concentrated in vacuo to yield only white solid (20.2 g.); impurities from, and possible starting material are present. A small amount of product is dissolved in boiling Et₂O, diluted with hexane and concentrated until solid begins to form. The solid which crystallizes out is 1-(2',6'-dimethylphenyl)-4-sec-butoxyamino-1,2-dihydro-1,3,5-triazin-2-one.

The entire amount of product is dissolved in boiling Et₂O, filtered, concentrated in a steam bath, and diluted with hexane until a white solid crystallizes out. The solution is cooled to ambient temperature.

The product is filtered and washed with hexane to yield product with melting point 149° C.

| Analysis calculated for: C₁₅H₂₀N₄O₂ | | | |
|---|---|---|---|
| | C | H | N |
| Calculated | 62.48% | 6.99% | 19.43% |
| Found | 62.41% | 7.01% | 19.27% |

EXAMPLE 16

4-Methylamino-1-phenyl-1,2-dihydro-1,3,5-triazin-2-one hydrochloride

To a suspension of 9.5 g. (40.0 mmol) of 1-phenyl-3-methylamidinourea hydrochloride hemihydrate in CH₃CN (50 ml.) is added 9.5 g. (80.0) of DMF-DMA and the mixture heated to 105°–110° C. in a closed bomb for 2 hours. The reaction mixture is allowed to cool. A solid precipitates. This is filtered and washed with CH₃Cl. The filtrate is concentrated and the residue diluted with H₂O. The precipitated solid is filtered, washed with H₂O and Et₂O. The two fractions are combined and crystallized from CH₃CN. 4.5 g. (56%) of white solid, which by NMR seems to be the hemihydrate, melting point 223°–4' C. is obtained.

| Analysis calculated for: C₁₀H₁₀N₄O | | | |
|---|---|---|---|
| | C | H | N |
| Calculated | 59.40 | 4.98 | 27.71 |
| Found | 59.27 | 4.71 | 28.71 |

The solid is dissolved (warmed on steam bath) in MeOH and acidified with HCl/MeOH. The MeOH is removed under reduced pressure to give a white solid 4-methylamino-1-phenyl-1,2-dihydro-1,3,5-triazin-2-one hydrochloride which is crystallized from CH₃OH/CH₃CN.

EXAMPLE 17

1-(2'-methylphenyl)-4-ethylamino-1,2-dihydro-1,3,5-triazin-2-one

To a magnetically stirred suspension of 9.02 g. (35.2 mmol) of 1-(2'-methylphenyl)-3-ethylamidinourea hydrochloride in 30 ml. of CH₃CN is added 8.40 g. (70.5 mmol) of N,N-dimethylformamide dimethylacetal and 20 ml. of CH₃CN. All of the solid dissolves. The reaction mixture is refluxed for 2 hours, allowed to come to ambient temperature and partitioned between CHCl₃ and H₂O.

The layers are separated and the aqueous layer is extracted with CHCl₃ (1×50 ml). The organic layers are combined, washed with H₂O (1×50 ml) and saturated brine (1×50 ml). These last two aqueous layers are combined and back-extracted with (1×50 ml.). All organic layers are combined, dried (MgSO₄), filtered and concentrated in vacuo to yield 1-(2'-methylphenyl)-4-ethylamino-1,2-dihydro-1,3,5-triazin-2-one as a white solid, 8.6 g. (110%). After recrystallizing from EtOAc the product is filtered and dried on the Bückner funnel under vacuum to give the desired end product with melting point 208.5°–209.5° C.

| Analysis calculated for: C₁₂H₁₄N₄O | | | |
|---|---|---|---|
| | C | H | N |
| Calculated | 62.59% | 6.13% | 24.33% |
| Found | 62.39% | 5.96% | 24.64% |

EXAMPLE 18

1-(2',6'-dichlorophenyl)-4-methylamino-1,2-dihydro-1,3,5-triazin-2-one

To a magnetically stirred suspension of 11.88 g. (40 mmol) of 1-(2',6'-dichlorophenyl)-3-methylamidinourea hydrochloride in 30 ml. of CH₃CN is added 9.52 g. (80 mmol) of N,N-dimethylformamide dimethylacetal in 20 ml. of CH₃CN. The solid material begins to dissolve immediately but in a few minutes, before the starting material amidinourea has dissolved, another fine particle white solid begins to precipitate out. The reaction mixture is stirred at ambient temperature for 1 hour then heated to reflux for 2 hours. After 2 hours the reaction mixture is allowed to come to ambient temperature and the white solid precipitate filtered out to yield the desired product, melting point 270° C.; TLC (EtoAc 9:1); one major spot, one minor spot at origin. A small sample recrystallized from CH₃OH/EtoAc gave 1 spot on TLC. (9.6 g. 89%). The product is recrystallized from MeOH to yield 1-(2',6'-dichlorophenyl)-4-methylamino-1,2-dihydro-1,3,5-triazin-2-one.

The recrystallizing solution is concentrated from 1400 ml. to 700 ml., then refrigerated after a lot of solid comes out. After refrigeration for several hours, the solid is filtered and washed with cold MeOH to yield additional product having melting point 270° C. TLC (EtOAc/MeOH; 9:1) still shows a very small spot at origin.

| Analysis calculated for: C₁₀H₈N₄Cl₂O | | | | |
|---|---|---|---|---|
| | C | H | N | Cl |
| Calculated | 44.30% | 2.97% | 20.67% | 26.16% |
| Found | 44.24% | 2.73% | 20.80% | 26.09% |

EXAMPLE 19

1-(2'-methylphenyl)-4-methylamino-1,2-dihydro-1,3,5-triazin-2-one

To a magnetically stirred suspension of 9.72 g. (40 mmol) of 1-(2'-methylphenyl)-3-methylamidinourea hydrochloride in 30 ml. of CH₃CN is added 9.52 g. (80 ml.) of N,N-dimethylformamide dimethylacetal. After the mixture is further diluted with 25 ml. CH₃CN and stirred for 5 minutes all of the solid is dissolved. TLC (3% NH₄OH) shows a new spot; about equal in size to a spot in starting material; (EtoAc/MeOH; 9:1) shows mostly a new spot. The solution is refluxed for 2 hours. The reaction mixture is allowed to cool to ambient temperature. The reaction mixture is then poured into $CHCl_3/H_2O$ and separated. The aqueous layer is extracted with $CHCl_3$ (for a total of 3×50 ml.). The organic layers are combined and washed with $H_2O$ (2×50 ml.). The aqueous layers are combined and back extracted with $CHCl_3$ (1×50 ml.). All organic layers are combined, dried, filtered and concentrated in vacuo to yield the product which is recrystallized from absolute EtOH, filtered and washed with cold absolute EtOH and air-dried. The product is 1-(2'-methylphenyl)-4-methylamino-1,2-dihydro-1,3,5-triazin-2-one, melting point 191.5°–192.5° C.

| Analysis calculated for: $C_{11}H_{12}N_4O$ | | | |
|---|---|---|---|
| | C | H | N |
| Calculated | 61.10% | 5.59% | 25.91% |
| Found | 61.02% | 5.80% | 26.25% |

EXAMPLE 20

1-(2',6'-dimethylphenyl)-4-(2,2,2-trifluoroethylamino)-1,2-dihydro-1,3,5-triazin-2-one To a suspension of 130 g. (40.0 mmol) of 1-(2',6'-dimethylphenylcarbamoyl-3-(2,2,2-trifluoroethyl) guanidine hydrochloride in $CH_3CN$ (50 ml.) is added 95 g. (80.0 mmol) of DMF-DMA and the mixture heated at reflux for 2 hours. The solvent is removed under vacuum and the residue partitioned between $CHCl_3$ and $H_2O$. The layers are separated and the aqueous layer is extracted with $CHCl_3$ (1×100 ml.). The extracts are dried ($MgSO_4$) and concentrated to give a white solid which is crystallized from absolute EtOH to give after heating under vacuum at 100° C. for 1 hour; 9.5 g. (80%) of 1-(2',6'-dimethylphenyl)-4-(2,2,2-trifluoroethylamino)-1,2-dihydro-1,3,5-triazin-2-one; melting point 212.3° C.

| Analysis calculated for: $C_{13}H_{13}F_3N_4O$ | | | | |
|---|---|---|---|---|
| | C | H | N | F |
| Calculated | 52.35 | 4.39 | 18.78 | 19.11 |
| Found | 52.45 | 4.31 | 19.67 | 18.84 |

EXAMPLE 21

1-(2-pyridyl)-4-methylamino-1,2-dihydro-1,3,5-triazin-2-one

A 14.0 g. (72.5 mmol) of 1-(2-pyridyl)-3-methylamidinourea is placed in 100 ml. of MeOH and heated slightly. The solid does not dissolve. A 50 ml. portion of an HCl/MeOH solution is added such that the solution becomes acid. Most of the solid dissolves. An additional 100 ml. of MeOH is added; some more solid dissolves but not all, even upon heating. An additional 50 ml. of MeOH is added. All of the solid dissolves. This solution is concentrated to ½ volume (150 ml.) on a hot plate and $CH_3CN$ is added to it, with additional concentration until the hot solution becomes cloudy. The solution is allowed to cool to ambient temperature.

The solid is filtered to yield the product with melting point 153.5°–157° C. which after air-drying for 3 hours has melting point 156°–159° C. and after drying in a vacuum desiccator has melting point 155.5°–158° C.

To a magnetically stirred suspension of 14.50 g. (54.5 mmol) of 1-(2-pyridyl)-3-methylamidinourea dihydrochloride in 50 ml. of $CH_3CN$ there is added 15 ml. (13.46 g. 113 mmol) of N,N-dimethylformamide dimethylacetal. Some of the solid appears to dissolve but reprecipitation occurs within seconds. The reaction mixture is warmed. A TLC (iPA:NH4 3:1) shows no starting material present after 5 minutes.

The reaction mixture is stirred for 2 hours and filtered to yield product of melting point 117.5°–190° C.; 8.5 g. (77%); TLC (iPA-NH4OH); shows a minor spot with same $R_f$ as starting material and a major spot with $R_f$ about twice as large.

The product is dissolved (mostly) in hot MeOH, hot filtered and concentrated in a hot plate to 350 ml. and allowed to come to ambient temperature overnight.

The next morning a precipitate of white crystals has formed. The solution is cooled in the refrigerator. This cooled solution is filtered and washed with MeOH to yield product with melting point 240.5°–242° C.; TLC (iPA:NH4OH); (Et2O), (EtOAc:MeOH; 9:1): shows only one spot in all solvent systems.

| Elemental analysis calculated for: $C_9H_9N_5$ | | | |
|---|---|---|---|
| | C | H | N |
| Calculated | 53.20% | 4.46% | 34.46% |
| Found | 53.11% | 4.46% | 35.42% |

EXAMPLE 22

1-(2'-bromo-6'-methylphenyl)-4-methylamino-1,2-dihydro-1,3,5-triazin-2-one

To a suspension of 5.5 g. (0.017 moles) of 1-(2'-bromo-6'-methylphenyl)-3-methyl-amidinourea in 60 ml. of $CH_3CN$ there is added 5.3 ml. (about 0.07 moles) of dimethyl formamide-dimethyl acetal. Solid begins to dissolve and a new solid precipitates. The mixture is heated to reflux and kept there for 2 hours. The solution remains clear on cooling to room temperature. The $CH_3CN$ is removed in vacuo and the resulting thick oil stirred in 80 ml. of $H_2O$. The resulting solid is removed by filtration and washed with $H_2O$ (about 100 ml.).

The solid after air drying is recrystallized from THF (200 ml.) heated and boiled down to about 50 ml. After cooling, filtration, and washing with hexane there is obtained 3.0 g. of 1-(2'-bromo-6'-methylphenyl)-4-methylamino-1,2-dihydro-1,3,5-triazin-2-one melting point 238°–40° C. Analysis indicates very pure material but a second crop of off-white crystals about 2.0 g. is not as pure. The materials are combined and dissolved in hot iPA, filtered and 1.5 ml. (about 0.023 moles) of $CH_3SO_3H$ is added. The mixture is cooled. The resultant solid is removed by filtration and washed with EtOAc. The solid is recrystallized from $CH_3OH$/EtOAc to give 5.20 g. of crystalline product, melting point 243°–6° C. (with decomposition).

| Calculated for: $C_{12}H_{15}BrN_4O_4A$ MW: 391.23 | | | | | |
|---|---|---|---|---|---|
| | C | H | N | Br | S |
| Calculated | 36.84 | 3.87 | 14.32 | 20.43 | 8.18 |
| Found | 37.00 | 3.96 | 14.30 | 20.49 | 8.4 |

EXAMPLE 23

1-(2',6'-dimethylphenyl)-4-[(2-pyridyl)methylamino]-1,2-dihydro-1,3,5-triazin-2-one To a suspension of 10.2 g. (28.0 mmol) of 1-(2',6'-dimethylphenyl)-3-[(2-pyridyl)methyl]amidinourea in CH₃CN (100 ml) is added 10.0 g. (84.0 mmol) of DMF-DMA and the reaction mixture heated at reflux for two hours. The solvent is removed under vacuum and the residue diluted with H₂O and made basic with 10% aqueous NaOH (pH10). The aqueous layer is extracted with CHCl₃ (2×100 ml.) and the extracts dried (MgSO₄) and concentrated under vacuum to an orange oil, which by NMR looks to be a mixture of starting material and product. The oil is layered out with H₂O and Et₂O. The oil solidifies. This solid is filtered and washed with H₂O and Et₂O and air dried. The solid is then crystallized (2×) from EtOAc to give 3.2 g. (37%) of a tan crystalline solid, melting point 165°–6° C.

| Analysis calculated for: C₁₇H₁₇N₅O | | | |
|---|---|---|---|
| | C | H | N |
| Calculated | 66.43 | 5.58 | 22.79 |
| Found | 66.51 | 5.36 | 22.89 |

EXAMPLE 24

1-(2',6'-dimethylphenyl)-4-methoxyamino-1,2-dihydro-1,3,5-triazin-2-one hydrate

To a suspension of 10.9 g. (40.0 mmol) of 1-(2',6'-dimethylphenyl)-3-methoxyamidinourea in CH₃CN (50 ml.) is added 9.5 g. (80.0 mmol) of DMF-DMA and the mixture heated at 105°–110° C. in a closed bomb for 1½ hours. The reaction mixture is cooled and poured into a round bottom flask and the CH₃CN removed under reduced pressure. The residue is partitioned between CHCl₃ and H₂O and the layer separated. The aqueous layer is extracted with CHCl₃ (1×75 ml.). The combined organic layers are washed with H₂O (1×50 ml.), dried (MgSO₄) and concentrated under reduced pressure to give an oily residue. The residue is taken up in Et₂O and washed with H₂O (2×50 ml.). The Et₂O layer is dried (MgSO₄) and concentrated under reduced pressure to give a viscous oil. NMR shows that DMF has been removed. The oil is taken up in hot CH₃CN cooled and a small amount of CHCl₃, H₂O and DMSO insoluble material filtered off. The filtrate is concentrated to give a viscous oil. TLC of the oil (Silicagel; 3% NH₄OH, iPA) versus starting material shows one spot moves slower than starting material. Upon addition of MeOH and warming on a steam bath the oil solidifies. The solid is crystallized from MeOH to give 4.6 g. (43%) of 1-(2',6'-dimethylphenyl)-4-methoxyamino-1,2-dihydro-1,3,5-triazin-2-one as a white solid, melting point 78°–80° C.

| Analysis calculated for: C₁₂H₁₄N₄O₂ | | | |
|---|---|---|---|
| | C | H | N |
| Calculated | 58.53 | 5.73 | 22.75 |
| Found | 55.04 | 6.20 | 21.48 |

The NMR shows a broad peak at 3.58 which is integrated for two protons. This peak disappeared on adding D₂O. The analysis recalculated for the presumed hydrate is as follows:

| Analysis calculated for: C₁₂H₁₆N₄O | | | |
|---|---|---|---|
| | C | H | N |
| Calculated | 54.54 | 6.10 | 21.20 |

-continued

| Analysis calculated for: C₁₂H₁₆N₄O | | | |
|---|---|---|---|
| | C | H | N |
| Found | 55.04 | 6.20 | 21.48 |

Analysis indicates compound is obtained as the hydrate.

EXAMPLE 25

1-(2',6'-Dimethylphenyl)-4-methylamino-1,2-dihydro-1,3,5-triazin-2-one methanesulfonate To 29.2 grams (0.4 mole) of N,N-dimethylformamide, heated to 50°–60° C., are added dropwise 50.5 grams (0.4 mole) of dimethyl sulfate while maintaining the temperature between 50° and 60° C. After the addition, the reaction mixture is heated at 70°–80° C. for four hours. The reaction mixture is diluted with acetonitrile (150 milliliters) and cooled to approximately 10° C. in an ice water bath. Then 44.0 grams (0.2 mole) of 1-(2',6'-dimethylphenyl)-3-methylamidinourea are added on one portion followed by the dropwise addition of 80.8 grams (0.8 mole) of triethylamine while keeping the temperature below 25° C. The reaction mixture is allowed to come to ambient temperature and stirred for one hour. The solvent is removed in vacuo and the residue diluted with water and the pH adjusted to 10 with ten percent (10%) aqueous sodium hydroxide. The aqueous layer is extracted with chloroform (3 times with 200 milliliters each time) and the combined extracts dried (MgSO₄) and concentrated in vacuo. The residual solid is taken up in boiling acetonitrile (350 milliliters) and concentrated to approximately two-thirds of its volume on a steam bath. The hot solution is treated with 21.0 grams (0.22 mole) of methanesulfonic acid and on cooling a white crystalline solid deposits, which is filtered, washed with cold acetonitrile and vacuum dried at 80° C. for one hour to yield 60.6 grams (93%) of 1-(2',6'-dimethylphenyl)-4-methylamino-1,2-dihydro-1,3,5-triazin-2-one methanesulfonate, m.p. 264°–266° C. dec.

EXAMPLE 26

1-(2',6'-Diethylphenyl)-4-amino-1,2-dihydro-1,3,5-triazin-2-one

To a magnetically stirred suspension of 23.4 g (0.10 mol.) of 1-(2',6'-diethylphenyl) amidinourea in 100 ml of CH₃CN is added 23 g (0.20 mol.) of N,N-dimethylformamide dimethylacetal. The reaction is stirred at ambient temperature and monitored by Tlc. After two hours the solid has all dissolved.

After 2.5 hours the reaction mixture is concentrated in vacuo to yield a greenish oil. The oil is taken up in CHCl₃ and let stand overnight, then washed with H₂O (3×50 ml) and saturated aqueous brine (2×50 ml). All aqueous layers are combined and back-extracted with CHCl₃ (2×25 ml). All organic layers are combined, dired (Na₂SO₄), filtered and the filtrate concentrated in vacuo. The residue is triturated with hot EtOAc and filtered. The filtrate is combined with Et₂O and a solid precipitates out. The solid is filtered to yield (2',6'-diethylphenyl)-4-amino-1,2-dihydro-1,3,5-triazin-2-one calculated for C₁₃H₁₆N₄O.

Calculated: 63.92%C; 6.60%H; 22.93%N. Found: 63.88%C; 6.77%H; 22.78%N.

The product is recrystallized from EtOAc, refrigerated, filtered and washed with cold EtOAc, triturated with Et₂O and filtered to yield a white solid, which is recrystallized from EtOAc to give 1-(2',6'-diethylphenyl)-4-amino-1,2-dihydro-1,3,5-triazin-2-one; m.p. 136.5°-138.5° C.

EXAMPLE 27

1-(2',6'-diethylphenyl)-4-dimethylaminomethylene amino-1,2-dihydro-1,3,5-triazin-2-one 1-(2',6'-diethylphenyl)-4-amino-1,2-dihydro-1,3,5-triazin-2-one (5.9 g, 20 mmo) is combined with 30 ml of $CH_3CN$, none of the solid dissolves. To this is added 1.19 g (10 mmol) of N,N-dimethylformamide dimethylacetal. The solid dissolves within seconds. The reaction solution was stirred overnight.

After the reaction solution is stirred overnight, it darkens to a light brown color. Tlc does not appear to show any starting material still present. The reaction mixture is concentrated in vacuo to yield a light-brown solid which is taken up in $CHcl_3$, washed with $H_2O$ (3×35 ml) and saturated aqueous brine (2×50 ml). All aqueous washes are combined and back-extracted with $CHCl_3$ (2×50 ml). All organic layers are combined, dried ($Na_2SO_4$), filtered and filtrate concentrated in vacuo to yield an oil which looks like pure compound with no starting material. The oil solidifies and is recrystallized from EtoAc.

The solid is filtered and washed with cold EtOAc: m.p. 144°-146° C. calculated for $C_{16}H_{21}N_5O$.

Calculated: 64.19%C; 7.07%H; 23.29%N. Found: 64.11%C; 7.24%H; 23.59%N.

EXAMPLE 28

1-(2',6'-Diethylphenyl-4-methylamino-1,2-dihydro-1,3,5-triazin-2-one hydrochloride To a suspension of 22.8 g (80.0 mmol) of 1-(2',6'-diethylphenyl-4-methylamino-1,2-dihydro-1,3,5-one in $CH_3C \equiv N$ (100 ml) is added 1911 g (160.0 mmol) of DMF-DMA and the reaction mixture heated at reflux for 3 hours. The $CH_3C \equiv N$ is removed under reduced pressure and the residue partitioned between $CHCl_3$ and $H_2O$). The layers are separated and the aqueous layer extracted with $CHCl_2$ (1×100 ml). The combined $CHCl_3$ extracts are washed with $H_2O$ (1×100 ml), dried ($MgSo_4$) and concentrated under reduced pressure to give an off-white solid, which by NMR confirms the desired free base. The solid is dissolved in the OH and acidified with HCl/MeOH and the MeOH removed under reduced pressure to give an off-white solid which is crystallized from $CH_3C \equiv N$ to give after vacuum drying over the weekend, 16.7 grams of 1-(2',6'-diethylphenyl-4-methylamino-1,2-dihydro-1,3,5-triazin-2-one hydrochloride; m.p. 213-215.

EXAMPLE 29

1-(2',6'-diethylphenyl)-4-ethylamidino-1,2-dihydro-1,3,5-triazin-2-one

To a magnetically stirred stined suspension of 10/5 g (40 mmol) of 1-(2',6'-diethylphenyl)-3-ethylamidinourea in 10 ml of $CH_3CN$ is added 9.52 g (80 mmol) of N,N-dimethylformamide dimethylacetal and another 20 ml of $CH_3CN$. The reaction mixture is heated to reflux at which point all of the solid dissolves. The solution is refluxed for one hour, allowed to cool to ambient temperature and then concentrated in vacuo to yield an off-white solid which is taken up in $CHCl_3$, washed with $H_2O$) (2×50 ml) and saturated aqueous brine (2×25 ml). All aqueous wash layers are combined and back-extracted with $CHCl_3$, (2×25 ml). All organic layers are combined, dried ($Na_2SO_2$), filtered and the filtrate concentrated in vacuo to yield a yellow oil. The oil is taken up in MeOH and acidified with HCl/MeOH then concentrated in vacuo.

The off-white solid which resulted is recrystallized from EtoAc/MeOH to yield 1-(2,6-diethylphenyl)-4-ethylamino-1,2-dihydro-1,3,5-triazin-2-one hydrochloride; m.p. 200°-205° C. M.P. 200.5°-204.5° C. SOC-1103-76B analysis (calculated for $C_{15}H_{21}ClN_4O$).

Calculated: 58.34%C; 6.86%H; 18.14N; 11.48%Cl. Found: 56.44%C; 6.86%H; 17.72%N; 12.29%cl.

EXAMPLE 30

1-(2',6'-diethylphenyl)-4-n-propylamino-1,2-dihydro-1,3,5-triazin-2-one HCl

To a magnetically stirred suspension of 11.04 g (40 mmol) of 1-(2',6'-ethylphenyl)-3-n-propylamidinourea in 20 ml of $CH_3CN$ is added 9.52 g (80 mmol) of N,N-dimethylformamide dimethylacetal and an additional 20 ml of $CH_3CN$. The solid dissolves but not entirely, perhaps due to formation of new solid. The reactant mixture is heated to reflux and the solid dissolved. After the solution is refluxed for 0.5 hours, the solution is allowed to cool to ambient temperature and stirred overnight. The next morning a solid has appeared.

The reaction mixture is concentrated in vacuo to yield an off-white solid which is taken up in $CHCl_3$, washed with $H_2O$ (3×50 ml) and saturated aqueous brine (2×50 ml). All aqueous wash layers are combined and back-extracted with $CHCl_3$. All organic layers are combined, dried ($Na_2SO_4$), filtered and the filtrate concentrated in vacuo to yield an off-white solid which is dissolved in MeOH, acidified with HCl/MeOH and concentrated in vacuo to give 1-(2',6'-diethylphenyl)-4-n-propylamino-1,2-dihydro-1,3,5-triazin-2-one.HCl. Analysis calculated for $C_{16}H_{23}ClN_4O$.

Calculated: 59.53%C; 7.18%H; 10.98%Cl; 17.35%N. Found: 59.04%C; 7.35%H; 11.29%Cl; 17.37%N.

EXAMPLE 31

4-n-Butylamino-1-(2',6'-diethylphenyl)-1,2-dihydro-1,3,5-triazin-2-one

To a solution of 8.7 g (0.03 mol) of 3-n-butylamidino-1-(2',6'-dimethylphenyl)-urea in $CH_3C \equiv N$ (50 ml) are added 7.2 g (0.06 mol) of DMF-DMA and the mixture is refluxed for 2 hours. The solvent is removed under vacuum to give a solid residue which is dissolved in MeOH (warm) and acidified with HCl/MeOH. The MeOH is removed under vacuum to give an oil.

This oil is dissolved in EtoAc. The EtoAc is removed under vacuum and the residue dissolved in $CH_2Cl_2$ and washed with 10% aqueous NaOH (1×50 ml). The aqueous layer is extracted with $CH_2CL_2$ (6×75 ml) and the $CH_2Cl_2$ extracted, combined, dried ($MgSO_4$) and concentrated under reduced pressure to a solid which is crystallized from EtoAc to give 5.5 g of 4-n-butylamino-1-(2',6'-diethylphenyl)-1,2-dihydro-1,3,5-triazin-2-one as a white solid, m.p. 178°-9° C.

We claim:
1. 1-(2,6-dimethylphenyl)-4-(dimethylamino)-1,3,5-triazin-2-one or an acid addition salt thereof.

* * * * *